Figure 3:
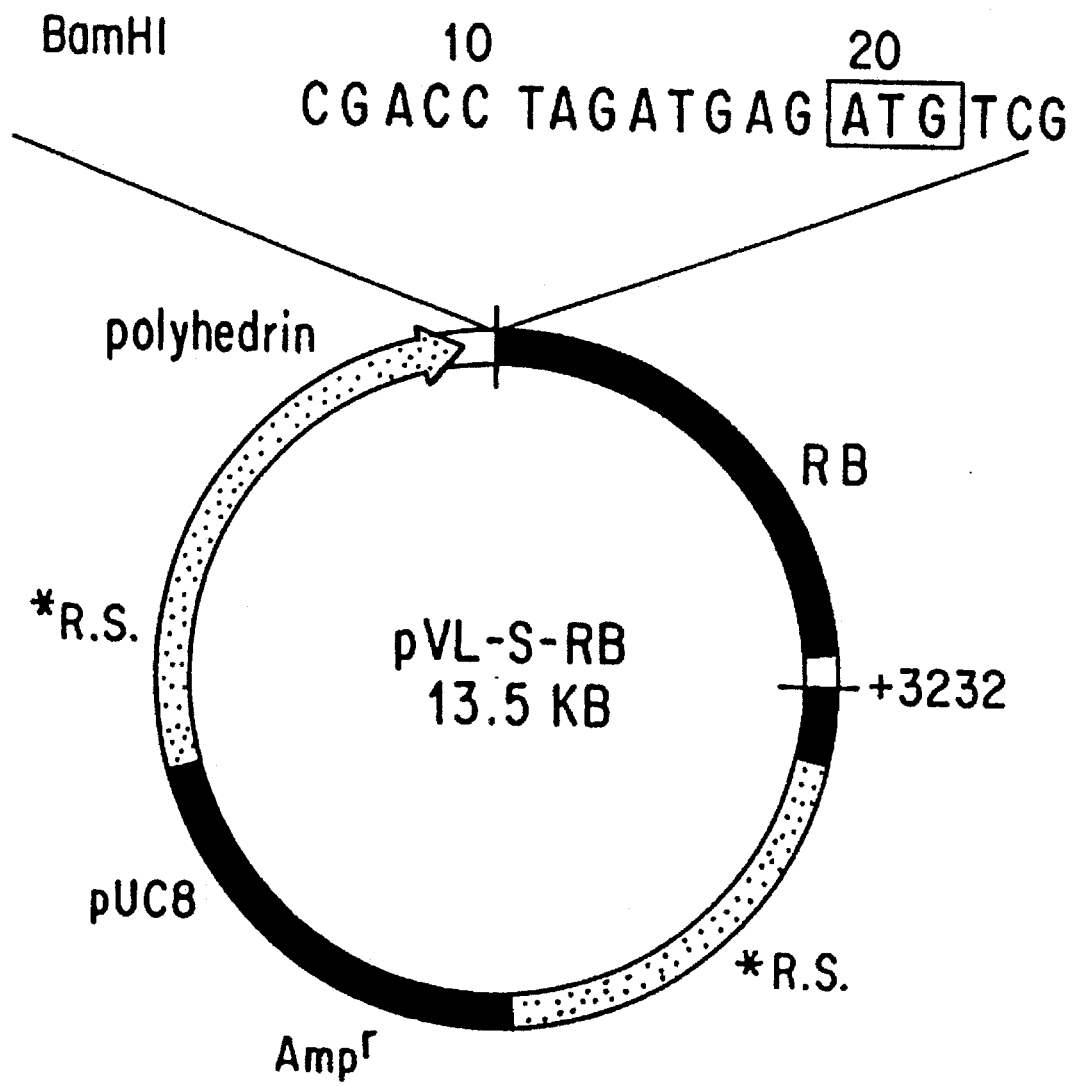

United States Patent [19]

Xu et al.

[11] Patent Number: 5,496,731
[45] Date of Patent: Mar. 5, 1996

[54] BROAD-SPECTRUM TUMOR SUPPRESSOR GENES, GENE PRODUCTS AND METHODS FOR TUMOR SUPPRESSOR GENE THERAPY

[76] Inventors: Hong-Ji Xu; Shi-Xue Hu, both of 10 Moonseed Pl.; William F. Benedict, 21 E. Wedgewood Glen, all of The Woodlands, Tex. 77381

[21] Appl. No.: 38,760

[22] Filed: Mar. 25, 1993

[51] Int. Cl.$^6$ ............................ C12N 15/86; C12N 15/85
[52] U.S. Cl. ...................... 435/320.1; 536/23.5; 514/44
[58] Field of Search ................................. 536/350, 23.5; 435/69.1, 320.1

[56] References Cited

U.S. PATENT DOCUMENTS

| | | | |
|---|---|---|---|
| 4,740,463 | 4/1984 | Weinberg et al. | 435/68.1 |
| 4,942,123 | 9/1987 | Lee et al. | 435/7.23 |
| 5,174,993 | 6/1990 | Paoletti | 424/199.1 |

FOREIGN PATENT DOCUMENTS

| | | |
|---|---|---|
| 80426/91 | 7/1991 | Australia . |
| 0259031 | 8/1987 | European Pat. Off. . |
| WO88/09387 | 5/1988 | WIPO . |
| WO89/03429 | 8/1988 | WIPO . |
| WO89/06703 | 1/1989 | WIPO . |
| WO90/05180 | 10/1989 | WIPO . |
| WO90/12807 | 4/1990 | WIPO . |
| WO91/15580 | 4/1991 | WIPO . |
| WO92/05272 | 9/1991 | WIPO . |

OTHER PUBLICATIONS

Ferrailo et al *Protein Pharmacokinetics & Metabolism* Chapt 1 pp. 1–34 1992 Plenum Press New York, New York.
Konrad Biological Barriers to Protein Delivery Cpt 14 pp. 409–435 1992 Plenum Press New York, New York.
Verma, Scientific American vol. 263(5) pp. 68–84, 1990.
Rosenfeld et al Cell vol. 68 pp. 143–155, 1992.
Karson et al. Jour. Rep. Medicine vol. 37 (6) pp. 500–514, Jun. 1992.
Af Trampe et al., 1983, Results Obtained in Treating Retinoblastoma patients with Diffrent Techniques at the Karolinska Hospital, *Springer–Verlag* pp. 529–533.
Ahlering et al., 1987, A New in Vivo Model to Study Invasion and Metastasis of Human Bladder Carcinoma, *Cancer Research* 47:6660–6665.
Akiyama et al., 1990, Marked alteration in phosphorylation of the RB protein during differentiation of human promyelocytic HL 60 cells, *Oncogene* 5:179–183.
Anderson, 1992, Human Gene Therapy, *Science* 256:808–813.
Ausubel et al., 1992, Short Protocols in Molecular Biology, *Current Protocols in Molecular Biology*, John Wiley and Jones, New York.
Baker et al., 1990, Suppression of Human Colorectal Carcinoma Cell Growth by Wild–Type p. 53, *Science* 249:912–915.
Ballester et al, 1990, The NF1 Locus Encodes a Protein Functionally Related to Mammalian GAP and Yeast IRA Proteins, *Cell* 63:851–859.

Banerjee et al., 1992, Changes in Growth and Tumorigenicity following Reconstitution of Retinoblastoma Gene Function in Various Human Cancer Cell Types by Microcell Transfer of Chromosome 13, *Cancer Research* 52:6297–6304.
Bayer et al., 1980, The Use of the Avidin–Biotin Complex as a Tool in Molecular Biology, *Methods Biochem. Anal.* 26:1–45.
Benedict et al., 1990, Role of the Retinoblastoma Gene in the Initiation and Progression of Human Cancer, *J. Clin. Invest.* 85:988–993.
Benoist et al., 1981, In vivo sequence requirements of the SV40 early promoter region, *Nature* 290:304–310.
Bookstein et al., 1991, Molecular Genetics of the Retinoblastoma Suppressor Gene, *Crit. Rev. Oncog.* 2(3):211–227.
Bookstein et al, 1990, Suppression of Tumorigenicity of Human Prostate Carcinoma Cells by Replacing a Mutated RB Gene, *Science* 247:712–715.
Brinster et al., 1982, Regulation of metallothionein–thymidine kinase fusion plasmids injected into mouse eggs, *Nature* 296:39–42.2.
Brown et al., 1984 Mechanism of activation of an N–ras gene in the human fibrosarcoma cell line HT1080, *EMBO J.* 3(6):1321–1326.
Buchkovich et al., 1989, The Retinoblastoma Protein is Phosphorylated during Specific Phases of the Cell Cycle, *Cell* 58:1097–1105.
Ceccoli et al., 1989, Encapsulation of the UV–DNA Repair Enzyme T4 Endocuclease V in Liposomes and Delivery to Human Cells, *Journal of Investigative Dermatology* 93:190–194.
Chen et al., 1989, Phosphorylation of the Retinoblastoma Gene Product is Modulated during the Cell Cycle and Cellular Differentiation, *Cell* 58:1193–1198.
Culver et al., 1992, In Vivo Gene Transfer with Retroviral Vector–Producer Cells for Treatment of Experimental Brain Tumors, *Science* 256:1550–1552.
Culver et al., 1991, Lymphocyte Gene Therapy, *Human Gene Therapy* 2:107–109.
Curiel et al., 1991, Adenovirus enhancement of transferrin–polysine–mediated gene delivery, *Proc. Natl. Acad. Sci. USA* 88:8850–8854.
Davies, 1992, Moving stright to the target, *Nature genetics* 358:519.

(List continued on next page.)

Primary Examiner—Richard A. Schwartz
Assistant Examiner—David B. Schmickel

[57] ABSTRACT

The present invention relates to a broad-spectrum tumor suppressor gene and the protein expressed by that gene in appropriate host cells. The protein is a second in-frame AUG codon-initiated retinoblasoma protein of about 94 kD relative molecular mass. The present invention also relates to methods of treating a mammal having a disease or disorder characterized by abnormal cellular proliferation, such as a tumor or cancer and methods of treating abnormally proliferating cells, such as tumor or cancer cells. Treatment is accomplished by inserting a host cell compatible p94$^{RB}$ expression vector or an effective amount of p94$^{RB}$ protein into a cell or cells in need of treatment.

12 Claims, 21 Drawing Sheets

OTHER PUBLICATIONS

DeCaprio et al., 1989, The Product of the Retinoblastoma Suceptibility Gene Has Properties of a Cell Cycle Regulatory Element, *Cell* 58:1085–1095.

Diller et al., 1990, p53 Functions as a Cell Cycle Control Protein in Osteosarcomas, *Molecular and Cellular Biology* 10(11):5772–5781.

Durst et al., Papillomavirus sequences integrate near cellular oncogenes in some cervical carcinomas, *Proc. Natl. Acad. Sci. USA* 84(4):1070–1074.

Fearon et al., 1990, A Genetic Model for Colorectal Tumorigenesis, *Cell* 61:759–767.

Francois et al., Mar./Apr., The Costenbader Memorial Lecture Genesis and Genetics of Retinoblastoma, *Journal of Pediatric Opthalmology and Strabismus* 16(2):85–100.

Friend et al., 1987, Deletions of a DNA sequence in retinoblastomas and mesenchymal tumors: Organization of the sequence and its encoded protein, *Proc. Natl. Acad. Sci. USA* 84:9059–9063.

Furukawa et al., 1990, Expression and state of phosphorylation of the retinoblastoma susceptibility gene product in cycling and noncycling human hematopoietic cells, *P.N.A.S. USA* 87:2770–2774.

Gallie et al, 1991, The Genetics of Retinoblastoma: Relevance to the Patient, *Pediatric Clinics of North America* 38(2):299–315.

Gallie et al., 1992, How Do Retinoblastoma Tumours Form?, *Eye* 6:226–231.

Goodrich et al., 1992, Abrogation by c–myc of G1 phase arrest induced by RB protein but not by p53, *Nature* 360:177–179.

Goodrich et al., 1992, Expression of the Retinoblastoma Gene Product in Bladder carcinoma Cells Associates with a Low Frequency of Tumor Formation, *Cancer Research* 52:1968–1973.

Gunning et al., 1987, A human β–actin expression vector system directs high–level accumulation of antisense transcripts, *Proc. Natl. Acad. Sci. USA* 84:4831–4835.

Hamel et al., 1992, Transcriptional Repression of the E2–Containing Promotors EllaE, c–myc, and RB1 by the Product of the RB1 Gene, *Molecular and Cellular Biology* 12(8):3431–3438.

Huang et al., 1988, Supresion of the Neoplastic Phenotype by Replacement of the RB Gene in Human Cancer Cells, *Science reports* 242:1563–1566.

Jaffe et al., 1992, Adenovirus–mediated in vivo gene transfer and expression in normal rat liver, *Nature genetics* 1:372–378.

Karasuyama et al., 1989, Autocrine Growth and Tumorigenicity of Interleukin 2–Dependent Helper T Cells Transfected with IL–2 Gene, *J. Exp. Med.* 169:13.

Klessig et al., 1984, Introduction, Stable Integration, and Controlled Expression of a Chimeric Adenoirus Gene Whose Product Is Toxic to the Recipient Human Cell, *Mol. Cell Biol.* 4:1354–1362.

Knight et al., 1988, Antiviral Therapy with Small Particle Aerosols, *European Journal of Clinical Microbiology and Infectious Diseases* 7(6):721–731.

Kratzke et al., 1992, Functional Analysis at the Cys–706 Residue of the Retinoblastoma Protein, *The Journal of Biological Chemistry* 267(36):25998–26003.

Kutty et al., 1992, Heme oxygenase: expression in human retina and modulation by stress agents in a human retinoblastoma cell model system, *Oxford University Press* 11(2):153–160.

Lee et al., 1990, Molecular biology of the Human Retinoblastoma Gene, *Immunol Ser.* 51:169–200.

Lee et al., 1987, The retinoblastoma susceptibility gene encodes a nuclear phosphoprotein associated with DNA binding activity, *Nature* 329:642–645.

Lemarchand et al., Adenovirus–mediated transfer of a recombinant human alpha$_1$–antitrypsin cDNA to human endothelial cells, *P.N.A.S. USA* 89:6482–6486.

Lin et al., 1992, Nasopharyngeal Carcinoma and Retinoblastoma Gene Expression, *Laboratory Investigation* 67(1):56–70.

Ludlow et al., 1989, SV40 Large T Antigen Binds Preferentially to an Underphosphorylated Member of the Retinoblastoma Suceptibility Gene Product Family, *Cell* 56:57–65.

Lynch et al., 1991, Production of High–Titer Helper Virus–Free Retroviral Vectors by Cocultivation of Packaging Cells with Different Host Ranges, *J. Virol.* 65:3887–3890.

Maniatis et al., 1989, *Molecular Cloning: A Laboratory Manual*, Cold Spring Harbor Laboratory, Cold Spring Harbor, New York.

Mannino et al., 1988, Liposome Mediated Gene Transfer, *Biotechniques* 6(7):682–690.

Marshall, 1991, Tumor Suppressor Genes, *Cell* 64:313–326.

McGee et al., 1989, Structure and partial genomic sequence of the human retinoblastoma susceptibility gene, *Gene* 80:119–128.

Mihara et al., 1989, Cell Cycle–Dependent regulation of Phosphorylation of the Human Retinoblastoma Gene Product, *Science* 246:1300–1303.

Miller, 1992, Human gene therapy comes of age, *Nature* 357:455–460.

Miller et al., 1986, Redesign of Retrovirus Packaging Cell Lines to Avoid Recombination Leading to Helper Virus Production, *Molec. Cell Biol.* 6(8):2895–2902.

Miller et al., 1985, Generation of Helper–Free Amphotropic Retroviruses That Transduce a Dominant–Acting, Methotrexate–Resistant Dihydrofolate Reductase Gene, *Molec. Cell Biol.* 5(3):431–437.

Miyanohara et al., 1988, Efficient expression of retroviral vector–transduced human low density lipoprotein (LDL) receptor–deficient rabbit fibroblasts in vitro, *Proc. Natl. Acad. Sci. USA* 85:6538–6542.

Murakami et al., 1991, Inactivation of the retinoblastoma gene in a human lung carcinoma cell line detected by single–strand conformation polymorphism analysis of the polymerase chain reaction product of cDNA, *Oncogene* 6:37–42.

Nabel et al., 1990, Site–Specific Gene Expression in Vivo by Direct Gene Transfer into the Arterial Wall, *Science* 249:1285–1288.

Newton et al., 1988, Vesicle–to–Cell Protein Transfer: Insertion of Band 3, the Erythrocyte Anion Transporter, into Lymphoid Cells, *Biochemistry* 27:4655–4659.

Riele et al., 1992, Highly efficient gene targeting in embryonic stem cells through homologous recombination with isogenic DNA constructs, *P.N.A.S. USA* 89:5128–5132.

Rosenfeld et al., 1992, In Vivo Transfer of the Human Cystic Fibrosis Transmembrane Conductance Regulator Gene to the Airway Epithelium, *Cell* 68:143–155.Schier, 1992, Conversations: Gene Therapy, *The Cancer Bulletin* 44(3)167.

Shew et al., 1990, C–terminal truncation of the retinoblastoma gene product leads to functional inactivation, *P.N.A.S. USA* 87:6–10.

Shew et al., 1989, Antibodies Detecting Abnormalities of the Retinoblastoma Susceptibility Gene Product (pp. 110–RB) in Osteosarcomas and Synovial Sarcomas, *Ocogene Research* 1:205–214.

Stein et al., 1990, Failure to Phosphorylate the Retinoblastoma Gene Product in Senescent Human Fibroblasts, *Science* 249:666–669.

Stone, 1992, Molecular 'Surgery' for Brain Tumors, *Science* 256:1513.

Sugawara et al., 1991, Distribution of c–yes–1 gene product in various cells and tissues, *Br. J. Cancer* 63(4):508–513.

Takahashi et al., 1991, The retinoblastoma gene functions as a growth and tumor suppressor in human bladder carcinoma cells, *Proc. Natl. Acad. Sci. USA* 88:5257–5261.

Tanswell et al., 1990, Response of fetal rat lung fibroblasts to elevated oxygen concentrations after liposome–mediated augmentation of antioxidant enzymes, *Biochimica et Biophysica Acta* 1044:269–274.

Templeton et al., 1991, Nonfunctional mutants of the retinoblastoma protein are characterized by defects in phosphorylation, viral oncoprotein association, and nuclear tethering, *Proc. Natl. Acad. Sci. USA* 88:3033–3037.

Thompson, 1992, Stem–Cell Gene Therapy Moves Toward Approval, *Science* 255:1072.

Uzvolgyi et al., 1991, Reintroduction of a Normal Retinoblastoma Gene into Retinoblastoma and Osteosarcoma Cells Inhibits the Replication associated Function of SV40 Large T Antigen, *Cell Growth & Differentiation* 2:297–303.

Wagner et al., 1981, Nucleotide sequence of the thymidine kinase gene of herpes simplex virus type 1, *Proc. Natl. Acad. Sci. USA* 78(3):1441–1445.

Weinberg, 1991, Tumor Suppressor Genes, *Science articles* 254:1138–1146.

Weinberg, 1989, Oncogenes, Antioncogenes, and the Molecular Bases of Multistep Carcinogenesis, *Cancer Research* 49:3713–3721.

Weiss et al., 1985, *RNA Tumor Viruses*, Cold Spring Harbor, New York.

Whyte et al., 1988, Association between an oncogene and an anti–oncogene: the adenovirus E1A proteins bind to the retinoblastoma gene product, *Nature* 334:124–129.

Wolfe et al., 1992, Herpesvirus vector gene transfer and express of β–glucuronidase in the central nervous system of MPS VII mice, *Nature Genetics* 1:379–384.

Wu et al., 1991, Receptor–mediated Gene Delivery in Vivo: Partial Correction of Genetic Analbuminemia in Nagase Rats, *J. Biol. Chem.* 266:14338–14342.

Xu et al., 1991, Intraocular Tumor formation of RB Reconstituted reinoblastoma Cells, *Cancer Research* 51:4481–4485.

Xu et al., 1991, Lack of nuclear RB protein staining in G0/middle G1 cells: correlation to changes in total RB protein level, *Oncogene* 6:1139–1146.

Xu et al., 1989, The retinoblastoma susceptibility gene product: a characteristic pattern in normal cells and abnormal expression in malignant cells, *Oncogene* 4:807–812.

Yamada et al., 1985, Overproduction of the protein product of a nonselected foreign gene carried by an adenovirus vector, *Proc. Natl. Acad. Sci. USA* 82(11):3567–71.

Yamamoto et al., 1980, Identification of a Functional Promoter in the Long Terminal Repeat of Rous Sarcoma Virus, *Cell* 22:787–797.

Yokota et al., 1988, Altered expression of the retinoblastoma (RB) gene in small–cell carcinoma of the lung, *Oncogene* 3:471–475.

Zhou et al., 1993, Characterization of RB+ clones of RB reconstituted retinoblastoma and osteosarcoma cells, *Proc. Am. Assoc. Cancer Res.* 34:538 abstract No. 3214.

```
        10          20          30          40          50          60
5' GATCCCGACC TAGATGAGAT GTCGTTCACT TTTACTGAGC TACAGAAAAA CATAGAAATC
3'    GGCTGG ATCTACTCTA CAGCAAGTGA AAATGACTCG ATGTCTTTTT GTATCTTTAG
         70          80          90         100         110         120
   AGTGTCCATA AATTCTTTAA CTTACTAAAA GAAATTGATA CCAGTACCAA AGTTGATAAT
   TCACAGGTAT TTAAGAAATT GAATGATTTT CTTTAACTAT GGTCATGGTT TCAACTATTA
        130         140         150         160         170         180
   GCTATGTCAA GACTGTTGAA GAAGTATGAT GTATTGTTTG CACTCTTCAG CAAATTGGAA
   CGATACAGTT CTGACAACTT CTTCATACTA CATAACAAAC GTGAGAAGTC GTTTAACCTT
        190         200         210         220         230         240
   AGGACATGTG AACTTATATA TTTGACACAA CCCAGCAGTT CGATATCTAC TGAAATAAAT
   TCCTGTACAC TTGAATATAT AAACTGTGTT GGGTCGTCAA GCTATAGATG ACTTTATTTA
        250         260         270         280         290         300
   TCTGCATTGG TGCTAAAAGT TTCTTGGATC ACATTTTTAT TAGCTAAAGG GGAAGTATTA
   AGACGTAACC ACGATTTTCA AGAACCTAG TGTAAAAATA ATCGATTTCC CCTTCATAAT
        310         320         330         340         350         360
   CAAATGGAAG ATGATCTGGT GATTTCATTT CAGTTAATGC TATGTGTCCT TGACTATTTT
   GTTTACCTTC TACTAGACCA CTAAAGTAAA GTCAATTACG ATACACAGGA ACTGATAAAA
        370         380         390         400         410         420
   ATTAAACTCT CACCTCCCAT GTTGCTCAAA GAACCATATA AAACAGCTGT TATACCCATT
   TAATTTGAGA GTGGAGGGTA CAACGAGTTT CTTGGTATAT TTTGTCGACA ATATGGGTAA
        430         440         450         460         470         480
   AATGGTTCAC CTCGAACACC CAGGCGAGGT CAGAACAGGA GTGCACGGAT AGCAAAACAA
   TTACCAAGTG GAGCTTGTGG GTCCGCTCCA GTCTTGTCCT CACGTGCCTA TCGTTTTGTT
        490         500         510         520         530         540
   CTAGAAAATG ATACAAGAAT TATTGAAGTT AACATGAAGTT CTCTGTAAAG TAATATAGAT
   GATCTTTTAC TATGTTCTTA ATAACTTCAA GAGACATTTC AACATGAAAG ATTATATCTA
```

FIG. 1A

```
         550        560        570        580        590        600
GAGGTGAAAA ATGTTTATTT CAAAAATTTT ATACCTTTTA TGAATTCTCT TGGACTTGTA
CTCCACTTTT TACAAATAAA GTTTTAAAA  TATGGAAAAT ACTTAAGAGA ACCTGAACAT
         610        620        630        640        650        660
ACATCTAATG GACTTCCAGA GGTTGAAAAT CTTTCTAAAC GATACGAAGA AATTTATCTT
TGTAGATTAC CTGAAGGTCT CCAACTTTTA GAAAGATTTG CTATGCTTCT TTAAATAGAA
         670        680        690        700        710        720
AAAAATAAAG ATCTAGATGC AAGATTATTT TTGGATCATG ATAAAAACTCT TCAGACTGAT
TTTTTATTTC TAGATCTACG TTCTAATAAA AACCTAGTAC TATTTTGAGA AGTCTGACTA
         730        740        750        760        770        780
TCTATAGACA GTTTGAAAC  ACAGAGAACA CCACGAAAAA GTAACCTTGA TGAAGAGGTG
AGATATCTGT CAAAACTTTG TGTCTCTTGT GGTGCTTTTT CATTGGAACT ACTTCTCCAC
         790        800        810        820        830        840
AATGTAATTC CTCCACACAC TCCAGTTAGG ACTGTTATGA ACACTATCCA ACAATTAATG
TTACATTAAG GAGGTGTGTG AGGTCAATCC TGACAATACT TGTGATAGGT TGTTAATTAC
         850        860        870        880        890        900
ATGATTTTAA ATTCAGCAAG TGATCAACCT TCAGAAAATC TGATTTCCTA TTTTAACAAC
TACTAAAATT TAAGTCGTTC ACTAGTTGGA AGTCTTTTAG ACTAAAGGAT AAAATTGTTG
         910        920        930        940        950        960
TGCACAGTGA ATCCAAAAGA AAGTATACTG AAAAGAGTGA AGGATATAGG ATACATCTTT
ACGTGTCACT TAGGTTTTCT TTCATATGAC TTTTCTCACT TCCTATATCC TATGTAGAAA
         970        980        990       1000       1010       1020
AAAGAGAAAT TTGCTAAAGC TGTGGGACAG GGTTGTGTCG AAATTGGATC ACAGCGATAC
TTTCTCTTTA AACGATTTCG ACACCCTGTC CCAACACAGC TTTAACCTAG TGTCGCTATG
        1030       1040       1050       1060       1070       1080
AAACTTGGAG TTCGCTTGTA TTACCGAGTA ATGGAATCCA TGCTTAAATC AGAAGAAGAA
TTTGAACCTC AAGCGAACAT AATGGCTCAT TACCTTAGGT ACGAATTTAG TCTTCTTCTT
```

FIG. 1B

```
      1090       1100       1110       1120       1130       1140
CGATTATCCA TTCAAAATTT TAGCAAACTT CTGAATGACA ACATTTTCA  TATGTCTTTA
GCTAATAGGT AAGTTTTAAA ATCGTTTGAA GACTTACTGT TGTAAAAAGT ATACAGAAAT
      1150       1160       1170       1180       1190       1200
TTGGCGTGCG CTCTTGAGGT TGTAATGGCC ACATATAGCA GAAGTACATC TCAGAATCTT
AACCGCACGC GAGAACTCCA ACATTACCGG TGTATATCGT CTTCATGTAG AGTCTTAGAA
      1210       1220       1230       1240       1250       1260
GATTCTGGAA CAGATTTGTC TTTCCCATGG ATTCTGAATG TGCTTAATTT AAAAGCCTTT
CTAAGACCTT GTCTAAACAG AAAGGGTACC TAAGACTTAC ACGAATTAAA TTTTCGGAAA
      1270       1280       1290       1300       1310       1320
GATTTTACA  AAGTGATCGA AAGTTTTATC AAAGCAGAAG GCAACTTGAC AAGAGAAATG
CTAAAAATGT TTCACTAGCT TTCAAAATAG TTTCGTCTTC CGTTGAACTG TTCTCTTTAC
      1330       1340       1350       1360       1370       1380
ATAAACATT  TAGAACGATG TGAACATCGA ATCATGGAAT CCCTTGCATG GCTCTCAGAT
TATTTTGTAA ATCTTGCTAC ACTTGTAGCT TAGTACCTTA GGGAACGTAC CGAGAGTCTA
      1390       1400       1410       1420       1430       1440
TCACCTTTAT TTGATCTTAT TAAACAATCA AAGGACCGAG AAGGACCAAC TGATCACCTT
AGTGGAAATA AACTAGAATA ATTTGTTAGT TTCCTGGCTC TTCCTGGTTG ACTAGTGGAA
      1450       1460       1470       1480       1490       1500
GAATCTGCTT GTCCTCTTAA TCTTCCTCTC CAGAATAATC ACACTGCAGC AGATATGTAT
CTTAGACGAA CAGGAGAATT AGAAGGAGAG GTCTTATTAG TGTGACGTCG TCTATACATA
      1510       1520       1530       1540       1550       1560
CTTTCTCCTG TAAGATCTCC AAAGAAAAAA GGTTCAACTA CGCGTGTAAA TTCTACTGCA
GAAAGAGGAC ATTCTAGAGG TTTCTTTTTT CCAAGTTGAT GCGCACATTT AAGATGACGT
      1570       1580       1590       1600       1610       1620
AATGCAGAGA CACAAGCAAC CTCAGCCTTC CAGACCCAGA AGCCATTGAA ATCTACCTCT
TTACGTCTCT GTGTTCGTTG GAGTCGGAAG GTCTGGGTCT TCGGTAACTT TAGATGGAGA
```

FIG. 1C

FIG. 1D

```
      1630       1640       1650       1660       1670       1680
CTTTCACTGT TTTATAAAAA AGTGTATCGG CTAGCCTATC TCCGGCTAAA TACACTTTGT
GAAAGTGACA AAATATTTT  TCACATAGCC GATCGGATAG AGGCCGATTT ATGTGAAACA
      1690       1700       1710       1720       1730       1740
GAACGCCTTC TGTCTGAGCA CCCAGAATTA GAACATATCA TCTGGACCCT TTTCCAGCAC
CTTGCGGAAG ACAGACTCGT GGGTCTTAAT CTTGTATAGT AGACCTGGGA AAAGGTCGTG
      1750       1760       1770       1780       1790       1800
ACCCTGCAGA ATGAGTATGA ACTCATGAGA GACAGGCATT TGGACCAAAT TATGATGTGT
TGGGACGTCT TACTCATACT TGAGTACTCT CTGTCCGTAA ACCTGGTTTA ATACTACACA
      1810       1820       1830       1840       1850       1860
TCCATGTATG GCATATGCAA AGTGAAGAAT ATAGACCTTA AATTCAAAAT CATTGTAACA
AGGTACATAC CGTATACGTT TCACTTCTTA TATCTGGAAT TTAAGTTTTA GTAACATTGT
      1870       1880       1890       1900       1910       1920
GCATACAAGG ATCTTCCTCA TGCTGTTCAG GAGACATTCA AACGTGTTTT GATCAAAGAA
CGTATGTTCC TAGAAGGAGT ACGACAAGTC CTCTGTAAGT TTGCACAAAA CTAGTTTCTT
      1930       1940       1950       1960       1970       1980
GAGGAGTATG ATTCTATTAT AGTATTCTAT AACTCGGTCT TCATGCAGAG ACTGAAAACA
CTCCTCATAC TAAGATAATA TCATAAGATA TTGAGCCAGA AGTACGTCTC TGACTTTTGT
      1990       2000       2010       2020       2030       2040
AATATTTTGC AGTATGCTTC CACCAGCCCC CCTACCTTGT CACCAATACC TCACATTCCT
TTATAAAACG TCATACGAAG GTGGTCCGGG GGATGGAACA GTGGTTATGG AGTGTAAGGA
      2050       2060       2070       2080       2090       2100
CGAAGCCCTT ACAAGTTTCC TAGTTCACCC TTACGGATTC CTGGAGGGAA CATCTATATT
GCTTCGGGAA TGTTCAAAGG ATCAAGTGGG AATGCCTAAG GACCTCCCTT GTAGATATAA
      2110       2120       2130       2140       2150       2160
TCACCCCTGA AGAGTCCATA TAAAATTTCA GAAGGTCTGC CAACACCAAC AAAAATGACT
AGTGGGGACT TCTCAGGTAT ATTTTAAAGT CTTCCAGACG GTTGTGGTTG TTTTTACTGA
```

FIG. 1E

```
2170        2180        2190        2200        2210        2220
CCAAGATCAA  GAATCTTAGT  ATCAATTGGT  GAATCATTCG  GGACTTCTGA  GAAGTTCCAG
GGTTCTAGTT  CTTAGAATCA  TAGTTAACCA  CTTAGTAAGC  CCTGAAGACT  CTTCAAGGTC
        2230        2240        2250        2260        2270        2280
AAATAAATC   AGATGGTATG  TAACAGCGAC  CGTGTGCTCA  AAAGAAGTGC  TGAAGGAAGC
TTTTATTTAG  TCTACCATAC  ATTGTCGCTG  GCACACGAGT  TTTCTTCACG  ACTTCCTTCG
        2290        2300        2310        2320        2330        2340
AACCCTCCTA  AACCACTGAA  AAAACTACGC  TTTGATATTG  AAGGATCAGA  TGAAGCAGAT
TTGGGAGGAT  TTGGTGACTT  TTTTGATGCG  AAACTATAAC  TTCCTAGTCT  ACTTCGTCTA
        2350        2360        2370        2380        2390        2400
GGAAGTAAAC  ATCTCCCAGG  AGAGTCCAAA  TTTCAGCAGA  AACTGGCAGA  AATGACTTCT
CCTTCATTTG  TAGAGGGTCC  TCTCAGTTT   AAAGTCGTCT  TTGACCGTCT  TTACTGAAGA
        2410        2420        2430        2440        2450        2460
ACTCGAACAC  GAATGCAAAA  GCAGAAAATG  AATGATAGCA  TGGATACCTC  AAACAAGGAA
TGAGCTTGTG  CTTACGTTTT  CGTCTTTTAC  TTACTATCGT  ACCTATGGAG  TTTGTTCCTT
        2470        2480        2490        2500        2510        2520
GAGAAATGAG  GATCTCAGGA  CCTTGGTGGA  CACTGTGTAC  ACCTCTGGAT  TCATTGTCTC
CTCTTTACTC  CTAGAGTCCT  GGAACCACCT  GTGACACATG  TGGAGACCTA  AGTAACAGAG
        2530        2540        2550        2560        2570        2580
TCACAGATGT  GACTGTATAA  CTTCCCAGG   TTCTGTTTAT  GGCCACATTT  AATATCTTCA
AGTGTCTACA  CTGACATATT  GAAAGGTCC   AAGACAAATA  CCGGTGTAAA  TTATAGAAGT
        2590        2600        2610        2620        2630        2640
GCTCTTTTTG  TGGATATAAA  ATGTGCAGAT  GCAATTGTTT  GGGTGATTCC  TAAGCCACTT
CGAGAAAAAC  ACCTATATTT  TACACGTCTA  CGTTAACAAA  CCCACTAAGG  ATTCGGTGAA
        2650        2660        2670        2680        2690        2700
GAAATGTTAG  TCATTGTTAT  TTATACAAGA  TTGAAAATCT  TGTGTAAATC  CTGCCATTTA
CTTTACAATC  AGTAACAATA  AATATGTTCT  AACTTTTAGA  ACACATTTAG  GACGGTAAAT
```

```
            2710                2720                2730                2740                2750                2760
AAAAGTTGTA   GCAGATTGTT   TCCTCTTCCA   AAGTAAAATT   GCTGTGCTTT   ATGGATAGTA
TTTTCAACAT   CGTCTAACAA   AGGAGAAGGT   TTCATTTTAA   CGACACGAAA   TACCTATCAT
            2770                2780                2790                2800                2810                2820
AGAATGGCCC   TAGAGTGGGA   GTCCTGATAA   CCCAGGCCTG   TCTGACTACT   TTGCCTTCTT
TCTTACCGGG   ATCTCACCCT   CAGGACTATT   GGGTCCGGAC   AGACTGATGA   AACGGAAGAA
            2830                2840                2850                2860                2870                2880
TTGTAGCATA   TAGGTGATGT   TTGCTCTTGT   TTTTATTAAT   TTATATGTAT   ATTTTTTAA
AACATCGTAT   ATCCACTACA   AACGAGAACA   AAAATAATTA   AATATACATA   TAAAAAATT
            2890                2900                2910                2920                2930                2940
TTTAACATGA   ACACCCTTAG   AAAATGTGTC   CTATCTATCT   TCCAAATGCA   ATTTGATTGA
AAATTGTACT   TGTGGGAATC   TTTTACACAG   GATAGATAGA   AGGTTTACGT   TAAACTAACT
            2950                2960                2970                2980                2990                3000
CTGCCCATTC   ACCAAAATTA   TCCTGAACTC   TTCTGCAAAA   ATGGATATTA   TTAGAAATTA
GACGGGTAAG   TGGTTTTAAT   AGGACTTGAG   AAGACGTTTT   TACCTATAAT   AATCTTTAAT
            3010                3020                3030                3040                3050                3060
GAAAAAAATT   ACTAATTTA    CACATTAGAT   TTTATTTTAC   TATTGGAATC   TGATATACTG
CTTTTTTAA    TGATTAAAAT   GTGTAATCTA   AAATAAAATG   ATAACCTTAG   ACTATATGAC
            3070                3080                3090                3100                3110                3120
TGTGCTTGTT   TTATAAAATT   TTGCTTTTAA   TTAAATAAAA   TTCATACCTC   AGAATGTAAA   AAGTATAACC
ACACGAACAA   AATATTTAA    AACGAAAATT   AATTATTTT   AAGTATGGAG   TCTTACATTT   TCTTGAATGG
            3130                3140                3150                3160                3170                3180
ATATGATACT   ATCATACTAC   TGAAACAGAT   TTCATACCTC   AGAATGTAAA   AGAACTTACT
TATACTATGA   TAGTATGATG   ACTTTGTCTA   AAGTATGGAG   TCTTACATTT   TCTTGAATGA
            3190                3200                3210                3220                3230
GATTATTTTC   TTCATCCAAC   TTATGTTTTT   AAATGAGGAT   TATTGATAGT            GG       3'
CTAATAAAAG   AAGTAGGTTG   AATACAAAAA   TTTACTCCTA   ATAACTATCA            CCCTAG   5'
```

FIG. 1F

```
                GATCCCGA CCTAGATGAG ATG TCG TTC ACT TTT ACT GAG CTA CAG AAA    48
                                   Met Ser Phe Thr Phe Thr Glu Leu Gln Lys    10

AAC ATA GAA ATC AGT GTC CAT AAA TTC TTT AAC TTA CTA AAA GAA ATT                96
Asn Ile Glu Ile Ser Val His Lys Phe Phe Asn Leu Leu Lys Glu Ile                26

GAT ACC AGT ACC AAA GTT GAT AAT GCT ATG TCA AGA TCA AGA TTG AAG AAG           144
Asp Thr Ser Thr Lys Val Asp Asn Ala Met Ser Arg Leu Leu Lys Lys               42

TAT GAT GTA TTG TTT GCA CTC TTC AGC AGT TTG GAA AGG ACA TGT GAA               192
Tyr Asp Val Leu Phe Ala Leu Phe Ser Ser Lys Leu Glu Arg Thr Cys Glu            58

CTT ATA TAT TTG ACA CAA CCC AGC AGT TCG ATA TCT ACT GAA ATA AAT               240
Leu Ile Tyr Leu Thr Gln Pro Ser Ser Ile Ser Thr Glu Ile Asn                    74

TCT GCA TTG GTG CTA AAA GTT TCT TGG ATC ACA TTT TTA TTA GCT AAA               288
Ser Ala Leu Val Leu Lys Val Ser Trp Ile Thr Phe Leu Leu Ala Lys                90

GGG GAA GTA TTA CAA ATG GAA GAT GAT CTG GTG ATT TCA TTT CAG TTA               336
Gly Glu Val Leu Gln Met Glu Asp Asp Leu Val Ile Ser Phe Gln Leu               106

ATG CTA TGT GTC CTT GAC TAT TTT ATT AAA CTC TCA CCT CCC ATG TTG               384
Met Leu Cys Val Leu Asp Tyr Phe Ile Lys Leu Ser Pro Pro Met Leu               122

CTC AAA GAA CCA TAT AAA ACA GCT GTT ATA CCC ATT AAT GGT TCA CCT               432
Leu Lys Glu Pro Tyr Lys Thr Ala Val Ile Pro Ile Asn Gly Ser Pro               138

CGA ACA CCC AGG CGA GGT CAG AAC AGG AGT GCA CGG ATA GCA AAA CAA               480
Arg Thr Pro Arg Arg Gly Gln Asn Arg Ser Ala Arg Ile Ala Lys Gln               154
```

FIG. 2A

| CTA | GAA | AAT | GAT | ACA | AGA | ATT | GAA | GTT | CTC | TGT | AAA | GAA | CAT | GAA | 528 |
| Leu | Glu | Asn | Asp | Thr | Arg | Ile | Glu | Val | Leu | Cys | Lys | Glu | His | Glu | 170 |
| TGT | AAT | ATA | GAT | GAG | GTG | AAA | GTT | TAT | TTC | AAA | AAT | TTT | ATA | CCT | 576 |
| Cys | Asn | Ile | Asp | Glu | Val | Lys | Val | Tyr | Phe | Lys | Asn | Phe | Ile | Pro | 186 |
| TTT | ATG | AAT | TCT | CTT | GGA | CTT | GTA | ACA | TCT | AAT | GGA | CTT | CCA | GAG | GTT | 624 |
| Phe | Met | Asn | Ser | Leu | Gly | Leu | Val | Thr | Ser | Asn | Gly | Leu | Pro | Glu | Val | 202 |
| GAA | AAT | CTT | TCT | AAA | CGA | TAC | GAA | ATT | TAT | CTT | AAA | AAT | AAA | AAA | GAT | 672 |
| Glu | Asn | Leu | Ser | Lys | Arg | Tyr | Glu | Ile | Tyr | Leu | Lys | Asn | Lys | Lys | Asp | 218 |
| CTA | GAT | GCA | AGA | TTA | TTT | TTG | GAT | CAT | GAT | AAA | ACT | CTT | CAG | ACT | GAT | 720 |
| Leu | Asp | Ala | Arg | Leu | Phe | Leu | Asp | His | Asp | Lys | Thr | Leu | Gln | Thr | Asp | 234 |
| TCT | ATA | GAC | AGT | TTT | GAA | ACA | CAG | AGA | ACA | CCA | CGA | AAA | AGT | AAC | CTT | 768 |
| Ser | Ile | Asp | Ser | Phe | Glu | Thr | Gln | Arg | Thr | Pro | Arg | Lys | Ser | Asn | Leu | 250 |
| GAT | GAA | GAG | GTG | AAT | GTA | ATT | CCT | CCA | CAC | ACT | CCA | GTT | AGG | ACT | GTT | 816 |
| Asp | Glu | Glu | Val | Asn | Val | Ile | Pro | Pro | His | Thr | Pro | Val | Arg | Thr | Val | 266 |
| ATG | AAC | ACT | ATC | CAA | CAA | TTA | ATG | ATT | TTA | AAT | TCA | GCA | AGT | GAT | 864 |
| Met | Asn | Thr | Ile | Gln | Gln | Leu | Met | Ile | Leu | Asn | Ser | Ala | Ser | Asp | 282 |
| CAA | CCT | TCA | GAA | AAT | CTG | ATT | TCC | TAT | TTT | AAC | AAC | TGC | ACA | GTG | AAT | 912 |
| Gln | Pro | Ser | Glu | Asn | Leu | Ile | Ser | Tyr | Phe | Asn | Asn | Cys | Thr | Val | Asn | 298 |
| CCA | AAA | GAA | AGT | ATA | CTG | AAA | AGA | GTG | AAG | GAT | ATA | GGA | TAC | ATC | TTT | 960 |
| Pro | Lys | Glu | Ser | Ile | Leu | Lys | Arg | Val | Lys | Asp | Ile | Gly | Tyr | Ile | Phe | 314 |

FIG. 2B

```
AAA GAG AAA TTT GCT AAA GCT GTG GGA CAG GGT TGT GTC GAA ATT GGA    1008
Lys Glu Lys Phe Ala Lys Ala Val Gly Gln Gly Cys Val Glu Ile Gly     330

TCA CAG CGA TAC CTT AAA CTT GGA GTT CGC TTG TAT TAC CGA ATG GAA    1056
Ser Gln Arg Tyr Leu Lys Leu Gly Val Arg Leu Tyr Tyr Arg Met Glu     346

TCC ATG CTT AAA TCA GAA GAA TCA CGA TTA TCC ATT CAA AAT TTT AGC    1104
Ser Met Leu Lys Ser Glu Glu Ser Arg Leu Ser Ile Gln Asn Phe Ser     362

AAA CTT CTG AAT GAC AAC ATT TTT CAT ATG TCT TTA GCG TTG TGC GCT    1152
Lys Leu Leu Asn Asp Asn Ile Phe His Met Ser Leu Leu Ala Cys Ala     378

CTT GAG GTT GTA ATG GCC ACA TAT AGC AGA ACA TCT CAG AAT CTT AAT    1200
Leu Glu Val Val Met Ala Thr Tyr Ser Arg Thr Ser Gln Asn Leu Asn     394

GAT TCT GGA ACA GAT TTG TCT TTC CCA ATT CTG AAT GTG CTT AAT         1248
Asp Ser Gly Thr Asp Leu Ser Phe Pro Ile Leu Asn Val Leu Asn         410

TTA AAA GCC TTT GAT TAC AAA GTG ATC GAA AGT TTT ATC AAA GCA         1296
Leu Lys Ala Phe Asp Tyr Lys Val Ile Glu Ser Phe Ile Lys Ala         426

GAA GGC AAC TTG ACA AGA GAA ATG ATA AAA CAT TTA GAA CGA TGT GAA    1344
Glu Gly Asn Leu Thr Arg Glu Met Ile Lys His Leu Glu Arg Cys Glu     442

CAT CGA ATC ATG GAA CTT GCA TGG CTC TCA GAT TCA CCT TTA TTT         1392
His Arg Ile Met Glu Ser Ala Trp Leu Ser Asp Ser Pro Leu Phe         458

GAT CTT ATT AAA CAA TCA AAG GAC CGA GAA GGA CCA ACT GAT CAC CTT    1440
Asp Leu Ile Lys Gln Ser Lys Asp Arg Glu Gly Pro Thr Asp His Leu     474
```

FIG. 2C

```
GAA TCT GCT TGT CCT CTT AAT CTT CCT CTC CAG AAT CAC ACT GCA   1488
Glu Ser Ala Cys Pro Leu Asn Leu Pro Leu Gln Asn His Thr Ala    490

GCA GAT ATG TAT CTT TCT CCT GTA AGA TCT CCA AAG AAA GGT TCA   1536
Ala Asp Met Tyr Leu Ser Pro Val Arg Ser Pro Lys Lys Gly Ser    506

ACT ACG CGT GTA AAT TCT GCA GCA AAT GAG ACA CAA GCA ACC TCA   1584
Thr Thr Arg Val Asn Ser Ala Ala Asn Glu Thr Gln Ala Thr Ser    522

GCC TTC CAG ACC CAG AAG CCA TTG AAA TCT ACC TCT CTT TCA TTT   1632
Ala Phe Gln Thr Gln Lys Pro Leu Lys Ser Thr Ser Leu Ser Phe    538

TAT AAA AAA GTG TAT CGG CTA GCC CTA TYR CTC CGG AAT ACA CTT TGT   1680
Tyr Lys Lys Val Tyr Arg Leu Ala Tyr Leu Arg Asn Thr Leu Cys    554

GAA CGC CTT CTG TCT GAG CAC CCA TTA GAA CAT ATC ATC TGG ACC   1728
Glu Arg Leu Leu Ser Glu His Pro Leu Glu His Ile Ile Trp Thr    570

CTT TTC CAG CAC ACC CTG CAG AAT GAG TAT GAA CTC ATG AGA GAC AGG   1776
Leu Phe Gln His Thr Leu Gln Asn Glu Tyr Glu Leu Met Arg Asp Arg  586

CAT TTG GAC CAA ATT ATG ATG TGT TCC ATG TAT GGC ATA TGC AAA GTG   1824
His Leu Asp Gln Ile Met Met Cys Ser Met Tyr Gly Ile Cys Lys Val  602

AAG AAT ATA GAC CTT AAA TTC AAA ATC ATT GTA ACA GCA TAC AAG GAT   1872
Lys Asn Ile Asp Leu Lys Phe Lys Ile Ile Val Thr Ala Tyr Lys Asp  618

CTT CCT CAT GCT GTT CAG GAG ACA TTC AAA CGT GTT TTG ATC AAA GAA   1920
Leu Pro His Ala Val Gln Glu Thr Phe Lys Arg Val Leu Ile Lys Glu  634
```

FIG. 2D

```
GAG GAG TAT GAT TCT ATT ATA GTA TTC TAT AAC TCG GTC TTC ATG CAG   1968
Glu Glu Tyr Asp Ser Ile Ile Val Phe Tyr Asn Ser Val Phe Met Gln    650

AGA CTG AAA ACA AAT ATT TTG CAG TAT GCT TCC ACC AGG CCC CCT ACC   2016
Arg Leu Lys Thr Asn Ile Leu Gln Tyr Ala Ser Thr Arg Pro Pro Thr    666

TTG TCA CCA ATA CCT CAC ATT CCT CGA AGC CCT TAC AAG TTT CCT AGT   2064
Leu Ser Pro Ile Pro His Ile Pro Arg Ser Pro Tyr Lys Phe Pro Ser    682

TCA CCC TTA CGG ATT CCT GGA ATT CCT GGG AAC ATC TAT ATT TCA CTG AAG   2112
Ser Pro Leu Arg Ile Pro Gly Gly Asn Ile Tyr Ile Ser Pro Leu Lys    698

AGT CCA TAT AAA ATT TCA GAA GGT CTG CCA ACA ACA CCA ATG ACT   2160
Ser Pro Tyr Lys Ile Ser Glu Gly Leu Pro Thr Pro Thr Lys Met Thr    714

CCA AGA ATC TCA GTA TCA ATT GGT GAA TTC GGT ACT ACT TCT   2208
Pro Arg Ser Arg Ile Leu Val Ser Ile Gly Glu Ser Phe Gly Thr Ser    730

GAG AAG TTC CAG AAA ATA AAT CAG ATG GTA TGT AAC AGC GAC CGT GTG   2256
Glu Lys Phe Gln Lys Ile Asn Gln Met Val Cys Asn Ser Asp Arg Val    746

CTC AAA AGA AGT GCT GAA GGA AGC AAC CCT CCT AAA CCA CTG AAA   2304
Leu Lys Arg Ser Ala Glu Gly Ser Asn Pro Pro Lys Pro Leu Lys Lys    762

CTA CGC TTT GAT ATT GAA GGA TCA GAT GAA GCA GAT GGA AGT AGT CAT   2352
Leu Arg Phe Asp Ile Glu Gly Ser Asp Glu Ala Asp Gly Ser Lys His    778

CTC CCA GGA GAG TCC AAA TTT CAG CAG AAA CTG GCA GAA ATG ACT TCT   2400
Leu Pro Gly Glu Ser Lys Phe Gln Gln Lys Leu Ala Glu Met Thr Ser    794
```

FIG. 2E

```
ACT CGA ACA CGA ATG CAA AAG CAG AAA ATG AAT GAT AGC ATG GAT ACC              2448
Thr Arg Thr Arg Met Gln Lys Gln Lys Met Asn Asp Ser Met Asp Thr               810

TCA AAC AAG GAA GAG AAA TGA GGATCTCAGG ACCTTGGTGG ACACTGTGTA                  2499
Ser Asn Lys Glu Glu Lys ***

CACCTCTGGA TTCATTGTCT CTCACAGATG TGACTGTATA ACTTTCCCAG GTTCTGTTTA             2559
TGGCCACATT TAATATCTTC AGTCTTTTT GTGGATATAA AATGTGCAGA TGCAATTGTT              2619
TGGGTGATTC CTAAGCCACT TGAAATGTTA GTCATTGTTA TTTATACAAG ATTGAAAATC             2679
TTGTGTAAAT CCTGCCATTT AAAAAGTTGT AGCAGATTGT TTCCTCTTCC AAAGTAAAAT             2739
TGCTGTGCTT TATGGATAGT AAGAATGGCC CTAGAGTGGG AGTCCTGATA ACCCAGGCCT             2799
GTCTGACTAC TTTGCCTTCT ATAGGTGATG AAACACCCTTA GAAAATGTGT CCTATCTATC            2859
TTTATATGTA TATTTTTTA ATTAACATG AACACCCTTA CACCAAAATT ATCCTGAACT CTTCTGCAAA    2919
ATCCAAATGC AATTTGATTG ACTGCCCATT CACCAAAATT TACTAATTT ACACATTAGA TTTTATTTA    2979
AATGGATATT ATTAGAAATT AGAAAAAAAT TACTAATTT ACACATTAGA TTTTATTTA              3039
CTATTGGAAT CTGATATACT GTGTGCTTGT TTTATAAAAT TTTGCTTTTA ATTAAATAAA             3099
AGCTGGAAGC AAAGTATAAC CATATGATAC TATCATACTA CTGAAACAGA TTTCATACCT             3159
CAGAATGTAA AAGAACTTAC TGATTATTTT CTTCATCCAA CTTATGTTTT TAAATGAGGA             3219
TTATTGATAG TGG                                                               3232
```

FIG. 2F

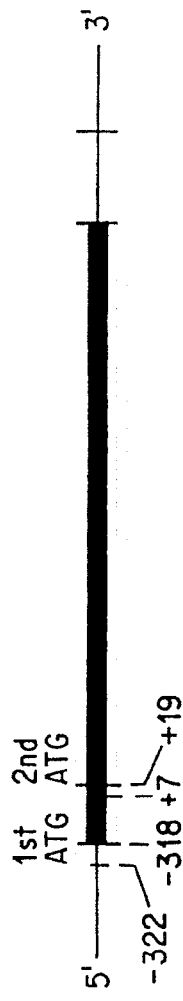
F I G. 6A
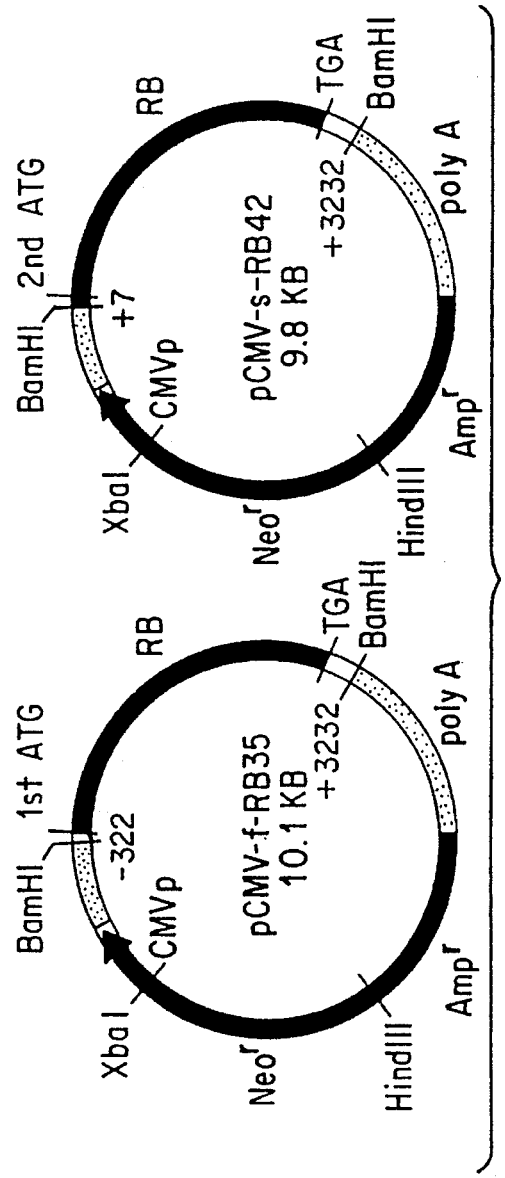
F I G. 6B

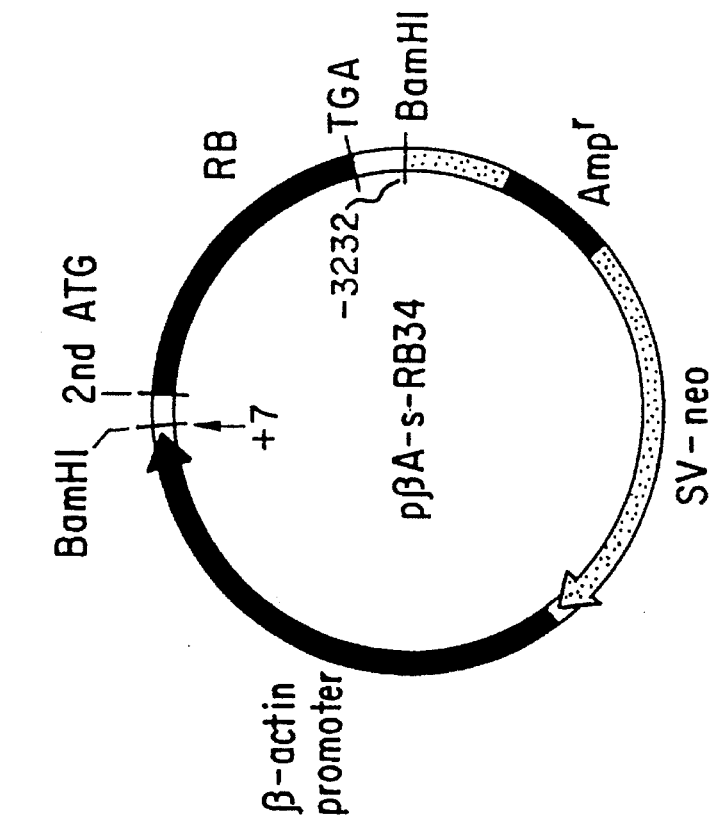
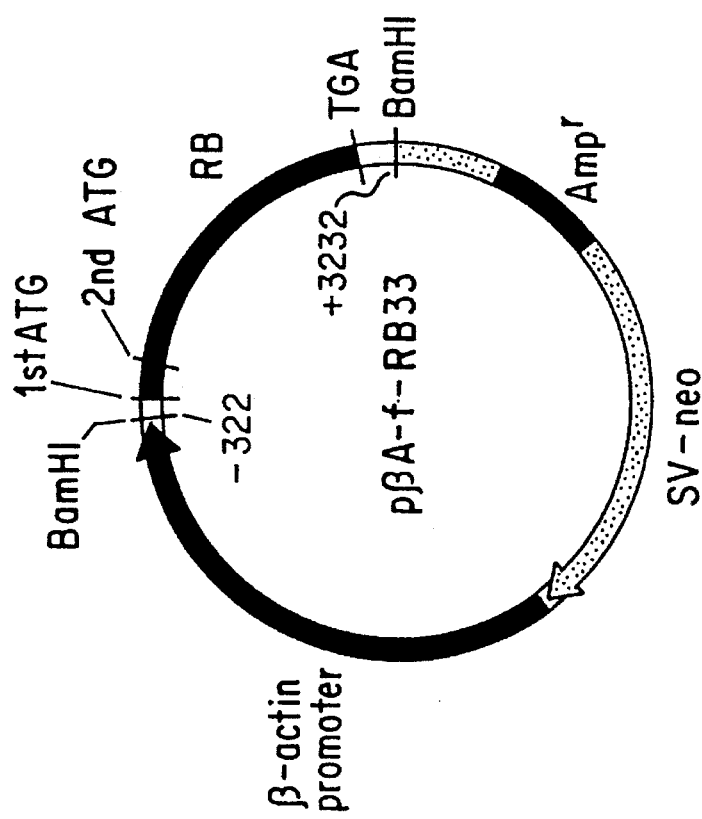

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
      ( A ) LENGTH: 3232 base pairs
      ( B ) TYPE: nucleic acid
      ( C ) STRANDEDNESS: double
      ( D ) TOPOLOGY: Not Relevant ( i i ) MOLECULE TYPE: DNA ( i x ) FEATURE:
      ( A ) NAME/KEY: CDS
      ( B ) LOCATION: 19..2469

( x i ) SEQUENCE DESCRIPTION: SEQ ID NO:1:

| | | | | | | | | | | | | | | | | |
|---|---|---|---|---|---|---|---|---|---|---|---|---|---|---|---|---|
| GATCCCGACC | TAGATGAG | ATG | TCG | TTC | ACT | TTT | ACT | GAG | CTA | CAG | AAA | AAC | | | | 51 |
| | | Met | Ser | Phe | Thr | Phe | Thr | Glu | Leu | Gln | Lys | Asn | | | | |
| | | 1 | | | | 5 | | | | | 10 | | | | | |
| ATA | GAA | ATC | AGT | GTC | CAT | AAA | TTC | TTT | AAC | TTA | CTA | AAA | GAA | ATT | GAT | 99 |
| Ile | Glu | Ile | Ser | Val | His | Lys | Phe | Phe | Asn | Leu | Leu | Lys | Glu | Ile | Asp | |
| | | | 15 | | | | 20 | | | | | 25 | | | | |
| ACC | AGT | ACC | AAA | GTT | GAT | AAT | GCT | ATG | TCA | AGA | CTG | TTG | AAG | AAG | TAT | 147 |
| Thr | Ser | Thr | Lys | Val | Asp | Asn | Ala | Met | Ser | Arg | Leu | Leu | Lys | Lys | Tyr | |
| | | 30 | | | | | 35 | | | | | | 40 | | | |
| GAT | GTA | TTG | TTT | GCA | CTC | TTC | AGC | AAA | TTG | GAA | AGG | ACA | TGT | GAA | CTT | 195 |
| Asp | Val | Leu | Phe | Ala | Leu | Phe | Ser | Lys | Leu | Glu | Arg | Thr | Cys | Glu | Leu | |
| | | 45 | | | | 50 | | | | | 55 | | | | | |
| ATA | TAT | TTG | ACA | CAA | CCC | AGC | AGT | TCG | ATA | TCT | ACT | GAA | ATA | AAT | TCT | 243 |
| Ile | Tyr | Leu | Thr | Gln | Pro | Ser | Ser | Ser | Ile | Ser | Thr | Glu | Ile | Asn | Ser | |
| 60 | | | | | 65 | | | | | 70 | | | | | 75 | |
| GCA | TTG | GTG | CTA | AAA | GTT | TCT | TGG | ATC | ACA | TTT | TTA | TTA | GCT | AAA | GGG | 291 |
| Ala | Leu | Val | Leu | Lys | Val | Ser | Trp | Ile | Thr | Phe | Leu | Leu | Ala | Lys | Gly | |
| | | | | 80 | | | | | 85 | | | | | 90 | | |
| GAA | GTA | TTA | CAA | ATG | GAA | GAT | GAT | CTG | GTG | ATT | TCA | TTT | CAG | TTA | ATG | 339 |
| Glu | Val | Leu | Gln | Met | Glu | Asp | Asp | Leu | Val | Ile | Ser | Phe | Gln | Leu | Met | |
| | | | 95 | | | | | 100 | | | | | 105 | | | |
| CTA | TGT | GTC | CTT | GAC | TAT | TTT | ATT | AAA | CTC | TCA | CCT | CCC | ATG | TTG | CTC | 387 |
| Leu | Cys | Val | Leu | Asp | Tyr | Phe | Ile | Lys | Leu | Ser | Pro | Pro | Met | Leu | Leu | |
| | | 110 | | | | | 115 | | | | | 120 | | | | |
| AAA | GAA | CCA | TAT | AAA | ACA | GCT | GTT | ATA | CCC | ATT | AAT | GGT | TCA | CCT | CGA | 435 |
| Lys | Glu | Pro | Tyr | Lys | Thr | Ala | Val | Ile | Pro | Ile | Asn | Gly | Ser | Pro | Arg | |
| | 125 | | | | | 130 | | | | | 135 | | | | | |
| ACA | CCC | AGG | CGA | GGT | CAG | AAC | AGG | AGT | GCA | CGG | ATA | GCA | AAA | CAA | CTA | 483 |
| Thr | Pro | Arg | Arg | Gly | Gln | Asn | Arg | Ser | Ala | Arg | Ile | Ala | Lys | Gln | Leu | |
| 140 | | | | | 145 | | | | | 150 | | | | | 155 | |
| GAA | AAT | GAT | ACA | AGA | ATT | ATT | GAA | GTT | CTC | TGT | AAA | GAA | CAT | GAA | TGT | 531 |
| Glu | Asn | Asp | Thr | Arg | Ile | Ile | Glu | Val | Leu | Cys | Lys | Glu | His | Glu | Cys | |
| | | | | 160 | | | | | 165 | | | | | 170 | | |
| AAT | ATA | GAT | GAG | GTG | AAA | AAT | GTT | TAT | TTC | AAA | AAT | TTT | ATA | CCT | TTT | 579 |
| Asn | Ile | Asp | Glu | Val | Lys | Asn | Val | Tyr | Phe | Lys | Asn | Phe | Ile | Pro | Phe | |
| | | | 175 | | | | | 180 | | | | | 185 | | | |
| ATG | AAT | TCT | CTT | GGA | CTT | GTA | ACA | TCT | AAT | GGA | CTT | CCA | GAG | GTT | GAA | 627 |
| Met | Asn | Ser | Leu | Gly | Leu | Val | Thr | Ser | Asn | Gly | Leu | Pro | Glu | Val | Glu | |
| | | 190 | | | | | 195 | | | | | 200 | | | | |
| AAT | CTT | TCT | AAA | CGA | TAC | GAA | GAA | ATT | TAT | CTT | AAA | AAT | AAA | GAT | CTA | 675 |
| Asn | Leu | Ser | Lys | Arg | Tyr | Glu | Glu | Ile | Tyr | Leu | Lys | Asn | Lys | Asp | Leu | |
| | 205 | | | | | 210 | | | | | 215 | | | | | |
| GAT | GCA | AGA | TTA | TTT | TTG | GAT | CAT | GAT | AAA | ACT | CTT | CAG | ACT | GAT | TCT | 723 |
| Asp | Ala | Arg | Leu | Phe | Leu | Asp | His | Asp | Lys | Thr | Leu | Gln | Thr | Asp | Ser | |
| 220 | | | | | 225 | | | | | 230 | | | | | 235 | |
| ATA | GAC | AGT | TTT | GAA | ACA | CAG | AGA | ACA | CCA | CGA | AAA | AGT | AAC | CTT | GAT | 771 |
| Ile | Asp | Ser | Phe | Glu | Thr | Gln | Arg | Thr | Pro | Arg | Lys | Ser | Asn | Leu | Asp | |
| | | | 240 | | | | | 245 | | | | | 250 | | | |
| GAA | GAG | GTG | AAT | GTA | ATT | CCT | CCA | CAC | ACT | CCA | GTT | AGG | ACT | GTT | ATG | 819 |
| Glu | Glu | Val | Asn | Val | Ile | Pro | Pro | His | Thr | Pro | Val | Arg | Thr | Val | Met | |
| | | | 255 | | | | | 260 | | | | | 265 | | | |
| AAC | ACT | ATC | CAA | CAA | TTA | ATG | ATG | ATT | TTA | AAT | TCA | GCA | AGT | GAT | CAA | 867 |
| Asn | Thr | Ile | Gln | Gln | Leu | Met | Met | Ile | Leu | Asn | Ser | Ala | Ser | Asp | Gln | |
| | | 270 | | | | | 275 | | | | | 280 | | | | |
| CCT | TCA | GAA | AAT | CTG | ATT | TCC | TAT | TTT | AAC | AAC | TGC | ACA | GTG | AAT | CCA | 915 |
| Pro | Ser | Glu | Asn | Leu | Ile | Ser | Tyr | Phe | Asn | Asn | Cys | Thr | Val | Asn | Pro | |
| | 285 | | | | | 290 | | | | | 295 | | | | | |
| AAA | GAA | AGT | ATA | CTG | AAA | AGA | GTG | AAG | GAT | ATA | GGA | TAC | ATC | TTT | AAA | 963 |
| Lys | Glu | Ser | Ile | Leu | Lys | Arg | Val | Lys | Asp | Ile | Gly | Tyr | Ile | Phe | Lys | |

-continued

| | | | | | | | | | | | | | | | | |
|---|---|---|---|---|---|---|---|---|---|---|---|---|---|---|---|---|
| 300 | | | | | 305 | | | | | 310 | | | | | 315 | |

| GAG | AAA | TTT | GCT | AAA | GCT | GTG | GGA | CAG | GGT | TGT | GTC | GAA | ATT | GGA | TCA | 1011 |
| Glu | Lys | Phe | Ala | Lys | Ala | Val | Gly | Gln | Gly | Cys | Val | Glu | Ile | Gly | Ser | |
| | | | | 320 | | | | | 325 | | | | | 330 | | |

| CAG | CGA | TAC | AAA | CTT | GGA | GTT | CGC | TTG | TAT | TAC | CGA | GTA | ATG | GAA | TCC | 1059 |
| Gln | Arg | Tyr | Lys | Leu | Gly | Val | Arg | Leu | Tyr | Tyr | Arg | Val | Met | Glu | Ser | |
| | | | | 335 | | | | | 340 | | | | | 345 | | |

| ATG | CTT | AAA | TCA | GAA | GAA | GAA | CGA | TTA | TCC | ATT | CAA | AAT | TTT | AGC | AAA | 1107 |
| Met | Leu | Lys | Ser | Glu | Glu | Glu | Arg | Leu | Ser | Ile | Gln | Asn | Phe | Ser | Lys | |
| | | 350 | | | | | 355 | | | | | 360 | | | | |

| CTT | CTG | AAT | GAC | AAC | ATT | TTT | CAT | ATG | TCT | TTA | TTG | GCG | TGC | GCT | CTT | 1155 |
| Leu | Leu | Asn | Asp | Asn | Ile | Phe | His | Met | Ser | Leu | Leu | Ala | Cys | Ala | Leu | |
| | 365 | | | | | 370 | | | | | 375 | | | | | |

| GAG | GTT | GTA | ATG | GCC | ACA | TAT | AGC | AGA | AGT | ACA | TCT | CAG | AAT | CTT | GAT | 1203 |
| Glu | Val | Val | Met | Ala | Thr | Tyr | Ser | Arg | Ser | Thr | Ser | Gln | Asn | Leu | Asp | |
| 380 | | | | | 385 | | | | | 390 | | | | | 395 | |

| TCT | GGA | ACA | GAT | TTG | TCT | TTC | CCA | TGG | ATT | CTG | AAT | GTG | CTT | AAT | TTA | 1251 |
| Ser | Gly | Thr | Asp | Leu | Ser | Phe | Pro | Trp | Ile | Leu | Asn | Val | Leu | Asn | Leu | |
| | | | | 400 | | | | | 405 | | | | | 410 | | |

| AAA | GCC | TTT | GAT | TTT | TAC | AAA | GTG | ATC | GAA | AGT | TTT | ATC | AAA | GCA | GAA | 1299 |
| Lys | Ala | Phe | Asp | Phe | Tyr | Lys | Val | Ile | Glu | Ser | Phe | Ile | Lys | Ala | Glu | |
| | | | 415 | | | | | 420 | | | | | 425 | | | |

| GGC | AAC | TTG | ACA | AGA | GAA | ATG | ATA | AAA | CAT | TTA | GAA | CGA | TGT | GAA | CAT | 1347 |
| Gly | Asn | Leu | Thr | Arg | Glu | Met | Ile | Lys | His | Leu | Glu | Arg | Cys | Glu | His | |
| | | 430 | | | | | 435 | | | | | 440 | | | | |

| CGA | ATC | ATG | GAA | TCC | CTT | GCA | TGG | CTC | TCA | GAT | TCA | CCT | TTA | TTT | GAT | 1395 |
| Arg | Ile | Met | Glu | Ser | Leu | Ala | Trp | Leu | Ser | Asp | Ser | Pro | Leu | Phe | Asp | |
| | | 445 | | | | | 450 | | | | | 455 | | | | |

| CTT | ATT | AAA | CAA | TCA | AAG | GAC | CGA | GAA | GGA | CCA | ACT | GAT | CAC | CTT | GAA | 1443 |
| Leu | Ile | Lys | Gln | Ser | Lys | Asp | Arg | Glu | Gly | Pro | Thr | Asp | His | Leu | Glu | |
| 460 | | | | | 465 | | | | | 470 | | | | | 475 | |

| TCT | GCT | TGT | CCT | CTT | AAT | CTT | CCT | CTC | CAG | AAT | AAT | CAC | ACT | GCA | GCA | 1491 |
| Ser | Ala | Cys | Pro | Leu | Asn | Leu | Pro | Leu | Gln | Asn | Asn | His | Thr | Ala | Ala | |
| | | | | 480 | | | | | 485 | | | | | 490 | | |

| GAT | ATG | TAT | CTT | TCT | CCT | GTA | AGA | TCT | CCA | AAG | AAA | AAA | GGT | TCA | ACT | 1539 |
| Asp | Met | Tyr | Leu | Ser | Pro | Val | Arg | Ser | Pro | Lys | Lys | Lys | Gly | Ser | Thr | |
| | | | | 495 | | | | 500 | | | | | 505 | | | |

| ACG | CGT | GTA | AAT | TCT | ACT | GCA | AAT | GCA | GAG | ACA | CAA | GCA | ACC | TCA | GCC | 1587 |
| Thr | Arg | Val | Asn | Ser | Thr | Ala | Asn | Ala | Glu | Thr | Gln | Ala | Thr | Ser | Ala | |
| | | 510 | | | | | 515 | | | | | 520 | | | | |

| TTC | CAG | ACC | CAG | AAG | CCA | TTG | AAA | TCT | ACC | TCT | CTT | TCA | CTG | TTT | TAT | 1635 |
| Phe | Gln | Thr | Gln | Lys | Pro | Leu | Lys | Ser | Thr | Ser | Leu | Ser | Leu | Phe | Tyr | |
| | | 525 | | | | | 530 | | | | | 535 | | | | |

| AAA | AAA | GTG | TAT | CGG | CTA | GCC | TAT | CTC | CGG | CTA | AAT | ACA | CTT | TGT | GAA | 1683 |
| Lys | Lys | Val | Tyr | Arg | Leu | Ala | Tyr | Leu | Arg | Leu | Asn | Thr | Leu | Cys | Glu | |
| 540 | | | | | 545 | | | | | 550 | | | | | 555 | |

| CGC | CTT | CTG | TCT | GAG | CAC | CCA | GAA | TTA | GAA | CAT | ATC | ATC | TGG | ACC | CTT | 1731 |
| Arg | Leu | Leu | Ser | Glu | His | Pro | Glu | Leu | Glu | His | Ile | Ile | Trp | Thr | Leu | |
| | | | | 560 | | | | | 565 | | | | | 570 | | |

| TTC | CAG | CAC | ACC | CTG | CAG | AAT | GAG | TAT | GAA | CTC | ATG | AGA | GAC | AGG | CAT | 1779 |
| Phe | Gln | His | Thr | Leu | Gln | Asn | Glu | Tyr | Glu | Leu | Met | Arg | Asp | Arg | His | |
| | | | 575 | | | | | 580 | | | | | 585 | | | |

| TTG | GAC | CAA | ATT | ATG | ATG | TGT | TCC | ATG | TAT | GGC | ATA | TGC | AAA | GTG | AAG | 1827 |
| Leu | Asp | Gln | Ile | Met | Met | Cys | Ser | Met | Tyr | Gly | Ile | Cys | Lys | Val | Lys | |
| | | 590 | | | | | 595 | | | | | 600 | | | | |

| AAT | ATA | GAC | CTT | AAA | TTC | AAA | ATC | ATT | GTA | ACA | GCA | TAC | AAG | GAT | CTT | 1875 |
| Asn | Ile | Asp | Leu | Lys | Phe | Lys | Ile | Ile | Val | Thr | Ala | Tyr | Lys | Asp | Leu | |
| | 605 | | | | | 610 | | | | | 615 | | | | | |

| CCT | CAT | GCT | GTT | CAG | GAG | ACA | TTC | AAA | CGT | GTT | TTG | ATC | AAA | GAA | GAG | 1923 |
| Pro | His | Ala | Val | Gln | Glu | Thr | Phe | Lys | Arg | Val | Leu | Ile | Lys | Glu | Glu | |

| | | | | | | | | | | | | | | | | |
|---|---|---|---|---|---|---|---|---|---|---|---|---|---|---|---|---|
| 620 | | | | | 625 | | | | | 630 | | | | | 635 | |
| GAG | TAT | GAT | TCT | ATT | ATA | GTA | TTC | TAT | AAC | TCG | GTC | TTC | ATG | CAG | AGA | 1971 |
| Glu | Tyr | Asp | Ser | Ile | Ile | Val | Phe | Tyr | Asn | Ser | Val | Phe | Met | Gln | Arg | |
| | | | | 640 | | | | 645 | | | | | | 650 | | |
| CTG | AAA | ACA | AAT | ATT | TTG | CAG | TAT | GCT | TCC | ACC | AGG | CCC | CCT | ACC | TTG | 2019 |
| Leu | Lys | Thr | Asn | Ile | Leu | Gln | Tyr | Ala | Ser | Thr | Arg | Pro | Pro | Thr | Leu | |
| | | | 655 | | | | | 660 | | | | | 665 | | | |
| TCA | CCA | ATA | CCT | CAC | ATT | CCT | CGA | AGC | CCT | TAC | AAG | TTT | CCT | AGT | TCA | 2067 |
| Ser | Pro | Ile | Pro | His | Ile | Pro | Arg | Ser | Pro | Tyr | Lys | Phe | Pro | Ser | Ser | |
| | | 670 | | | | | 675 | | | | | 680 | | | | |
| CCC | TTA | CGG | ATT | CCT | GGA | GGG | AAC | ATC | TAT | ATT | TCA | CCC | CTG | AAG | AGT | 2115 |
| Pro | Leu | Arg | Ile | Pro | Gly | Gly | Asn | Ile | Tyr | Ile | Ser | Pro | Leu | Lys | Ser | |
| | 685 | | | | | 690 | | | | | 695 | | | | | |
| CCA | TAT | AAA | ATT | TCA | GAA | GGT | CTG | CCA | ACA | CCA | ACA | AAA | ATG | ACT | CCA | 2163 |
| Pro | Tyr | Lys | Ile | Ser | Glu | Gly | Leu | Pro | Thr | Pro | Thr | Lys | Met | Thr | Pro | |
| 700 | | | | | 705 | | | | | 710 | | | | | 715 | |
| AGA | TCA | AGA | ATC | TTA | GTA | TCA | ATT | GGT | GAA | TCA | TTC | GGG | ACT | TCT | GAG | 2211 |
| Arg | Ser | Arg | Ile | Leu | Val | Ser | Ile | Gly | Glu | Ser | Phe | Gly | Thr | Ser | Glu | |
| | | | | 720 | | | | | 725 | | | | | 730 | | |
| AAG | TTC | CAG | AAA | ATA | AAT | CAG | ATG | GTA | TGT | AAC | AGC | GAC | CGT | GTG | CTC | 2259 |
| Lys | Phe | Gln | Lys | Ile | Asn | Gln | Met | Val | Cys | Asn | Ser | Asp | Arg | Val | Leu | |
| | | | 735 | | | | | 740 | | | | | 745 | | | |
| AAA | AGA | AGT | GCT | GAA | GGA | AGC | AAC | CCT | CCT | AAA | CCA | CTG | AAA | AAA | CTA | 2307 |
| Lys | Arg | Ser | Ala | Glu | Gly | Ser | Asn | Pro | Pro | Lys | Pro | Leu | Lys | Lys | Leu | |
| | | 750 | | | | | 755 | | | | | 760 | | | | |
| CGC | TTT | GAT | ATT | GAA | GGA | TCA | GAT | GAA | GCA | GAT | GGA | AGT | AAA | CAT | CTC | 2355 |
| Arg | Phe | Asp | Ile | Glu | Gly | Ser | Asp | Glu | Ala | Asp | Gly | Ser | Lys | His | Leu | |
| | 765 | | | | | 770 | | | | | 775 | | | | | |
| CCA | GGA | GAG | TCC | AAA | TTT | CAG | CAG | AAA | CTG | GCA | GAA | ATG | ACT | TCT | ACT | 2403 |
| Pro | Gly | Glu | Ser | Lys | Phe | Gln | Gln | Lys | Leu | Ala | Glu | Met | Thr | Ser | Thr | |
| 780 | | | | | 785 | | | | | 790 | | | | | 795 | |
| CGA | ACA | CGA | ATG | CAA | AAG | CAG | AAA | ATG | AAT | GAT | AGC | ATG | GAT | ACC | TCA | 2451 |
| Arg | Thr | Arg | Met | Gln | Lys | Gln | Lys | Met | Asn | Asp | Ser | Met | Asp | Thr | Ser | |
| | | | | 800 | | | | | 805 | | | | | 810 | | |
| AAC | AAG | GAA | GAG | AAA | TGAGGATCTC | AGGACCTTGG | TGGACACTGT | GTACACCTCT | | | | | | | | 2506 |
| Asn | Lys | Glu | Glu | Lys | | | | | | | | | | | | |
| | | | | 815 | | | | | | | | | | | | |

```
GGATTCATTG TCTCTCACAG ATGTGACTGT ATAACTTTCC CAGGTTCTGT TTATGGCCAC    2566
ATTTAATATC TTCAGCTCTT TTTGTGGATA TAAAATGTGC AGATGCAATT GTTTGGGTGA    2626
TTCCTAAGCC ACTTGAAATG TTAGTCATTG TTATTTATAC AAGATTGAAA ATCTTGTGTA    2686
AATCCTGCCA TTTAAAAAGT TGTAGCAGAT TGTTTCCTCT TCCAAAGTAA AATTGCTGTG    2746
CTTTATGGAT AGTAAGAATG GCCCTAGAGT GGGAGTCCTG ATAACCCAGG CCTGTCTGAC    2806
TACTTTGCCT TCTTTTGTAG CATATAGGTG ATGTTTGCTC TTGTTTTTAT TAATTTATAT    2866
GTATATTTTT TTAATTTAAC ATGAACACCC TTAGAAAATG TGTCCTATCT ATCATCCAAA    2926
TGCAATTTGA TTGACTGCCC ATTCACCAAA ATTATCCTGA ACTCTTCTGC AAAAATGGAT    2986
ATTATTAGAA ATTAGAAAAA AATTACTAAT TTTACACATT AGATTTATT TTACTATTGG    3046
AATCTGATAT ACTGTGTGCT TGTTTTATAA AATTTTGCTT TTAATTAAAT AAAAGCTGGA    3106
AGCAAAGTAT AACCATATGA TACTATCATA CTACTGAAAC AGATTTCATA CCTCAGAATG    3166
TAAAAGAACT TACTGATTAT TTTCTTCATC CAACTTATGT TTTTAAATGA GGATTATTGA    3226
TAGTGG                                                              3232
```

( 2 ) INFORMATION FOR SEQ ID NO:2:

( i ) SEQUENCE CHARACTERISTICS:

(A) LENGTH: 3232 base pairs
(B) TYPE: nucleic acid
(C) STRANDEDNESS: double
(D) TOPOLOGY: Not Relevant (ii) MOLECULE TYPE: DNA (xi) SEQUENCE DESCRIPTION: SEQ ID NO:2:

| | | | | | | |
|---|---|---|---|---|---|---|
| GATCCCACTA | TCAATAATCC | TCATTTAAAA | ACATAAGTTG | GATGAAGAAA | ATAATCAGTA | 60 |
| AGTTCTTTTA | CATTCTGAGG | TATGAAATCT | GTTTCAGTAG | TATGATAGTA | TCATATGGTT | 120 |
| ATACTTTGCT | TCCAGCTTTT | ATTTAATTAA | AAGCAAAATT | TTATAAAACA | AGCACACAGT | 180 |
| ATATCAGATT | CCAATAGTAA | AATAAAATCT | AATGTGTAAA | ATTAGTAATT | TTTTCTAAT | 240 |
| TTCTAATAAT | ATCCATTTTT | GCAGAAGAGT | TCAGGATAAT | TTTGGTGAAT | GGGCAGTCAA | 300 |
| TCAAATTGCA | TTTGGATGAT | AGATAGGACA | CATTTTCTAA | GGGTGTTCAT | GTTAAATTAA | 360 |
| AAAAATATAC | ATATAAATTA | ATAAAAACAA | GAGCAAACAT | CACCTATATG | CTACAAAAGA | 420 |
| AGGCAAAGTA | GTCAGACAGG | CCTGGGTTAT | CAGGACTCCC | ACTCTAGGGC | CATTCTTACT | 480 |
| ATCCATAAAG | CACAGCAATT | TTACTTTGGA | AGAGGAAACA | ATCTGCTACA | ACTTTTTAAA | 540 |
| TGGCAGGATT | TACACAAGAT | TTTCAATCTT | GTATAAATAA | CAATGACTAA | CATTTCAAGT | 600 |
| GGCTTAGGAA | TCACCCAAAC | AATTGCATCT | GCACATTTTA | TATCCACAAA | AAGAGCTGAA | 660 |
| GATATTAAAT | GTGGCCATAA | ACAGAACCTG | GAAAGTTAT | ACAGTCACAT | CTGTGAGAGA | 720 |
| CAATGAATCC | AGAGGTGTAC | ACAGTGTCCA | CCAAGGTCCT | GAGATCCTCA | TTTCTCTTCC | 780 |
| TTGTTGAGG | TATCCATGCT | ATCATTCATT | TTCTGCTTTT | GCATTCGTGT | TCGAGTAGAA | 840 |
| GTCATTTCTG | CCAGTTTCTG | CTGAAATTTG | GACTCTCCTG | GGAGATGTTT | ACTTCCATCT | 900 |
| GCTTCATCTG | ATCCTTCAAT | ATCAAAGCGT | AGTTTTTCA | GTGGTTTAGG | AGGGTTGCTT | 960 |
| CCTTCAGCAC | TTCTTTTGAG | CACACGGTCG | CTGTTACATA | CCATCTGATT | TATTTTCTGG | 1020 |
| AACTTCTCAG | AAGTCCCGAA | TGATTCACCA | ATTGATACTA | AGATTCTTGA | TCTTGGAGTC | 1080 |
| ATTTTTGTTG | GTGTTGGCAG | ACCTTCTGAA | ATTTTATATG | GACTCTTCAG | GGGTGAAATA | 1140 |
| TAGATGTTCC | CTCCAGGAAT | CCGTAAGGGT | GAACTAGGAA | ACTTGTAAGG | GCTTCGAGGA | 1200 |
| ATGTGAGGTA | TTGGTGACAA | GGTAGGGGGC | CTGGTGGAAG | CATACTGCAA | AATATTTGTT | 1260 |
| TTCAGTCTCT | GCATGAAGAC | CGAGTTATAG | AATACTATAA | TAGAATCATA | CTCCTCTTCT | 1320 |
| TTGATCAAAA | CACGTTTGAA | TGTCTCCTGA | ACAGCATGAG | GAAGATCCTT | GTATGCTGTT | 1380 |
| ACAATGATTT | TGAATTTAAG | GTCTATATTC | TTCACTTTGC | ATATGCCATA | CATGGAACAC | 1440 |
| ATCATAATTT | GGTCCAAATG | CCTGTCTCTC | ATGAGTTCAT | ACTCATTCTG | CAGGGTGTGC | 1500 |
| TGGAAAAGGG | TCCAGATGAT | ATGTTCTAAT | TCTGGGTGCT | CAGACAGAAG | GCGTTCACAA | 1560 |
| AGTGTATTTA | GCCGGAGATA | GGCTAGCCGA | TACACTTTTT | TATAAAACAG | TGAAAGAGAG | 1620 |
| GTAGATTTCA | ATGGCTTCTG | GGTCTGGAAG | GCTGAGGTTG | CTTGTGTCTC | TGCATTTGCA | 1680 |
| GTAGAATTTA | CACGCGTAGT | TGAACCTTTT | TTCTTTGGAG | ATCTTACAGG | AGAAAGATAC | 1740 |
| ATATCTGCTG | CAGTGTGATT | ATTCTGGAGA | GGAAGATTAA | GAGGACAAGC | AGATTCAAGG | 1800 |
| TGATCAGTTG | GTCCTTCTCG | GTCCTTTGAT | TGTTTAATAA | GATCAAATAA | AGGTGAATCT | 1860 |
| GAGAGCCATG | CAAGGGATTC | CATGATTCGA | TGTTCACATC | GTTCTAAATG | TTTTATCATT | 1920 |
| TCTCTTGTCA | AGTTGCCTTC | TGCTTTGATA | AACTTTCGA | TCACTTTGTA | AAAATCAAAG | 1980 |
| GCTTTTAAAT | TAAGCACATT | CAGAATCCAT | GGGAAAGACA | AATCTGTTCC | AGAATCAAGA | 2040 |
| TTCTGAGATG | TACTTCTGCT | ATATGTGGCC | ATTACAACCT | CAAGAGCGCA | CGCCAATAAA | 2100 |
| GACATATGAA | AAATGTTGTC | ATTCAGAAGT | TTGCTAAAAT | TTTGAATGGA | TAATCGTTCT | 2160 |

```
TCTTCTGATT  TAAGCATGGA  TTCCATTACT  CGGTAATACA  AGCGAACTCC  AAGTTTGTAT    2220

CGCTGTGATC  CAATTTCGAC  ACAACCCTGT  CCCACAGCTT  TAGCAAATTT  CTCTTTAAAG    2280

ATGTATCCTA  TATCCTTCAC  TCTTTTCAGT  ATACTTTCTT  TTGGATTCAC  TGTGCAGTTG    2340

TTAAAATAGG  AAATCAGATT  TTCTGAAGGT  TGATCACTTG  CTGAATTTAA  AATCATCATT    2400

AATTGTTGGA  TAGTGTTCAT  AACAGTCCTA  ACTGGAGTGT  GTGGAGGAAT  TACATTCACC    2460

TCTTCATCAA  GGTTACTTTT  TCGTGGTGTT  CTCTGTGTTT  CAAAACTGTC  TATAGAATCA    2520

GTCTGAAGAG  TTTTATCATG  ATCCAAAAAT  AATCTTGCAT  CTAGATCTTT  ATTTTAAGA     2580

TAAATTTCTT  CGTATCGTTT  AGAAAGATTT  TCAACCTCTG  GAAGTCCATT  AGATGTTACA    2640

AGTCCAAGAG  AATTCATAAA  AGGTATAAAA  TTTTGAAAT   AAACATTTTT  CACCTCATCT    2700

ATATTACATT  CATGTTCTTT  ACAGAGAACT  TCAATAATTC  TTGTATCATT  TTCTAGTTGT    2760

TTTGCTATCC  GTGCACTCCT  GTTCTGACCT  CGCCTGGGTG  TTCGAGGTGA  ACCATTAATG    2820

GGTATAACAG  CTGTTTTATA  TGGTTCTTTG  AGCAACATGG  GAGGTGAGAG  TTTAATAAAA    2880

TAGTCAAGGA  CACATAGCAT  TAACTGAAAT  GAAATCACCA  GATCATCTTC  CATTTGTAAT    2940

ACTTCCCCTT  TAGCTAATAA  AAATGTGATC  CAAGAAACTT  TTAGCACCAA  TGCAGAATTT    3000

ATTTCAGTAG  ATATCGAACT  GCTGGGTTGT  GTCAAATATA  TAAGTTCACA  TGTCCTTTCC    3060

AATTTGCTGA  AGAGTGCAAA  CAATACATCA  TACTTCTTCA  ACAGTCTTGA  CATAGCATTA    3120

TCAACTTTGG  TACTGGTATC  AATTTCTTTT  AGTAAGTTAA  AGAATTTATG  GACACTGATT    3180

TCTATGTTTT  TCTGTAGCTC  AGTAAAAGTG  AACGACATCT  CATCTAGGTC  GG            3232
```

( 2 ) INFORMATION FOR SEQ ID NO:3:

( i ) SEQUENCE CHARACTERISTICS:
        ( A ) LENGTH: 816 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
Met  Ser  Phe  Thr  Phe  Thr  Glu  Leu  Gln  Lys  Asn  Ile  Glu  Ile  Ser  Val
 1              5                        10                       15

His  Lys  Phe  Phe  Asn  Leu  Leu  Lys  Glu  Ile  Asp  Thr  Ser  Thr  Lys  Val
              20                        25                       30

Asp  Asn  Ala  Met  Ser  Arg  Leu  Leu  Lys  Lys  Tyr  Asp  Val  Leu  Phe  Ala
         35                        40                       45

Leu  Phe  Ser  Lys  Leu  Glu  Arg  Thr  Cys  Glu  Leu  Ile  Tyr  Leu  Thr  Gln
     50                       55                       60

Pro  Ser  Ser  Ser  Ile  Ser  Thr  Glu  Ile  Asn  Ser  Ala  Leu  Val  Leu  Lys
 65                      70                       75                       80

Val  Ser  Trp  Ile  Thr  Phe  Leu  Leu  Ala  Lys  Gly  Glu  Val  Leu  Gln  Met
                   85                       90                       95

Glu  Asp  Asp  Leu  Val  Ile  Ser  Phe  Gln  Leu  Met  Leu  Cys  Val  Leu  Asp
              100                       105                      110

Tyr  Phe  Ile  Lys  Leu  Ser  Pro  Pro  Met  Leu  Leu  Lys  Glu  Pro  Tyr  Lys
         115                       120                      125

Thr  Ala  Val  Ile  Pro  Ile  Asn  Gly  Ser  Pro  Arg  Thr  Pro  Arg  Arg  Gly
     130                      135                      140

Gln  Asn  Arg  Ser  Ala  Arg  Ile  Ala  Lys  Gln  Leu  Glu  Asn  Asp  Thr  Arg
145                      150                      155                      160

Ile  Ile  Glu  Val  Leu  Cys  Lys  Glu  His  Glu  Cys  Asn  Ile  Asp  Glu  Val
```

-continued

```
                          165                         170                         175
Lys Asn Val Tyr Phe Lys Asn Phe Ile Pro Phe Met Asn Ser Leu Gly
                180                     185                     190

Leu Val Thr Ser Asn Gly Leu Pro Glu Val Glu Asn Leu Ser Lys Arg
        195                     200                     205

Tyr Glu Glu Ile Tyr Leu Lys Asn Lys Asp Leu Asp Ala Arg Leu Phe
        210                     215                     220

Leu Asp His Asp Lys Thr Leu Gln Thr Asp Ser Ile Asp Ser Phe Glu
225                     230                     235                     240

Thr Gln Arg Thr Pro Arg Lys Ser Asn Leu Asp Glu Glu Val Asn Val
                245                     250                     255

Ile Pro Pro His Thr Pro Val Arg Thr Val Met Asn Thr Ile Gln Gln
                260                     265                     270

Leu Met Met Ile Leu Asn Ser Ala Ser Asp Gln Pro Ser Glu Asn Leu
        275                     280                     285

Ile Ser Tyr Phe Asn Asn Cys Thr Val Asn Pro Lys Glu Ser Ile Leu
        290                     295                     300

Lys Arg Val Lys Asp Ile Gly Tyr Ile Phe Lys Glu Lys Phe Ala Lys
305                     310                     315                     320

Ala Val Gly Gln Gly Cys Val Glu Ile Gly Ser Gln Arg Tyr Lys Leu
                325                     330                     335

Gly Val Arg Leu Tyr Tyr Arg Val Met Glu Ser Met Leu Lys Ser Glu
                340                     345                     350

Glu Glu Arg Leu Ser Ile Gln Asn Phe Ser Lys Leu Leu Asn Asp Asn
        355                     360                     365

Ile Phe His Met Ser Leu Leu Ala Cys Ala Leu Glu Val Val Met Ala
        370                     375                     380

Thr Tyr Ser Arg Ser Thr Ser Gln Asn Leu Asp Ser Gly Thr Asp Leu
385                     390                     395                     400

Ser Phe Pro Trp Ile Leu Asn Val Leu Asn Leu Lys Ala Phe Asp Phe
                405                     410                     415

Tyr Lys Val Ile Glu Ser Phe Ile Lys Ala Glu Gly Asn Leu Thr Arg
                420                     425                     430

Glu Met Ile Lys His Leu Glu Arg Cys Glu His Arg Ile Met Glu Ser
        435                     440                     445

Leu Ala Trp Leu Ser Asp Ser Pro Leu Phe Asp Leu Ile Lys Gln Ser
        450                     455                     460

Lys Asp Arg Glu Gly Pro Thr Asp His Leu Glu Ser Ala Cys Pro Leu
465                     470                     475                     480

Asn Leu Pro Leu Gln Asn Asn His Thr Ala Ala Asp Met Tyr Leu Ser
                485                     490                     495

Pro Val Arg Ser Pro Lys Lys Lys Gly Ser Thr Thr Arg Val Asn Ser
                500                     505                     510

Thr Ala Asn Ala Glu Thr Gln Ala Thr Ser Ala Phe Gln Thr Gln Lys
        515                     520                     525

Pro Leu Lys Ser Thr Ser Leu Ser Leu Phe Tyr Lys Lys Val Tyr Arg
        530                     535                     540

Leu Ala Tyr Leu Arg Leu Asn Thr Leu Cys Glu Arg Leu Leu Ser Glu
545                     550                     555                     560

His Pro Glu Leu Glu His Ile Ile Trp Thr Leu Phe Gln His Thr Leu
                565                     570                     575

Gln Asn Glu Tyr Glu Leu Met Arg Asp Arg His Leu Asp Gln Ile Met
                580                     585                     590
```

| | | | | | | | | | | | | | |
|---|---|---|---|---|---|---|---|---|---|---|---|---|---|
| Met | Cys | Ser 595 | Met | Tyr | Gly | Ile | Cys 600 | Lys | Val | Lys | Asn | Ile 605 | Asp | Leu | Lys |
| Phe | Lys 610 | Ile | Ile | Val | Thr | Ala 615 | Tyr | Lys | Asp | Leu | Pro 620 | His | Ala | Val | Gln |
| Glu 625 | Thr | Phe | Lys | Arg | Val 630 | Leu | Ile | Lys | Glu | Glu 635 | Glu | Tyr | Asp | Ser | Ile 640 |
| Ile | Val | Phe | Tyr | Asn 645 | Ser | Val | Phe | Met | Gln 650 | Arg | Leu | Lys | Thr | Asn 655 | Ile |
| Leu | Gln | Tyr | Ala 660 | Ser | Thr | Arg | Pro | Pro 665 | Thr | Leu | Ser | Pro | Ile 670 | Pro | His |
| Ile | Pro | Arg 675 | Ser | Pro | Tyr | Lys | Phe 680 | Pro | Ser | Ser | Pro | Leu 685 | Arg | Ile | Pro |
| Gly | Gly 690 | Asn | Ile | Tyr | Ile | Ser 695 | Pro | Leu | Lys | Ser | Pro 700 | Tyr | Lys | Ile | Ser |
| Glu 705 | Gly | Leu | Pro | Thr | Pro 710 | Thr | Lys | Met | Thr | Pro 715 | Arg | Ser | Arg | Ile | Leu 720 |
| Val | Ser | Ile | Gly | Glu 725 | Ser | Phe | Gly | Thr | Ser 730 | Glu | Lys | Phe | Gln | Lys 735 | Ile |
| Asn | Gln | Met | Val 740 | Cys | Asn | Ser | Asp | Arg 745 | Val | Leu | Lys | Arg | Ser 750 | Ala | Glu |
| Gly | Ser | Asn 755 | Pro | Pro | Lys | Pro | Leu 760 | Lys | Lys | Leu | Arg | Phe 765 | Asp | Ile | Glu |
| Gly | Ser 770 | Asp | Glu | Ala | Asp | Gly 775 | Ser | Lys | His | Leu | Pro 780 | Gly | Glu | Ser | Lys |
| Phe 785 | Gln | Gln | Lys | Leu | Ala 790 | Glu | Met | Thr | Ser | Thr 795 | Arg | Thr | Arg | Met | Gln 800 |
| Lys | Gln | Lys | Met | Asn 805 | Asp | Ser | Met | Asp | Thr 810 | Ser | Asn | Lys | Glu | Glu 815 | Lys |

BROAD-SPECTRUM TUMOR SUPPRESSOR GENES, GENE PRODUCTS AND METHODS FOR TUMOR SUPPRESSOR GENE THERAPY

This invention was made in part with United States government support under grant number EY06195 awarded by National Institutes of Health. The United States government has certain rights in the invention.

BACKGROUND OF THE INVENTION

1.1 Field of the Invention

This invention is in the field of tumor suppressor genes (anti-oncogenes) and relates in general to products and methods for practicing broad-spectrum tumor suppressor gene therapy of various human cancers. In particular, the invention relates to methods for treating tumor cells (1) administering vectors comprising a nucleic acid sequence coding for a second in-frame AUG codon-initiated retinoblastoma protein of about 94 kD or (2) administering an effective amount of a protein coded for by the nucleic acid sequence.

1.2 Cancer

Cancers and tumors are the second most prevalent cause of death in the United States, causing 450,000 deaths per year. One in three Americans will develop cancer, and one in five will die of cancer (Scientific American Medicine, part 12, I, 1, section dated 1987). While substantial progress has been made in identifying some of the likely environmental and hereditary causes of cancer, the statistics for the cancer death rate indicates a need for substantial improvement in the therapy for cancer and related diseases and disorders.

1.3. Cancer Genes

A number of so-called cancer genes, i.e., genes that have been implicated in the etiology of cancer, have been identified in connection with hereditary forms of cancer and in a large number of well-studied tumor cells. Study of cancer genes has helped provide some understanding of the process of tumorigenesis. While a great deal more remains to be learned about cancer genes, the presently known cancer genes serve as useful models for understanding tumorigenesis.

Cancer genes are broadly classified into "oncogenes" which, when activated, promote tumorigenesis, and "tumor suppressor genes" which, when damaged, fail to suppress tumorigenesis. While these classifications provide a useful method for conceptualizing tumorigenesis, it is also possible that a particular gene may play differing roles depending upon the particular allelic form of that gene, its regulatory elements, the genetic background and the tissue environment in which it is operating.

1.3.1. Oncogenes

The oncogenes are somatic cell genes that are mutated from their wild-type alleles (the art refers to these wild-type alleles as protooncogenes) into forms which are able to induce tumorigenesis under certain conditions. There is presently a substantial literature on known and putative oncogenes and the various alleles of these oncogenes. In order to provide background information and to further the understanding of the scope of the invention, a brief discussion of representative oncogenes is provided.

For example, the oncogenes ras and myc are considered as models for understanding oncogenic processes in general. The ras oncogene is believed to encode a cytoplasmic protein, and the myc oncogene is believed to encode a nuclear protein. Neither the ras oncogene nor the myc oncogene alone is able to induce full transformation of a normal cell into a tumor cell, but full tumorigenesis usually occurs when both the ras and myc oncogenes are present and expressed together in the same cell (Weinberg, R. A., 1989, *Cancer Research* 49:3713–3721, at page 3713). Such collaborative effects have been observed between a number of other studied oncogenes.

The collaborative model of oncogene tumorigenesis must be qualified by the observation that a cell expressing the ras oncogene that is surrounded by normal cells does not undergo full transformation. However, if most of the surrounding cells are also ras-expressing, then the ras oncogene alone is sufficient to induce tumorigenesis in a ras-expressing cell. This observation validates the multiple hit theory of tumorigenesis because a change in the tissue environment of the cell hosting the oncogene may be considered a second hit.

An alternative and equally valid hypothesis is that events that collaborate with the activation of an oncogene such as ras or myc may include the inactivation of a negative regulatory factor or factors (Weinberg, R. A., 1989, *Cancer Research* 49:3713–3721, at 3717; Goodrich, D. W. and Lee, W-H., 1992, *Nature* 360:177–179), i.e., a tumor suppressor protein.

1.3.2. Tumor Suppressor Genes

Tumor suppressor genes are genes that, in their wild-type alleles, express proteins that suppress abnormal cellular proliferation. When the gene coding for a tumor suppressor protein is mutated or deleted, the resulting mutant protein or the complete lack of tumor suppressor protein expression may fail to correctly regulate cellular proliferation, and abnormal cellular proliferation may take place, particularly if there is already existing damage to the cellular regulatory mechanism. A number of well-studied human tumors and tumor cell lines have been shown to have missing or nonfunctional tumor suppressor genes. Examples of tumor suppression genes include, but are not limited to, the retinoblastoma susceptibility gene or RB gene, the p53 gene, the deleted in colon carcinoma (DCC) gene and the neurofibromatosis type 1 (NF-1) tumor suppressor gene (Weinberg, R. A. *Science*, 1991, 254:1138–1146). Loss of function or inactivation of tumor suppressor genes may play a central role in the initiation and/or progression of a significant number of human cancers.

The list of putative tumor suppressor genes is large and growing. The following discussion of tumor suppressor genes is not intended to provide a complete review of all known and putative tumor suppressor genes, but is provided as background to indicate the state of the art and the problems to be overcome before the art is able to provide successful genetic therapy of diseases and disorders characterized by abnormally proliferating cells, e.g., tumor or cancer cells.

1.2.2.1. The Retinoblastoma Gene

The RB gene is one of the better studied tumor suppressor genes. The size of the RB gene complementary DNA (cDNA), about 4.7 Kb, permits ready manipulation of the gene, so that insertions of the RB gene have been made into a number of cell lines. The RB gene has been shown to be missing or defective in a majority of retinoblastomas, sarcomas of the soft tissues and bones, and in approximately 20 to 40 percent of breast, lung, prostate and bladder carcinomas (Lee, W-H., et al., PCT Publ. No. WO 90/05180, at pages 38 and 39; see also, Bookstein, R. and Lee, W-H., 1991, *Crit. Rev. Oncog.*, 2:211–217; Benedict, W. F. et al., *J. Clin. Invest.*, 1990, 85:988–993).

Based upon study of the isolated RB cDNA clone, the predicted RB gene product has 928 amino acids and an expected molecular weight of 106 kD (Lee et al., 1987, *Nature,* 329:642–645). The natural factor corresponding to the predicted RB gene expression product has been identified as a nuclear phosphoprotein having an apparent relative molecular mass (Mr) of 110–114 kD (Lee et al., 1987, *Nature,* 329:642–645) or 110–116 kD (Xu et al., 1989, *Oncogene* 4:807–812). Hence, the literature generally refers to the protein encoded by the RB gene as p110$^{RB}$. In this connection, it is noteworthy that measurement of apparent relative molecular mass by SDS-PAGE is frequently inaccurate owing to protein secondary structure. Therefore, the full length RB protein of 928 amino acids is also referred to as the 115 kD (Yokota et al., 1988, *Oncogene,* 3:471–475), or 105 kD (Whyte et al., 1988, *Nature,* 334:124–129) RB proteins. Various mutations of the RB gene are known. These are generally inactive. However, a 56 kD truncated RB protein, designated as p56$^{RB}$ that is considered to function in the same way as does p110$^{RB}$ retains activity (Goodrich et al., 1992, *Nature* 360:177–179).

On SDS-PAGE normal human cells show an RB protein pattern consisting of a lower sharp band with an Mr of 110 kD and a broader, more variable region above this band with an Mr ranging from 110 kD to 116 kD. The 110 kD band is the underphosphorylated RB protein, whereas the broader region represents the phosphorylated RB protein. The heterogeneity of the molecular mass results from a varying degree of phosphorylation (Xu et al., 1989, *Oncogene,* 4:807–812).

The RB protein shows cyclical changes in phosphorylation. Most RB protein is unphosphorylated during G1 phase, but most (perhaps all) RB molecules are phosphorylated in S and G2 phases (Xu et al., 1989, *Oncogene,* 4:807–812; DeCaprio et al., 1989, *Cell,* 58:1085–1095; Buchkovich et al., 1989, *Cell,* 58:1097–1105; Chen et al., 1989, *Cell,* 58:1193–1198; Mihara et al., 1989, *Science,* 246:1300–1303). Furthermore, only the underphosphorylated RB protein binds to SV40 large T antigen. Given that RB protein binding by large T antigen is probably important for the growth promoting effects of large T antigen, this suggests that the underphosphorylated RB protein is the active form of the RB protein, and the phosphorylated RB protein in S and G2 phases is inactive (Ludlow et al., 1989, *Cell,* 56:57–65).

The RB gene expressing the first in-frame AUG codon-initiated RB protein is also referred to herein as the intact RB gene, the RB$^{110}$ gene or the p110$^{RB}$ coding gene. It has also been observed that lower molecular weight (<100 kD, 98 kD, or 98–104 kD) bands of unknown origin which are immunoreactive to various anti-RB antibodies can be detected in immunoprecipitation and Western blots (Xu et al., 1989, *Oncogene,* 4:807–812; Furukawa et al., 1990, *Proc. Natl. Acad. Sci., USA,* 87:2770–2774; Stein et al., 1990, *Science,* 249:666–669).

Considering that the RB$^{110}$ cDNA open reading frame sequence (McGee, T. L., et al., 1989, *Gene,* 80:119–128) reveals an in-frame second AUG codon located at exon 3, nucleotides 355–357, the deduced second AUG codon-initiated RB protein would be 98 kD, or 12 kD smaller than the p110$^{RB}$ protein. It has been proposed that the lower molecular weight bands are the underphosphorylated (98 kD) and phosphorylated (98–104 kD) RB protein translated from the second AUG codon of the RB mRNA (Xu et al., 1989, *Oncogene,* 4:807–812), although no data directly supported this hypothesis. Thus, no conclusive observation confirms the actual expression of the RB gene from the second in-frame AUG codon. Further, Sections 4.2.1, and FIG. 5 infra provide data indicating the non-identity of the 98 kD protein bands of unknown origin and the second AUG codon-initiated protein products.

It has been proposed that introduction of a functional RB$^{110}$ gene into an RB-minus tumor cell will likely "normalize" the cell. Of course, it is not expected that tumor cells which already have normal RB$^{110}$ gene expression ("RB+") will respond to RB$^{110}$ gene therapy, because it is presumed that adding additional RB expression cannot correct a non-RB genetic defect. In fact, it has been shown that in the case of RB+ tumor cell lines, such as the osteosarcoma cell line, U-2 OS, which expresses the normal p110$^{RB}$, introduction of an extra p110$^{RB}$ coding gene did not change the neoplastic phenotype of such tumor lines (Huang, et al., 1988, *Science,* 242:1563–1566).

In the only reported exception, introduction of a p110$^{RB}$ coding vector into normal human fibroblasts, WS1, which have no known RB or any other genetic defects, led to the cessation of cell growth (WO 91/15580, Research Development Foundation, by Fung et al., PCT application filed 10 Apr. 1991, published 17 Oct. 1991, at page 18). However, it is believed that these findings were misinterpreted since a plasmid, ppVUO-Neo, producing SV40 T antigen with a well-known growth-promoting effect on host cells was used improperly to provide a comparison with the effect of RB$^{110}$ expression on cell growth of transfected WS1 fibroblasts (Fung, et al. Id. see Example 2 page 25). This view is confirmed by the extensive literature, together with similar confirming data provided by the examples presented infra, clearly characterizing RB+ tumor cells as "incurable" by treatment with wild-type RB$^{110}$ gene. In addition, it is noteworthy that the WS1 cell line per se is a generally recognized non-tumorigenic human diploid fibroblast cell line with limited cell division potential in culture. Therefore, WO91/15580 simply does not provide any method for effectively treating RB+ tumors with an RB$^{110}$ gene. Thus, there remains a need for a broad-spectrum tumor suppressor gene for treating abnormally proliferating cells having any type of genetic defect.

1.3.2.2. The Neurofibromatosis Gene

Neurofibromatosis type 1 or von Recklinghausen neurofibromatosis results from the inheritance of a predisposing mutant allele or from alleles created through new germline mutations (C. J. Marshall, 1991, *Cell,* 64:313–326). The neurofibromatosis type 1 gene, referred to as the NF1 gene, is a relatively large locus exhibiting a mutation rate of around $10^{-4}$. Defects in the NF1 gene result in a spectrum of clinical syndromes ranging from café-au-lait spots to neurofibromas of the skin and peripheral nerves to Schwannomas and neurofibrosarcomas.

The NF1 gene encodes a protein of about 2485 amino acids that shares structural similarity with three proteins that interact with the products of the ras protooncogene (Weinberg et al., 1991, *Science,* 254:1138–1146 at page 1141). For example, the NF1 amino acid sequence shows sequence homology to the catalytic domain of ras GAP, a GTPase-activating protein for p21 ras (C. J. Marshall, 1991, *Cell,* 64:313–326 at pages 320 and 321).

The role of NF1 in cell cycle regulation is apparently a complex one that is not yet fully elucidated. For example, it has been hypothesized that it is a suppressor of oncogenically activated p21 ras in yeast (C. J. Marshall, (1991, *Cell,* 64:313–326, bridging pages 320 and 321, and citing to Ballester et al, 1990, *Cell,* 63:851–859). On the other hand, other possible pathways for NF1 interaction are suggested by the available data (C. J. Marshall, 1991, *Cell,* 64:313–326 at page 321; Weinberg et al., 1991, *Science,* 254:1138–1146 at page 1141).

At present, no attempts to treat NF1 cells with a wild-type NF1 gene have been undertaken due to the size and complexity of the NF1 locus. Therefore, it would be highly desirable to have a broad-spectrum tumor suppressor gene able to treat NF1 and any other type of cancer or tumor.

1.3.3.3. The p53 Gene

Somatic cell mutations of the p53 gene are said to be the most frequently mutated gene in human cancer (Weinberg et al., 1991, *Science,* 254:1138–1146 at page 1143). The normal or wild-type p53 gene is a negative regulator of cell growth, which, when damaged, favors cell transformation (Weinberg et al. supra). As noted for the RB protein, the p53 expression product is found in the nucleus, where it may act in parallel with or cooperatively with $p110^{RB}$. This is suggested by a number of observations, for example, both p53 and $p110^{RB}$ proteins are targeted for binding or destruction by the oncoproteins of SV40, adenovirus and human papillomavirus.

Tumor cell lines deleted for p53 have been successfully treated with wild-type p53 vector to reduce tumorigenicity (Baker, S. J., et al., 1990, *Science,* 249:912–915). However, the introduction of either p53 or $RB^{110}$ into cells that have not undergone lesions at these loci does not affect cell proliferation (Marshall, C. J., 1991, *Cell,* 64:313–326 at page 321; Baker, S. J., et al., 1990, *Science,* 249:912–915; Huang, H.-J. S., et al., 1988 *Science,* 242:1563–1566). Such experiments suggest that sensitivity of cells to the suppression of their growth by a tumor suppressor gene is dependent on the genetic alterations that have taken place in the cells. Such a dependency would be further complicated by the observation in certain cancers that alterations in the p53 tumor suppressor or gene locus appear after mutational activation of the ras oncogene (Marshall, C. J., 1991, *Cell,* 64:313–326; Fearon, E. R., and Vogelstein, B., 1990, *Cell,* 61:759–767).

Therefore, there remains a need for a broad-spectrum tumor suppressor gene that does not depend on the specific identification of each mutated gene causing abnormal cellular proliferation.

1.3.3.4. The Deleted in Colon Carcinoma Gene (DCC)

The multiple steps in the tumorigenesis of colon cancer are readily monitored during development by colonoscopy. The combination of colonoscopy with the biopsy of the involved tissue has uncovered a number of degenerative genetic pathways leading to the result of a malignant tumor. One well studied pathway begins with large polyps of which 60% of the cells carry a mutated, activated allele of K-ras. A majority of these tumors then proceed to the inactivation-mutation of the gene referred to as the deleted in colon carcinoma (DCC) gene, followed by the inactivation of the p53 tumor suppressor gene.

The DCC gene is a more than approximately one million base pair gene coding for a 190-kD transmembrane phosphoprotein which is hypothesized to be a receptor (Weinberg et al., 1991, *Science,* 254:1138–1146 at page 1141), the loss of which allows the affected cell a growth advantage. It has also been noted that the DCC has partial sequence homology to the neural cell adhesion molecule (Marshall, 1991, *Cell,* 64:313–326) which might suggest a role for the DCC protogene in regulating cell to cell interactions.

As can be appreciated, the large size and complexity of the DCC gene, together with the complexity of the K-ras, p53 and possibly other genes involved in colon cancer tumorigenesis demonstrates a need for a broad-spectrum tumor suppressor gene and methods of treating colon carcinoma cells which do not depend upon manipulation of the DCC gene or on the identification of other specific damaged genes in colon carcinoma cells.

1.4 Genetic Therapy: Gene Transfer Methods

The treatment of human disease by gene transfer has now moved from the theoretical to the practical realm. The first human gene therapy trial was begun in September 1990 and involved transfer of the adenosine deaminase (ADA) gene into lymphocytes of a patient having an otherwise lethal defect in this enzyme, which produces immune deficiency. The results of this initial trial have been very encouraging and have helped to stimulate further clinical trials (Culver, K. W., Anderson, W. F., Blaese, R. M., *Hum. Gene. Ther.,* 1991, 2:107).

So far all but one of the approved gene transfer trials in humans rely on retroviral vectors for gene transduction. Retroviral vectors in this context are retroviruses from which all viral genes have been removed or altered so that no viral proteins are made in cells infected with the vector. Viral replication functions are provided by the use of retrovirus 'packaging' cells that produce all of the viral proteins but that do not produce infectious virus. Introduction of the retroviral vector DNA into packaging cells results in production of virions that carry vector RNA and can infect target cells, but no further virus spread occurs after infection. To distinguish this process from a natural virus infection where the virus continues to replicate and spread, the term transduction rather than infection is often used.

The major advantages of retroviral vectors for gene therapy are the high efficiency of gene transfer into replicating cells, the precise integration of the transferred genes into cellular DNA, and the lack of further spread of the sequences after gene transduction (Miller, A.D., *Nature,* 1992, 357:455–460).

The potential for production of replication-competent (helper) virus during the production of retroviral vectors remains a concern, although for practical purposes this problem has been solved. So far, all FDA-approved retroviral vectors have been made by using PA317 amphotropic retrovirus packaging cells (Miller, A.D., and Buttimore, C., *Molec. Cell Biol.,* 1986, 6:2895–2902). Use of vectors having little or no overlap with viral sequences in the PA317 cells eliminates helper virus production even by stringent assays that allow for amplification of such events (Lynch, C. M., and Miller, A. D., *J. Virol.,* 1991, 65:3887–3890). Other packaging cell lines are available. For example, cell lines designed for separating different retroviral coding regions onto different plasmids should reduce the possibility of helper virus production by recombination. Vectors produced by such packaging cell lines may also provide an efficient system for human gene therapy (Miller, A. D., 1992, *Nature,* 357:455–460).

Non-retroviral vectors have been considered for use in genetic therapy. One such alternative is the adenovirus (Rosenfeld, M. A., et al., 1992, *Cell,* 68:143–155; Jaffe, H. A. et al., 1992, *Nature Genetics* 1:372–378; Lemarchand, P. et al., 1992, *Proc. Natl. Acad. Sci. USA,* 89:6482–6486). Major advantages of adenovirus vectors are their potential to carry large segments of DNA (36 Kb genome), a very high titre ($10^{11}$ ml$^{-1}$), ability to infect non-replicating cells, and suitability for infecting tissues in situ, especially in the lung. The most striking use of this vector so far is to deliver a human cystic fibrosis transmembrane conductance regulator (CFTR) gene by intratracheal instillation to airway epithelium in cotton rats (Rosenfeld, M. A., et al., *Cell,* 1992, 63:143–155). Similarly, herpes viruses may also prove valuable for human gene therapy (Wolfe, J. H., et al., 1992,

*Nature Genetics*, 1:379–384). Of course, any other suitable viral vector may be used for genetic therapy with the present invention.

The other gene transfer method that has been approved by the FDA for use in humans is the transfer of plasmid DNA in liposomes directly to human cells in situ (Nabel, E. G., et al., 1990, *Science*, 249:1285– 1288). Plasmid DNA should be easy to certify for use in human gene therapy because, unlike retroviral vectors, it can be purified to homogeneity. In addition to liposome-mediated DNA transfer, several other physical DNA transfer methods such as those targeting the DNA to receptors on cells by complexing the plasmid DNA to proteins have shown promise in human gene therapy (Wu, G. Y., et al., 1991, *J. Biol. Chem.*, 266:14338–14342; Curiel, D. T., et al., 1991, *Proc. Natl. Acad. Sci. USA*, 88:8850–8854).

1.5 Proposed Strategies for Cancer Gene Therapy

It has been observed that certain tumor cells return to normal function when fused with normal cells, suggesting that replacement of a missing factor, such as a wild-type tumor suppressor gene expression product may serve to restore a tumor cell to a normal state (reviewed by Weinberg, R. A., 1989, *Cancer Research* 49:3713–3721, at 3717).

These observations have led to research aimed at providing genetic treatment of tumor cells having defective tumor suppressor genes. The proposed method of treatment requires identification of the damaged tumor suppressor gene, and introduction of the corresponding undamaged gene (including a promoter and a complete encoding sequence) into the affected tumor cells by means of a vector such as a retrovirus able to express the gene product. It is proposed that the incorporated functional gene will convert the target cell to a non-malignant state.

For example, The Regents of the University of California, in Patent Cooperation Treaty patent application (by Lee et al., number WO 90/05180, having an international filing date of 30 Oct. 1989 and published 17 May 1990), disclose a scheme for identifying an inactive or defective tumor suppressor gene and then replacing such a defective gene with its functional equivalent. In particular, the WO 90/05180 application proposes, based on in vitro studies, to insert a functional $RB^{110}$ gene into an RB-minus tumor cell by means of a retroviral vector in order to render such cells non-malignant.

In addition, international application WO 89/06703 (by Dryja et al., having an international filing date of 23 Jan. 1989, and published 27 Jul. 1989) proposes the treatment of retinoblastoma defective tumors by administering a retinoblastoma gene expression product.

In this connection, it has been reported that the introduction of the $RB^{110}$ gene into RB-minus retinoblastoma, osteosarcoma, bladder and prostate carcinoma cells resulted in cells showing reduced tumorigenicity in nude mice, but probably not a reduced cell growth rate. The results varied depending on the particular parental cell line (Goodrich et al., 1992, *Cancer Research* 52:1968–1973; Banerjee, A., et al., 1992, *Cancer Research*, 52:6297– 6304; Takahashi, R., et al., 1991, *Proc. Natl. Acad. Sci., USA*, 88:5257–5261; Xu, H-J., et al., 1991, *Cancer Research*, 51:4481–4485; Bookstein et al, 1990, *Science*, 247:712–715; Huang, H-J. S., et al., 1988, *Science* 242, 1563–1566). However, the suppression of tumorigenicity by introduction of the $p110^{RB}$ coding gene into RB-minus tumor cells is incomplete. The $p110^{RB}$ reconstituted tumor cells still form invasive tumors in nude mice (Xu, H-J., et al., 1991, *Cancer Research*, 51:4481–4485; Takahashi, R., et al., 1991, *Proc. Natl. Acad. Sci., USA*, 88:5257–5261; Banerjee, A., et al., 1992, *Cancer Research*, 52:6297–6304). In particular, it has been shown that $p110^{RB}$ reconstituted retinoblastoma cells inoculated into an orthotopic site (in this instance, the eye) consistently produced tumors (Xu, H-J., et al., 1991, *Cancer Research* 51:4481–4485). These findings, which will be discussed in detail infra, caution that the tumor suppressor gene replacement therapy as heretofore envisioned may simply result in cells that only appear to be "cured". Certainly, the findings of Xu et al. indicate a need for an improved genetic therapy for tumors which avoids these shortcomings.

Another proposed method of treating cancer by gene therapy is to antagonize the function of an oncogene by placing an artificial gene, constructed to have an inverted nucleotide sequence compared to the oncogene, into a tumor cell (U.S. Pat. No. 4,740,463, issued Apr. 26, 1988 by Weinberg, et al.).

All of these proposed solutions also share the deficiency of requiring that the specific genetic defect of the tumor to be treated be identified prior to treatment.

Since the $p110^{RB}$ protein product is active in the underphosphorylated state (discussed in detail supra), and phosphoamino acid analysis has demonstrated only phosphoserine and phosphothreonine but not phosphotyrosine in RB protein (Shew, J-Y., et al., 1989, *Ocogene Research*, 1:205–213), it has been proposed to make a mutant RB protein with its serine or threonine residues being replaced by alanine or valine or others and that introduction of such a mutant, unphosphorylated RB protein into target cells may lead to growth arrest (International Application WO 91/15580, Research Development Foundation, by Fung et al., at page 20). Unfortunately, in all cases analyzed so far, the human RB protein carrying a point mutation and retaining the unphosphorylated state were invariably inactive proteins and associated with tumorigenesis rather than tumor suppression (Templeton et al., 1991, *Proc. Natl. Acad. Sci., USA*, 88:3033– 3037.

1.6 Tumor Suppressor Gene Resistance

As the above discussion of gene mutations in tumor cells has indicated, not every cancer gene is a suitable candidate for wild-type gene replacement therapy due to the gene size or complexity or for other reasons. The retinoblastoma gene is one of those tumor suppressor genes that is readily accessible to study, thus it provides a model for understanding some of the other disadvantages to cancer gene replacement therapy as heretofore understood.

It is known that reintroduction of the retinoblastoma tumor suppressor gene into RB-defective tumor cells inhibits the tumor cell growth and suppresses the neoplastic phenotype of the target cells (WO 90/05180, cited supra; Huang et al., 1988, *Science*, 242:1563–1566; Bookstein et al., 1990, *Science*, 247:712–715; Xu et al., 1991, *Cancer Res.*, 51:4481–4485; Takahashi et al., 1991, *Proc. Natl. Acad. Sci., USA*, 88:5257–5261; Goodrich et al., 1992, *Cancer Res.*, 52:1968–1973; Banerjee et al., 1992, *Cancer Res.*, 52:6297–6304).

However, the suppression of tumorigenicity is often incomplete. A significant percentage of the RB-reconstituted tumor cells still form small tumors after a longer latency period in nude mouse tumorigenicity assays. Such tumors, although retaining normal RB expression, are histologically malignant and invasive (Xu et al., 1991, *Cancer Res.*, 51:4481–4485; Takahashi et al., 1991, *Proc. Natl. Acad. Sci., USA*, 88:5257–5261; Banerjee et al., 1992, *Cancer Res.*, 52:6297–6304).

Furthermore, it has been observed that several cell lines derived from such RB-positive tumors have become very tumorigenic and have formed large, progressively growing tumors when subsequently injected into nude mice (Zhou, Y.; Li, J.; Xu, K.; Hu, S-X.; Benedict, W. F., and Xu, H-J., *Proc. Am. Assoc. Cancer Res.*, 34:3214, 1993). This phenomenon, which is referred to herein as tumor suppressor gene resistance (TSGR) is a serious obstacle to the successful implementation of any scheme of tumor suppressor gene therapy for human cancers.

Without wishing to be bound by any particular hypothesis or explanation of the TSGR phenomenon, it is believed that the RB gene product exemplifies a possible explanation for TSGR. RB proteins have an active form (underphosphorylated protein) and an inactive form (phosphorylated protein). Therefore, RB-positive tumor cells may have inherited or acquired the ability to phosphorylate RB proteins to the inactive state and allow tumor cell proliferation to continue. Thus, conversion of RB-minus cells with plasmid or virus vectors coding for the $p110^{RB}$ protein provides only incomplete suppression, or even exacerbation of a percentage of the malignant cell population because the $p110^{RB}$ protein remains phosphorylated and inactive in some of the target cells.

Alternatively, the tumor cells expressing the $RB^{110}$ gene may simply have again inactivated the $RB^{110}$ gene by mutation in subsequent cell divisions (Lee et al., 1990, *Immunol. Ser.* 51:169–200, at page 188). Thus, there remains a need for a method of treating tumor cells by gene therapy so that the possibility of further mutation and resurgence of malignancy is avoided.

1.7 Summary of Obstacles to Cancer Gene Therapy

In brief, there are at least three major obstacles to be overcome to achieve a practical tumor suppressor gene therapy for tumor cells:

1) The necessity to determine the identity and sequence of each defective tumor suppressor gene or oncogene before attempting genetic therapy of that tumor. This is particularly a problem considering the multiple genetic defects found in many tumor cells studied;

2) The size and complexity of certain tumor suppressor genes or oncogenes renders manipulation of certain of these genes difficult; and 3) The possibility that TSGR as described above for the $RB^{110}$ model system will generate tumor cells that have equal or greater dysfunction than did the original abnormal cells.

Accordingly, there is a need in the art for a genetic therapy for tumor or cancer cells which can safely overcome these problems and provide an effective treatment for all types of tumor cells without the need to determine the exact genetic deficiency of each treated tumor cell and without the risk of TSGR resurgence and exacerbation of the malignancy.

2. SUMMARY OF THE INVENTION

Obstacles to the successful practice of tumor suppressor gene therapy of cancers are avoided by the present invention. In a totally unexpected and surprising discovery, it has been determined that the second in-frame AUG codon-initiated retinoblastoma suppressor protein of about 94 kD ($p94^{RB}$) is a broad-spectrum tumor suppressor, and that insertion of a gene capable of expressing this protein, or the protein itself, into an abnormally proliferating cell, such as a cancer or tumor cell, causes that cell to enter a senescent-like state, terminating the proliferation. The cell so-treated simply stops replicating and dies. The cell may possess any type of genetic defect, known or unknown, so that there is no need to determine the exact nature of the genetic defect associated with the abnormal proliferation. Further, the population of treated cells exhibits an unexpectedly much lower incidence of TSGR resurgence and exacerbation of malignancy than do cells treated with any other tumor suppressor gene. The method is repeated as needed.

Therefore, the invention provides $p94^{RB}$ encoding vectors and $p94^{RB}$ proteins for use in treatment of tumors or cancers, and methods of preparing $p94^{RB}$ proteins suitable for use in methods of treatment. The invention also provides methods of treatment for mammals such as humans, as well as methods of treating abnormally proliferating cells, such as cancer or tumor cells. Broadly, the invention contemplates treating abnormally proliferating cells, or mammals having a disease characterized by abnormally proliferating cells by any suitable method known to permit a host cell compatible $p94^{RB}$ encoding vector or a $p94^{RB}$ protein to enter the cells to be treated so that suppression of proliferation is achieved.

In one embodiment, the invention comprises a method of treating a disease characterized by abnormally proliferating cells, in a mammal, by administering an expression vector coding for $p94^{RB}$ to the mammal having a disease characterized by abnormally proliferating cells, inserting the expression vector into the abnormally proliferating cells, and expressing $p94^{RB}$ in the abnormally proliferating cells in an amount effective to suppress proliferation of those cells. The expression vector is inserted into the abnormally proliferating cells by viral infection or transduction, liposome-mediated transfection, polybrene-mediated transfection, CaPO4 mediated transfection and electroporation. The treatment is repeated as needed.

In another embodiment, the invention comprises a method of treating abnormally proliferating cells of a mammal by inserting a $p94^{RB}$ encoding expression vector into the abnormally proliferating cells and expressing $p94^{RB}$ therein in amounts effective to suppress proliferation of those cells. The treatment is repeated as needed.

In another alternative embodiment, the invention provides a DNA molecule able to suppress growth of an abnormally proliferating cell. The DNA molecule encodes a $p94^{RB}$ protein having an amino acid sequence substantially according to SEQ ID NO:3, provided that the DNA molecule does not also code for a $p110^{RB}$ protein. In a more preferred embodiment, the DNA molecule has the DNA sequence of SEQ ID NO:1, and is expressed by an expression vector. The expression vector may be any host cell-compatible vector. The vector is preferably selected from the group consisting of a retroviral vector, an adenoviral vector and a herpesviral vector.

In another alternative embodiment, the invention provides a $p94^{RB}$ protein having an amino acid sequence substantially according to SEQ ID NO:3.

In another alternative embodiment, the invention provides a method of producing a $p94^{RB}$ protein by the steps of: inserting a compatible expression vector comprising a $p94^{RB}$ encoding gene into a host cell and causing the host cell to express $p94^{RB}$ protein.

In another alternative embodiment, the invention comprises a method of treating abnormally proliferating cells of a mammal ex vivo by the steps of: removing a tissue sample in need of treatment from a mammal, the tissue sample comprising abnormally proliferating cells; contacting the tissue sample in need of treatment with an effective dose of an $p94^{RB}$ encoding expression vector; expressing the $p94^{RB}$ in the abnormally proliferating cells in amounts effective to suppress proliferation of the abnormally proliferating cells. The treatment is repeated as necessary; and the treated tissue sample is returned to the original or another mammal. Preferably, the tissue treated ex vivo is blood or bone marrow tissue.

In another alternative embodiment, the invention comprises a method of treating a disease characterized by abnormal cellular proliferation in a mammal by a process comprising the steps of administering $p94^{RB}$ protein to a mammal having a disease characterized by abnormally proliferating cells, such that the $p94^{RB}$ protein is inserted into the abnormally proliferating cells in amounts effective to suppress abnormal proliferation of the cells. In a preferred embodiment, the $p94^{RB}$ protein is liposome encapsulated for insertion into cells to be treated. The treatment is repeated as necessary.

In another alternative embodiment the invention comprises a method of treating abnormally proliferating cells of a mammal ex vivo by a process comprising the steps of removing a tissue sample in need of treatment from a mammal, the tissue sample comprising abnormally proliferating cells contacting the tissue sample in need of treatment with an effective dose of a $p94^{RB}$ protein. The treatment is repeated as necessary, and then the treated tissue is returned to the mammal or placed into another mammal.

In a more preferred embodiment the tumor or cancer cells to be treated are cells having one or more genetically defective tumor suppressor genes and oncogenes selected from the group consisting of an RB, a p53, a c-myc, an N-ras and a c-yes-1 gene.

In a more preferred embodiment the tumor or cancer cells are cells having no detectable genetic defect of a tumor suppressor gene selected from the group consisting of an RB gene and a p53 gene.

In a still more preferred embodiment the tumor or cancer cells are lung carcinoma cells.

In a still more preferred embodiment the $p94^{RB}$ encoding expression vector or the $p94^{RB}$ protein are administered by means of aerosol delivery of liposome-encapsulated $p94^{RB}$ encoding expression vector or $p94^{RB}$ protein into a lung in need of such treatment.

3. DETAILED DESCRIPTION OF THE INVENTION

3.1 Definitions

The terms "cancer" or "tumor" are clinically descriptive terms which encompass a myriad of diseases characterized by cells that exhibit unchecked and abnormal cellular proliferation The term "tumor", when applied to tissue, generally refers to any abnormal tissue growth, i.e., excessive and abnormal cellular proliferation. A tumor may be "benign" and unable to spread from its original focus, or "malignant" and capable of spreading beyond its anatomical site to other areas throughout the hostbody. The term "cancer" is an older term which is generally used to describe a malignant tumor or the disease state arising therefrom. Alternatively, the art refers to an abnormal growth as a neoplasm, and to a malignant abnormal growth as a malignant neoplasm.

Irrespective of whether the growth is classified as malignant or benign, the causes of excessive or abnormal cellular proliferation of tumor or cancer cells are not completely clear. Nevertheless, there is persuasive evidence that abnormal cellular proliferation is the result of a failure of one or more of the mechanisms controlling cell growth and division. It is also now believed that the mechanisms controlling cell growth and division include the genetic and tissue-mediated regulation of cell growth, mitosis and differentiation. These mechanisms are thought to act at the cell nucleus, the cell cytoplasm, the cell membrane and the tissue-specific environment of each cell. The process of transformation of a cell from a normal state to a condition of excessive or abnormal cellular proliferation is called tumorigenesis.

It has been observed that tumorigenesis is usually a multistep progression from a normal cellular state to, in some instances, a full malignancy. It is therefore believed that multiple "hits" upon the cell regulatory mechanisms are required for full malignancy to develop. Thus, in most instances, it is believed that there is no single cause of excessive proliferation, but that these disorders are the end result of a series of cumulative events.

While a malignant tumor or cancer capable of unchecked and rapid spread throughout the body is the most feared and usually the deadliest type of tumor, even so-called benign tumors or growths can cause significant morbidity and mortality by their inappropriate growth. A benign tumor can cause significant damage and disfigurement by inappropriate growth in cosmetically sensitive areas, or by exerting pressure on central or peripheral nervous tissue, blood vessels and other critical anatomical structures.

A broad-spectrum tumor suppressor gene is a genetic sequence coding for a protein that, when inserted into and expressed in an abnormally proliferating host cell, e.g., a tumor cell, suppresses abnormal proliferation of that cell irrespective of the cause of the abnormal proliferation. The second in-frame AUG (ATG in DNA) codon-initiated retinoblastoma gene disclosed herein exemplifies such a broad-spectrum tumor suppressor gene and is referred to herein as the $p94^{RB}$ coding gene, as the $RB^{94}$ gene or as a DNA molecule coding for $pRB^{94}$. According to the nucleotide sequence of the retinoblastoma susceptibility gene (McGee, T. L., et al., 1989, Gene, 80:119–128), the $p94^{RB}$ coding gene comprises the nucleotide sequence from exon 3, nucleotide 355 to exon 27, nucleotide 264. Thus, the $p94^{RB}$ encoding gene by definition excludes that portion of the $RB^{110}$ gene upstream from the second in-frame AUG start codon. FIG. 1 shows the DNA sequence of the $RB^{94}$ gene wherein the ATG codon begins at nucleotide 19 of that figure (SEQ ID NO:1; SEQ ID NO:2).

A broad-spectrum tumor suppressor protein (including phosphoproteins, lipoproteins, glycoproteins and other protein-based derivatives) is a substance that when injected into, absorbed by or caused to be expressed in any abnormally proliferating cell, reduces or completely suppresses abnormal cellular proliferation. The protein expressed by the second in-frame AUG codon-initiated retinoblastoma gene disclosed herein exemplifies such a broad-spectrum tumor suppressor protein. It is a phosphoprotein of about 94 kD relative molecular mass, and is also referred to herein as $p94^{RB}$ (SEQ ID NO:3).

One of ordinary skill in the art will be able to determine if any other fragment of a tumor suppressor protein, e.g., the third or fourth AUG codon-initiated retinoblastoma protein of about 90 kD and 83 kD, respectively, also has the property of suppressing abnormal cellular proliferation.

3.2 BRIEF DESCRIPTION OF THE FIGURES

FIG. 1: Nucleotide sequence of the cDNA fragment encoding the 94 kD therapeutic RB protein (plus strand is SEQ ID NO:1, minus strand is SEQ ID NO:2).

FIG. 2: Amino acid sequence of the 94 kDa therapeutic RB protein (SEQ ID NO:3).

FIG. 3: Construction of baculovirus expression vector for the 94 kDa therapeutic RB protein synthesis; *R.S. is recombination sequence. (nucleotides 5–24 of SEQ ID NO:1)

Figure 4B:
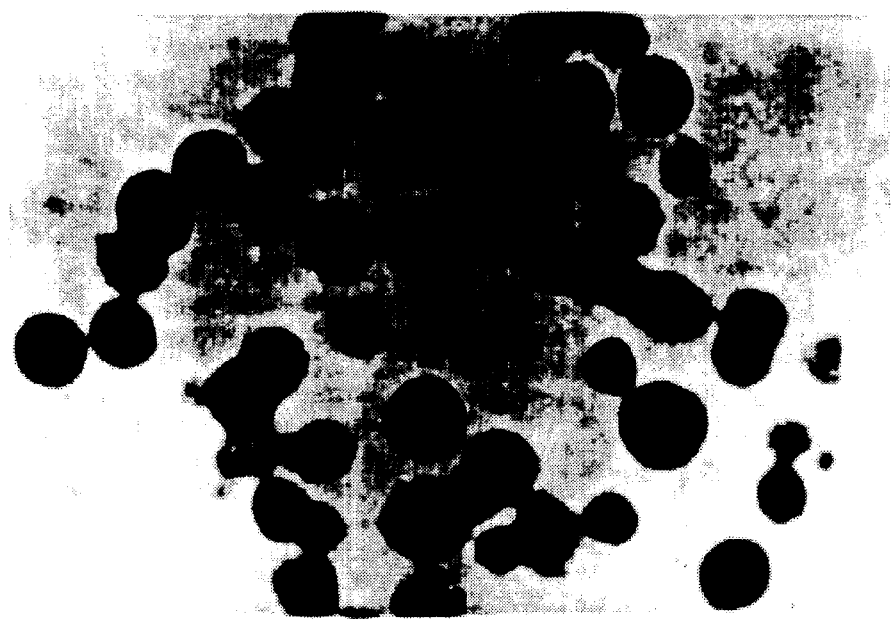
Figure 4A:
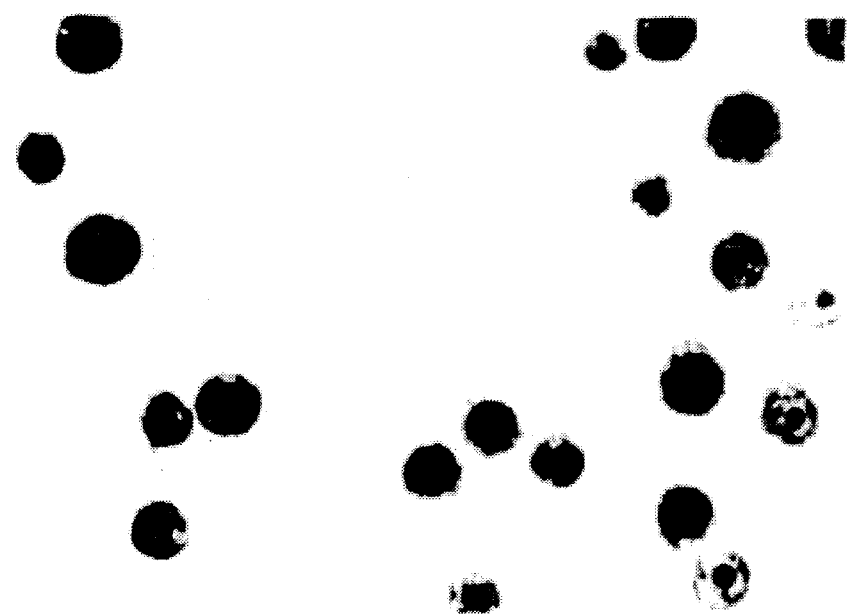
Figure 4C:
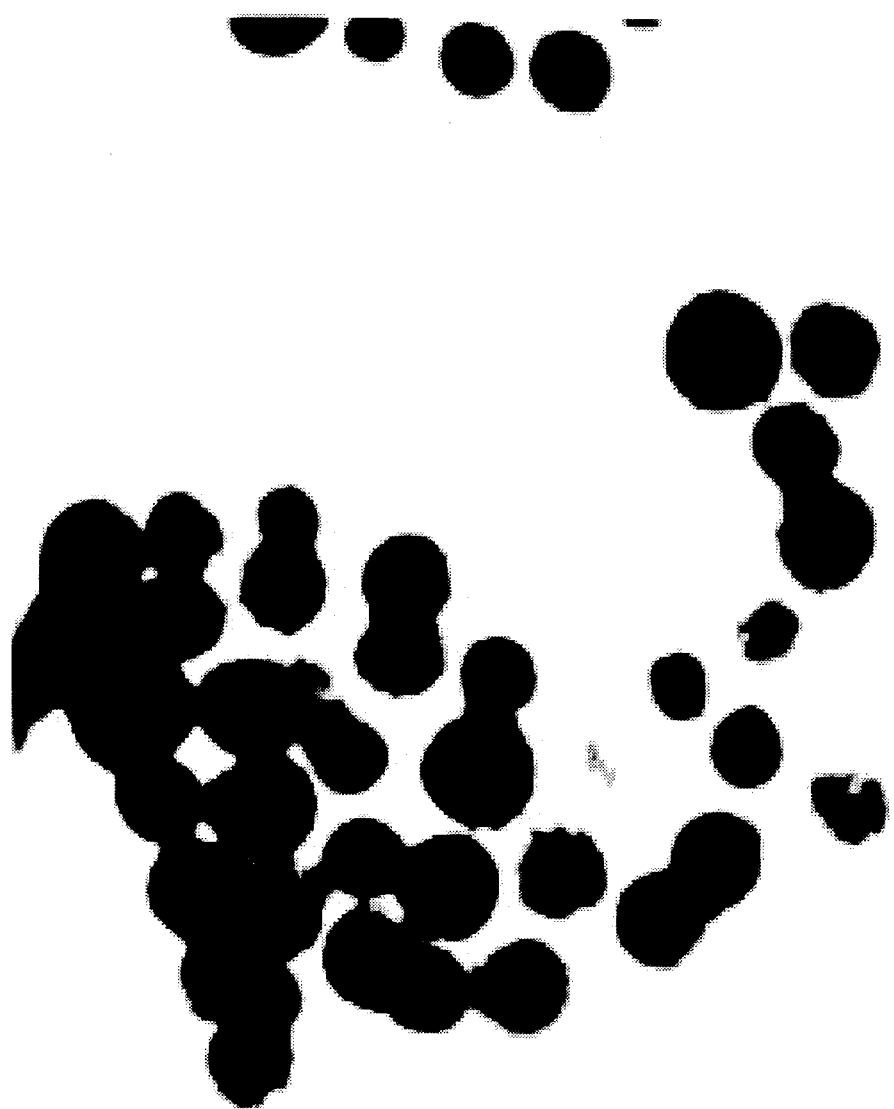

FIGS. 4A–4C: Intracellular localization of recombinant baculovirus-produced p110$^{RB}$ and p94$^{RB}$ in insect cells: panel A shows mock-infected Sf9 cells; panel B shows cells producing p110$^{RB}$; and panel C shows cells producing p94$^{RB}$; note that protein is localized to the nucleus in panels B and C. Protein localization is by anti-RB immunochemical staining.

Figure 5:
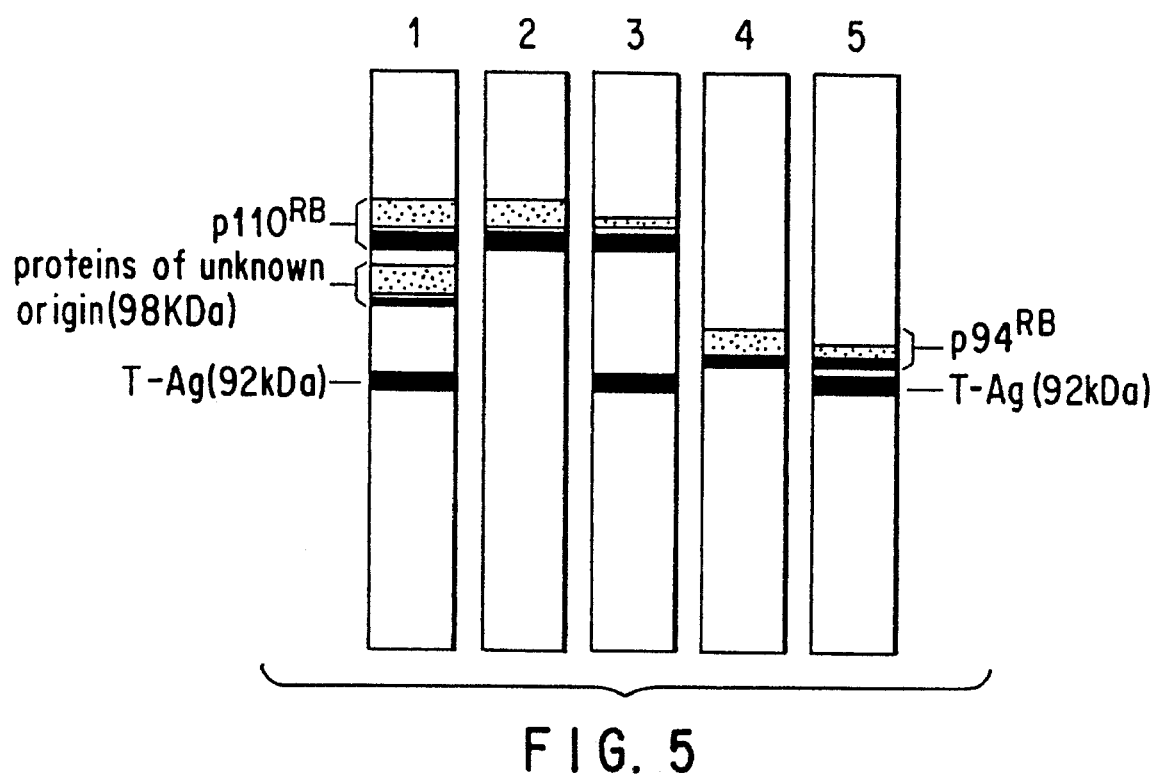

FIG. 5: A diagram of complex formation of baculovirus-expressed and subsequently purified p110$^{RB}$ and p94$^{RB}$ proteins with SV40 T antigen. The immunoaffinity chromatography purified proteins were mixed with an equal amount of T antigen, and aliquots of the mixture were immunoprecipitated with PAB419 anti-T antibody, followed by Western blotting. The blot was sequentially incubated with MAb-1 anti-RB antibody and PAB419 antibody. Lane 1, lysate of T antigen immortalized W138 VA13 fibrobrasts was used as a control; lane 2, purified p110$^{RB}$; lane 3, co-precipitation of T-Ag with p110$^{RB}$; lane 4 purified p94$^{RB}$ lane 5 co-precipitation of T-Ag with p94$^{RB}$.

FIG. 6: Construction of recombinant plasmids for high-level expression of p110$^{RB}$ (pCMV-f-RB35) and p94$^{RB}$ (pCMV-s-RB42) proteins in human cells using cytolomegalovirus promoter/enhancer: panel A is an explanatory drawing of the p110$^{RB}$ coding cDNA; panel B provides maps of the p110$^{RB}$ and p94$^{RB}$ expression plasmids where pCMV-f-RB35 codes for p110$^{RB}$ and pCMV-s-RB42 codes for p94$^{RB}$. Note that pCMV-s-RB42 has most of p110$^{RB}$ coding region deleted upstream of the second ATG.

FIG. 7: Construction of recombinant plasmids for expression of p110$^{RB}$ (pβA-f-RB33) and p94$^{RB}$ (pβA-s-RB34) proteins in human cells using β-actin promoter: panel A is a map of the p110$^{RB}$ coding plasmid, pβA-f-RB33; panel B is a map of the p94$^{RB}$ coding plasmid, pβA-s-RB34. Note that pβA-s-RB34 has most of the p110$^{RB}$ coding region deleted upstream of the second ATG.

Figure 8B:
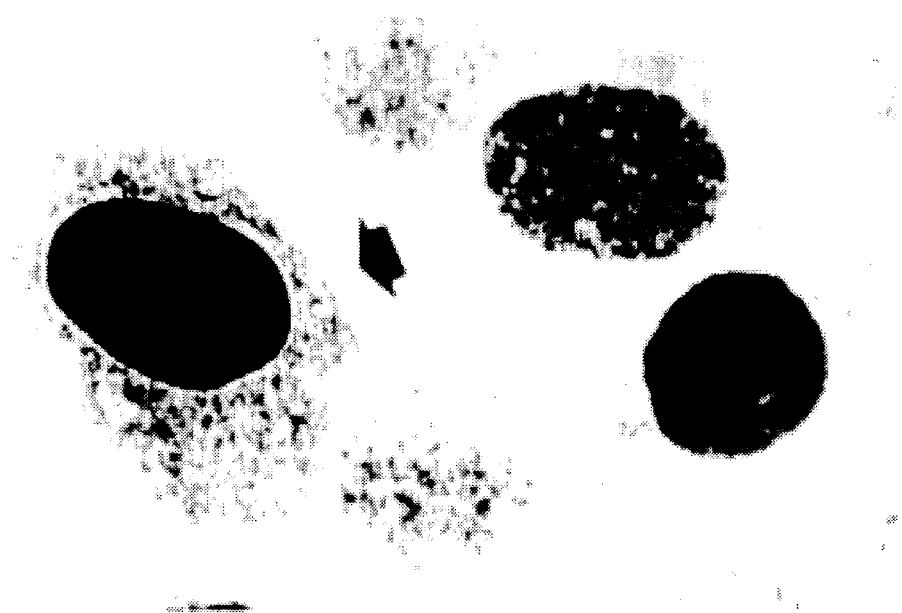
Figure 8A:
Figure 8C:

FIG. 8A–8C: Morphological effects of p110$^{RB}$ and p94$^{RB}$ expression on RB-defective bladder carcinoma cell line 5637 (ATCC HTB9): panel A is mock-transfected HTB9 cells; panel B is p110$^{RB}$ expressing HTB9 transfectants; panel C is p94$^{RB}$-expressing HTB9 transfectants. Arrows indicate examples for RB-positive immunostained cells. Note that the p110$^{RB}$ expressing cells of panel B appear normal, but that the p94$^{RB}$ expressing cells of panel C are senescent.

Figure 9:
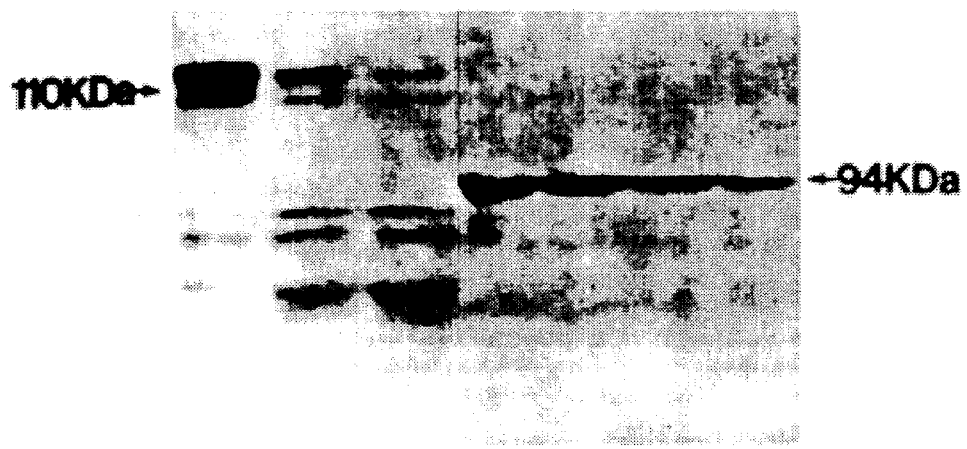

FIG. 9. Half-life analysis of p110$^{RB}$ and p94$^{RB}$ proteins in RB-reconstituted bladder carcinoma cell line, 5637. The bladder tumor cells were transfected in multiple dishes with either p110$^{RB}$ (pβA-f-RB33) or p94$^{RB}$ (pβA-s-RB34) expression plasmids. Twenty-four hours after transfection the cells were labeled with [$^{35}$S]-methionine and chased with excess unlabeled methionine for 0, 6, 12 and 24 hours, respectively. The p110$^{RB}$ and p94$^{RB}$ proteins were determined by immunoprecipitation: the left side of the figure (0–12 hours) shows the half-life of p110$^{RB}$ is less than 6 hours; the right side of the figure (0–24 hours) shows the half-life of p94$^{RB}$ is about 12 hours.

Figure 10:

FIG. 10. Western blot analysis of exogenous p110$^{RB}$ and p94$^{RB}$ proteins in transiently transfected 5637 cells showing the distinct underphosphorylation state of the p94$^{RB}$ protein: lane 1 shows normal human fibroblast cell line, WI-38; lane 2 shows parental RB-minus bladder carcinoma cell line, 5637; lane 3 shows 5637 cells transfected with p110$^{RB}$-expressing plasmid; lane 4 shows 5637 cells transfected with p94$^{RB}$-expressing plasmid.

3.3 THE INVENTION

The present invention is based upon the unexpected discovery that p94$^{RB}$ expressed by an expression vector in any abnormally proliferating target cell, e.g., a cancer or tumor cell, causes that suppressing the abnormal proliferation. Surprisingly, the treatment has been effective with all tested tumor cell lines and is not limited to treatment of RB-minus tumor cells.

Without wishing to be bound by a particular hypothesis or proposed mechanism of action, it is believed that the p94$^{RB}$ protein remains in the active, underphosphorylated form, and has a half-life in the target cell which is two to three times longer than that of p110$^{RB}$. Thus, it is possible that a synergistic combination of accumulation of p94$^{RB}$ together with its tendency to remain in an underphosphorylated, active form serves to terminate the cell replication cycle in target tumor cells. However, whatever the mechanism of action, the property of suppressing cell growth and inducing senescence or killing any abnormally proliferating cell, irrespective of its genetic defect, is nevertheless completely unanticipated and unexpected.

In order to obtain the broad-spectrum tumor suppressor protein, a gene coding for the second in-frame AUG codon-initiated RB protein, i e., p94$^{RB}$, was expressed by a baculovirus vector in insect host cells as a stable nuclear phosphoprotein. The resulting unphosphorylated forms of p94$^{RB}$ were able to form a specific complex with SV40 T antigen, providing an important verification that the p94$^{RB}$ protein shares many functional properties of the naturally occurred p110$^{RB}$ protein, i.e., phosphorylation, viral oncoprotein association and nuclear tethering (Templeton et al., 1991, *Proc. Natl. Acad. Sci., USA*, 88:3033–3037).

The effects of transfection by either first or second in-frame AUG codon-initiated RB protein expression plasmid were compared on a number of well known human tumor cell lines. The tested cell lines included: an RB-defective human bladder carcinoma cell line, 5637 (ATCC HTB9); RB-defective human breast carcinoma cell line, MDA-MB-468 (ATCC HTB132); RB-defective human non-small cell lung carcinoma cell line, H2009 (Kratzke, R. A., et al., 1992, *The Journal of Biological Chemistry*, 267:25998–26003); RB-defective human prostate carcinoma cell line, DU145 (ATCC HTB81); RB-defective human osteosarcoma cell line, Saos-2 (ATCC HTB85); RB-defective human fibrosarcoma metastatic to lung cell line, Hs913T (ATCC HTB152); human cervix adenocarcinoma cell line, HeLa (ATCC CCL2) and human fibrosarcoma cell line, HT1080 (ATCC CCL121). Both the HeLa and HT1080 cell lines have normal p110$^{RB}$ expression. Each of these cell lines were separately transfected with the p110$^{RB}$ coding and the p94$^{RB}$ coding expression plasmids. The results demonstrated that the second in-frame AUG codon-initiated RB protein, p94$^{RB}$, was a more effective cell growth inhibitor, causing those dividing tumor cells to senesce and die. On the other hand, most normal human cells in vivo are either non-dividing or have the potential to progress into the cell cycle after a long latency period. Therefore, p94$^{RB}$, as an active cell cycle regulatory factor and a therapeutic reagent is expected to show little or no toxicity when transiently expressed in normal cells in vivo.

The study also demonstrated that the RB-minus tumor cells expressing the second in-frame AUG codon-initiated RB protein, p94$^{RB}$, did not progress through the cell cycle, as evidenced by their failure to incorporate [$^3$H]-thymidine into DNA. However, the percentage of cells undergoing DNA replication was only slightly lower in cells producing the intact RB protein (p110$^{RB}$) than in cells that were RB-negative.

Of particular interest was the fact that the RB-defective bladder carcinoma cell line, 5637, failed to phosphorylate the second in-frame AUG codon-initiated RB protein as shown by Western blot analysis. In contrast, the intact RB protein (p110$^{RB}$) expressed in transfected 5637 cells were fully phosphorylated. Moreover, the half-life of the second in-frame AUG codon-initiated RB protein, p94$^{RB}$, was shown to be two-to three-fold greater than the intact RB protein (p110$^{RB}$). Therefore, the accumulation of only unphosphorylated (active) p94$^{RB}$ proteins may account for the failure of transiently transfected 5637 tumor cells to enter S phase, and this in turn may cause these tumor cells to senesce and die.

Both the fibrosarcoma cell line, HT1080 and cervix carcinoma cell line, HeLa, which have normal RB gene expression, were also successfully treated with the second in-frame AUG codon-initiated RB protein (p94$^{RB}$) expression plasmid, demonstrating that expression of the p94$^{RB}$ protein in RB+ cancer or tumor cells significantly suppressed the tumor cell growth. Therefore, an advantage of the present invention is that the methods and products herein disclosed can be used for therapeutic treating tumors having no specific tumor suppressor gene defects, which provides a significant advantage over previous techniques for human tumor suppressor gene therapy.

Table 1, on the following page, provides a summary of the identification of the tested tumor cell lines, their tumor origin and genetic defects.

used to construct p94$^{RB}$ encoding gene expression vectors consisting of appropriate transcriptional/translational control signals and the desired RB cDNA sequence downstream from the first in-frame AUG codon, that is unable to code for p110$^{RB}$. These methods may include in vitro DNA recombinant and synthetic techniques and in vivo genetic recombination. Expression of a nucleic acid sequence encoding a p94$^{RB}$ may be regulated by a second nucleic acid sequence so that the p94$^{RB}$ is expressed in a host infected or transfected with the recombinant DNA molecule. For example, expression of p94$^{RB}$ may be controlled by any promoter/enhancer element known in the art. The promoter activation may be tissue specific or inducible by a metabolic product or administered substance.

Promoters/enhancers which may be used to control p94$^{RB}$ gene expression include, but are not limited to, the native RB promoter, the cytomegalovirus (CMV) promoter/enhancer (Karasuyama, H., et al., 1989, *J. Exp. Med.*, 169:13), the human β-actin promoter (Gunning, P., et al., 1987, *Proc. Natl. Acad. Sci. USA*, 84:4831–4835), the glucocorticoid-inducible promoter present in the mouse mammary tumor virus long terminal repeat (MMTV LTR) (Klessig, D. F., et al., 1984, *Mol. Cell Biol.*, 4:1354–1362), the long terminal repeat sequences of Moloney murine leukemia virus (MuLV LTR) (Weiss, R., et al., 1985, *RNA Tumor Viruses*, Cold Spring Harbor Laboratory, Cold Spring Harbor, N. Y.), the SV40 early region promoter (Bernoist and Chambon, 1981, *Nature* 290:304–310), the promoter contained in the 3' long terminal repeat of Rous sarcoma virus (RSV) (Yamamoto et al., 1980, *Cell* 22:787–797), the herpes simplex virus (HSV) thymidine kinase promoter/enhancer (Wagner et al., 1981,

TABLE 1

The Status of Antioncogenes (Tumor Suppressor Genes) and Oncogenes in p94$^{RB}$-Treated Human Tumor Cells

| RECIPIENT CELLS | TUMOR ORIGIN | ANTI-ONCOGENES | | ONCOGENES |
|---|---|---|---|---|
| | | RB | p53 | |
| 5637 | Bladder carcinoma, primary tumor | Negative | Mutation | |
| DU145 | Prostate carcinoma, metastasis to brain | Point mutation | Mutation | |
| MDA-MB-468 | Breast Carcinoma | Large deletion | Mutation | |
| H2009 | Lung carcinoma | Mutation | Mutation | |
| Hs913T | Fibrosarcoma, metastasis to lung | Large deletion | Negative | |
| Saos2 | Osteosarcoma, primary tumor | Large deletion | Negative | |
| HeLa | Cervix carcinoma, primary tumor | Normal | Negative | c-myc activation[1] |
| HT1080 | Fibrosarcoma, primary tumor | Normal | Normal | N-ras and c-yes-1 activation[2,3] |

[1]Durst, M., et al. Papillomavirus sequences integrate near cellular oncogenes in some cervical carcinomas. Proc. Natl. Acad. Sci., USA, 84(4):1070–1074, 1987.
[2]Brown, R., et al. A mechanism of activation of an N-ras gene in the human fibrosarcoma cell line HT1080. EMBO J., 3:1321–1326, 1984.
[3]Sugawara, K., et al. Distribution of c-yes-1 gene product in various cells and tissues. Br. J. Cancer, 63(4):508–513, 1991.

3.3.1. Preparation of RB$^{94}$ Vectors
3.3.1.1. Therapeutic Vectors

Any of the methods known to the art for the insertion of DNA fragments into a vector, as described, for example, in Maniatis, T., Fritsch, E. F., and Sambrook, J. (1989): *Molecular Cloning (A Laboratory Manual)*, Cold Spring Harbor Laboratory, Cold Spring Harbor, N.Y.; and Ausubel, F. M., Brent, R., Kingston, R. E., Moore, D. D., Seidman, J. G., Smith, J. A., and Struhl, K. (1992): *Current Protocols in Molecular Biology*, John Wiley & Sons, New York, may be

*Proc. Natl. Acad. Sci. U.S.A.* 78:1441–1445), the regulatory sequences of the metallothionein gene (Brinster et al., 1982, *Nature* 296:39–42), the adenovirus promoter (Yamada et al., 1985, *Proc. Natl. Acad. Sci. U.S.A.* 82(11):3567–71), and the herpes simplex virus LAT promoter (Wolfe, J. H., et al., 1992, *Nature Genetics*, 1:379–384).

Expression vectors compatible with mammalian host cells for use in genetic therapy of tumor or cancer cells, include, but are not limited to: plasmids, retroviral vectors, adenovirus vectors, herpes viral vectors, and non-replicative avipox viruses, as disclosed, for example, by U.S. Pat. No. 5,174, 993.

In a specific embodiment, a plasmid vector derived from pHβeAPr-1-neo, was constructed for expression of $p94^{RB}$ in mammalian cells by placing the coding sequence for $p94^{RB}$ under control of the human β-actin gene promoter (Gunning, P. et al., *Proc. Natl. Acad. Sci., USA,* 1987, 84:4831–4835).

In another specific embodiment, a plasmid vector derived from pCMV-Neo-Bam (Baker, S. J., et al., *Science,* 1990, 249:912–915), was constructed for expression of $p94^{RB}$ in mammalian cells by placing the coding sequence for $p94^{RB}$ under control of the cytomegalovirus (CMV) promoter/enhancer sequences.

In another specific embodiment, a retroviral vector, pLL-RNL (Miller, A. D., et al., 1985, *Proc. Natl. Acad. Sci., USA,* 5:431) is used to construct a vector able to transduce mammalian cells and express $p94^{RB}$ protein under the control of the MuLV LTR promoter, the CMV promoter, the β-actin promoter or any other effective promoter.

In yet another specific embodiment, an adenovirus type 5 (Ad5) deletion mutant, Ad-dl324, and a plasmid, pTG5955 (Rosenfeld, M. A., et al., *Cell,* 1992, 68:143– 155) are used to construct an adenovirus vector able to infect mammalian cells and express $p94^{RB}$ protein under the control of the adenovirus type 2 (Ad2) major late promoter, the CMV promoter, the β-actin promoter or any other effective promoter.

3.3.1.2. Vectors for Production and Purification of $p94^{RB}$ Protein

Alternatively, expression vectors compatible with host cells suitable for production of $p94^{RB}$ may be constructed to express $p94^{RB}$ protein in those compatible host cells. These include but are not limited to mammalian cells infected with a virus (e.g., adenovirus, retrovirus, herpes simplex virus, avipox virus); insect cells infected with a virus (e.g., baculovirus); microorganisms such as yeasts containing yeast vectors, or bacteria transformed with bacteriophage DNA, plasmid DNA, or cosmid DNA. The expression controlling elements of vectors vary in their strengths and specifications. Depending on the host-vector system utilized, any one of a number of suitable transcription and translation elements may be used. The produced $p94^{RB}$ may be purified from host cells by affinity chromatography, electrophoresis, high-performance liquid chromatography (HPLC) or any other methods known to the art.

In a specific embodiment an engineered derivative of *Autographa california* Multiple Nuclear Polyhedrosis Virus ("AcMNPV") was used to produce $p94^{RB}$ protein in cultured Fall Army worm *Spondoptera frugiperda* cells (Sf9 cells) with a strong temporally regulated promoter of the polyhedron gene whose product represents 50% or more of total cellular proteins during a lytic infection. The baculovirus-expressed $p94^{RB}$ protein was subsequently purified by immunoaffinity chromatography.

3.3.1.3. Detection of $p94^{RB}$ Coding Expression Vectors

Expression vectors containing $p94^{RB}$ coding inserts can be identified by three general approaches: (a) nucleic acid hybridization, (b) presence or absence of "marker" gene functions, and (c) expression of inserted sequences. In the first approach, the presence of a $p94^{RB}$ coding gene inserted in an expression vector can be detected by nucleic acid hybridization using probes comprising sequences that are homologous/complementary to the inserted $p94^{RB}$ coding gene. Such hybridization can be carried out under stringent or nonstringent conditions, depending upon the size and sequence of the probe selected. In the second approach, the expression vector/host system can be identified and selected based upon the presence or absence of certain "marker" gene functions (e.g., thymidine kinase activity, resistance to antibiotics, viral occlusion formation in a baculovirus vector infected insect cell, etc.) caused by introduction of the expression vector into the host cell. For example, if the $p94^{RB}$ coding gene is inserted within a vector having a dominant selectable marker gene, such as a neomycin phosphotransferase gene under separate control of an appropriate promoter, such as an SV40 early promoter, the expression vector containing the $p94^{RB}$ coding gene can be identified by the presence of the marker gene function (geneticin resistance). In the third approach, expression vectors containing a $p94^{RB}$ coding gene can be identified by assaying the $p94^{RB}$ coding gene products expressed by the vectors. Such assays can be based, for example, on the physical or functional properties of the $p94^{RB}$ gene products in in vitro or in vivo assay systems including metabolic radiolabelling by [$^{35}$S] methionine, SDS-polyacrylamide gel electrophoresis, binding with a specific antibody, and phosphorylation by a protein kinase.

3.3.2. Expression of $p94^{RB}$

An appropriate $p94^{RB}$ coding expression vector, i.e., a vector which contains the necessary elements for the transcription and translation of the $p94^{RB}$ protein-coding sequence may be introduced into a host cell. A host cell may be any cell type compatible with the vector for expressing and producing $p94^{RB}$. In a preferred embodiment, the host cell is a mammalian tumor cell to be treated. In a more preferred embodiment, the host cell is a human tumor cell to be treated. Expression of the $p94^{RB}$ in a host cell may be transient, permanent, or inducible.

The necessary transcriptional and translational signals, including promoter/enhancer sequences can also be supplied by the native RB gene and/or its flanking regions. A variety of vector/host systems may be utilized to express the $p94^{RB}$ protein-coding sequence in a tumor cell to be treated. These include but are not limited to mammalian cell systems transfected, infected or transduced with a plasmid, or a virus (e.g., adenovirus, retrovirus, herpes simplex virus, avipox virus). The expression elements of vectors vary in their strengths and specificities. Depending on the host cell to be treated, any one or more of a number of suitable transcription and translation elements may be used.

3.3.3. Methods of Treatment

The $p94^{RB}$ encoding gene construct of the present invention may be placed by methods well known to the art into an expression vector such as a plasmid or viral expression vector. A plasmid expression vector may be introduced into a tumor cell by calcium phosphate transfection, liposome (for example, LIPOFECTIN)-mediated transfection, DEAE Dextran-mediated transfection, polybrene-mediated transfection, electroporation and any other method of introducing DNA into a cell.

A viral expression vector may be introduced into a target cell in an expressible form by infection or transduction. Such a viral vector includes, but is not limited to: a retrovirus, an adenovirus, a herpes virus and an avipox virus. When $p94^{RB}$ is expressed in any abnormally proliferating cell, the cell replication cycle is arrested, thereby resulting in senescence and cell death and ultimately, reduction in the mass of the abnormal tissue, i.e., the tumor or cancer. A vector able to introduce the gene construct into a target cell and able to express $p94^{RB}$ therein in cell proliferation-suppressing amounts can be administered by any effective method.

For example, a physiologically appropriate solution containing an effective concentration of active vectors can be administered topically, intraocularly, parenterally, orally, intranasally, intravenously, intramuscularly, subcutaneously or by any other effective means. In particular, the vector may be directly injected into a target cancer or tumor tissue by a needle in amounts effective to treat the tumor cells of the target tissue.

Alternatively, a cancer or tumor present in a body cavity such as in the eye, gastrointestinal tract, genitourinary tract (e.g., the urinary bladder), pulmonary and bronchial system and the like can receive a physiologically appropriate composition (e.g., a solution such as a saline or phosphate buffer, a suspension, or an emulsion, which is sterile except for the vector) containing an effective concentration of active vectors via direct injection with a needle or via a catheter or other delivery tube placed into the cancer or tumor afflicted hollow organ. Any effective imaging device such as X-ray, sonogram, or fiberoptic visualization system may be used to locate the target tissue and guide the needle or catheter tube.

In another alternative, a physiologically appropriate solution containing an effective concentration of active vectors can be administered systemically into the blood circulation to treat a cancer or tumor which cannot be directly reached or anatomically isolated.

In yet another alternative, target tumor or cancer cells can be treated by introducing $p94^{RB}$ protein into the cells by any known method. For example, liposomes are artificial membrane vesicles that are available to deliver drugs, proteins and plasmid vectors both in vitro or in vivo (Mannino, R. J. et al., 1988, *Biotechniques*, 6:682–690) into target cells (Newton, A. C. and Huestis, W. H., *Biochemistry*, 1988, 27:4655–4659; Tanswell, A. K. et al., 1990, *Biochmica et Biophysica Acta*, 1044:269–274; and Ceccoli, J. et al. *Journal of Investigative Dermatology*, 1989, 93:190–194). Thus, $p94^{RB}$ protein can be encapsulated at high efficiency with liposome vesicles and delivered into mammalian cells in vitro or in vivo.

Liposome-encapsulated $p94^{RB}$ protein may be administered topically, intraocularly, parenterally, intranasally, intratracheally, intrabronchially, intramuscularly, subcutaneously or by any other effective means at a dose efficacious to treat the abnormally proliferating cells of the target tissue. The liposomes may be administered in any physiologically appropriate composition containing an effective concentration of encapsulated $p94^{RB}$ protein.

3.3.4. Tumors Susceptible To Treatment

The gene construct and vectors of the present invention are effective in inhibiting the growth or mitosis or both of any type of tumor cell. The gene construct of the invention has demonstrated effectiveness in treating tumor cells of carcinomas and sarcomas. In particular, the gene construct of the invention has demonstrated effectiveness in suppressing replication and inducing cell senescence followed by cell death in the following tumor cell types: bladder carcinoma, lung carcinoma, breast carcinoma, prostate carcinoma, fibrosarcoma, osteosarcoma and cervix carcinoma.

Further, the gene construct of the invention has demonstrated effectiveness in suppressing replication and inducing cell senescence followed by cell death in the tumor cells having the following identified genetic defects: tumor suppressor gene RB and p53 mutation, oncogene myc activation, and oncogene N-ras and c-yes-1 activation.

Furthermore, the gene construct of the invention has demonstrated effectiveness in suppressing replication and inducing cell senescence followed by cell death in the tumor cells having normal endogenous tumor suppressor $RB^{110}$ and/or p53 gene expression.

In addition, the gene construct of the invention is able to suppress replication in lymphomas, leukemia and in tumor cells having tumor suppressor gene DCC and NF1 genetic defects, as well as in other tumor cell types in which the genetic defects are unknown or have yet to be identified.

3.3.5. Ex Vivo Treatment of Tumor or Cancer Tissues

In a preferred embodiment a tumor cell is transduced with a retrovirus vector, an adenovirus vector, a plasmid vector or any other appropriate vector capable of expressing the $p94^{RB}$ protein in that tumor cell. The cancer cell may be present in a blood or bone marrow sample collected from a leukemia patient. A dose of $p94^{RB}$ protein expressing retrovirus vector or adenovirus vector or plasmid vector or any other appropriate vector is administered to the sample of blood or bone marrow at a dose sufficient to transduce enough cells in the sample to produce a reduction in tumor cell numbers. The cell proliferation of the treated cancer cells will be slowed or terminated followed by a process similar to normal cellular differentiation or cell senescence. Analo-gously, blood or bone marrow or other tissue is treated ex vivo using an effective dose of a lipsome-encapsulated $p94^{RB}$ protein. Thereafter the sample may be returned to the donor or infused into another recipient.

3.3.6. In Vivo Treatment of Tumor or Cancer Tissues

Methods of administering viral vectors are well known. In general, the skilled artisan will appreciate that a retroviral vector, an adenovirus vector, a plasmid vector, or any other appropriate vector capable of expressing the $p94^{RB}$ protein can be administered in vivo to a cancer by a wide variety of manipulations. All such manipulations have in common the goal of placing the vector in sufficient contact with the target tumor to permit the vector to transduce or transfect the tumor cells. In a preferred embodiment, cancers present in the epithelial linings of hollow organs may be treated by infusing the vector suspension into a hollow fluid filled organ, or by spraying or misting into a hollow air filled organ. Thus, the tumor cell may be present in or among the epithelial tissue in the lining of pulmonary bronchial tree, the lining of the gastrointestinal tract, the lining of the female reproductive tract, genito-urinary tract, bladder, the gall bladder and any other organ tissue accessible to contact with the vector.

In another preferred embodiment, the cancer may be located in or on the lining of the central nervous system, such as, for example, the spinal cord, spinal roots or brain, so that vectors infused in the cerebrospinal fluid will contact and transduce the cells of the tumor in that space.

In another preferred embodiment, the cancer is a solid tumor. The skilled artisan will appreciate that the vector can be administered to the tumor by direct injection of the vector suspension into the tumor so that vectors will contact and transduce or transfect the tumor cells inside the tumor.

In yet another preferred embodiment, the cancer may be a cancer of the blood, blood forming organs or any organ directly perfused by the blood, so that vectors injected into the blood stream will contact and treat the cells of the cancer. Thus, the cancer may be a leukemia, a lymphoma or other tumor type and the tumor cell may be present in the blood, the bone marrow, the spleen, the thymus, the liver and any other blood perfused organ.

The skilled artisan will understand that the vector is administered in a composition comprising the vector together with a carrier or vehicle suitable for maintaining the transduction or transfection efficiency of the chosen vector and promoting a safe infusion. Such a carrier may be a pH balanced physiological buffer, such as a phosphate, citrate or bicarbonate buffer, a saline solution, a slow release composition and any other substance useful for safely and effectively placing the vector in contact with abnormally proliferating cells to be treated.

The invention is further described in the following examples which are in no way intended to limit the scope of the invention.

4. EXAMPLES

4.1 Preparation of Vectors for Expression of the Second In-Frame AUG Codon-Initiated RB Protein in Insect Cells The engineered derivatives of *Autographa california* Multiple Nuclear Polyhedrosis Virus ("AcMNPV") have been widely employed to produce high levels of accurately processed and biologically active proteins. This baculovirus propagates in cultured Fall Army worm *Spondoptera frugiperda* cells (Sf9 cells) and has a strong temporarily regulated promoter of the polyhedron gene whose product represents 50% or more of total cellular proteins during a lytic infection.

By in vivo recombination, the coding sequence of a foreign gene can easily be placed under the transcriptional control of the polyhedron promoter, resulting in a high level of expression. In addition, such proteins may be correctly folded and contain appropriate post-translational modifications like those proteins in the native higher eukaryotes.

By site-specific mutagenesis, two BamH1 sites were introduced into the RB cDNA at nucleotides +7 and +3230 (the A of the second in-frame AUG codon is designated +19). The resulted DNA molecule has the nucleotide sequence of FIG. 1 (SEQ ID NO:1; SEQ ID NO:2), which is also referred to herein as the second in-frame AUG codon-initiated RB protein gene, or the $p94^{RB}$ encoding gene. The coded-for protein has the sequence of FIG. 2 (SEQ ID NO:3) and is referred to herein as the second in-frame AUG codon-initiated RB protein, or the $p94^{RB}$ protein.

In an attempt to achieve maximal production of the second in-frame AUG codon-initiated RB protein in the baculovirus expression system, the recombinant transfer vector was constructed with insertion of the $p94^{RB}$ gene into the pVL1393 plasmid so that the $p94^{RB}$ gene was placed under the control of the polyhedron gene promoter.

As shown in FIG. 3, the resulting pVL-s-RB plasmid contains no additional AUG start codon upstream from the $p94^{RB}$ translation initiation site at nucleotide +19, and thus encodes a nonfusion $p94^{RB}$ protein. In a parallel study, the same strategy was employed to construct a $p110^{RB}$ expression vector which was designated pVL/1st AUG-RB.

Transfer of RB cDNAs from the recombinant vectors to the viral genome was accomplished by co-transfecting wild-type AcMNPV virus DNA with pVL-s-RB plasmid DNA or pVL/1st AUG-RB plasmid DNA. The recombinant viruses were subjected to three rounds of plaque purification to obtain a pure stock of RB-containing baculovirus, designated AcMNPV-RB94 and AcMNPV-RB110, respectively.

4.2 Purification of $p110^{RB}$ and $p94^{RB}$ Proteins

The $p110^{RB}$ and $p94^{RB}$ proteins were purified from baculovirus-infected insect cells by immunoaffinity chromatography. Briefly, insect cells were harvested 24 hours after the virus infection and lysed at 4° C. with EBC buffer (50 mM Tris-HC1, pH8.0, 120 mM NaCl, 0.5% NP-40, 50 µg/ml aprotinin). The lysate was clarified by centrifugation and the $p110^{RB}$- or $p94^{RB}$-containing supernatant was incubated with biotinylated WL-1 polyclonal anti-RB antibodies (Xu, H-J., et al., 1989, *Oncogene*, 4:807–812) at 4° C. overnight. The procedures for biotinylation of rabbit IgGs using succinimide ester followed the methods described by Bayer and Wilchek (Baylor, E. A. and Wilchek, M., 1980, *Methods Biochem. Anal.*, 26:1–45). The RB protein-IgG-biotin complex was collected on a streptavidin agarose gel column. Purified $p110^{RB}$ or $p94^{RB}$ were eluted from separate columns using 100 mM glycine (pH 2.2) and neutralized with 1M of phosphate (pH 8.0).

4.2.1. $p94^{RB}$ Shares Major Biochemical and Biological Properties With $p110^{RB}$ Since non-functional mutations of the retinoblastoma protein are characterized by defects in phosphorylation, viral oncoprotein association and nuclear localization (Templeton et al., 1991, *Proc. Natl. Acad. Sci., USA*, 88:3033–3037), the functional aspects of the artificial $p94^{RB}$ protein were studied for these characteristics.

First, to determine whether the RB proteins produced in the insect cells with the baculoviruses were associated with the nucleus, the AcMNPV-RB110 and AcMNPV-RB94 infected Sf9 cells were immunostained with MAb-1 anti-RB monoclonal antibody 24 h after infection. As shown in FIG. 4, intense staining was found exclusively in the nuclei of cells infected with either AcMNPV-RB110 (panel B) or AcMNPV-RB94 (panel C).

The $p110^{RB}$ and $p94^{RB}$ proteins purified from baculovirus-infected insect cells by immunoaffinity chromatography were tested for their ability to form a specific complex with SV40 T antigen. Briefly, equal amounts of $p94^{RB}$ or $p110^{RB}$ and T antigen were mixed and aliquots of the mixture were immunoprecipitated with PAB419 anti-T antibody. As shown in FIG. 5, mixing of $p94^{RB}$ (or $p110^{RB}$) with T antigen in vitro resulted in the co-immunoprecipitation of both under- and hypo-phosphorylated $p94^{RB}$ (lane 5), or $p110^{RB}$ (lane 3) with PAB419. The data demonstrated that either $p110^{RB}$ or $p94^{RB}$ protein can form a specific complex with SV40 T antigen. The AcMNPV-RB94 virus-infected insect cells appear to make hyperphosphorylated $p94^{RB}$ (lane 4), which was unable to form complexes with SV40 T antigen (compare lane 4 with lane 5).

The Western blot shown in FIG. 5 revealed an apparent relative molecular mass (Mr) of 94 kD for the second in-frame AUG codon-initiated RB protein. On SDS-PAGE, the $p94^{RB}$ protein (FIG. 5, lanes 4 and 5) was smaller than the naturally occurring 98 kDa proteins of unknown origin (Xu et al., 1989, *Oncogene*, 4:807–812) (FIG. 5, lane 1). Therefore, the second in-frame AUG codon-initiated RB protein of this invention ($p94^{RB}$) has not been found to occur naturally in human cells.

It is concluded that the second in-frame AUG codon-initiated $p94^{RB}$ protein produced in recombinant virus-infected insect cells is a artificial but stable nuclear phosphoprotein with its under- and hypo-phosphorylated forms being able to assemble specific complex with SV40 T antigen, as does the naturally occurring RB protein species, $p110^{RB}$.

4.3 Construction of Expression Vectors for Mammalian Cells

4.3.1. Subcloning of RB cDNA Fragments Encoding for the First and Second In-Frame AUG Codon-Initiated RB Proteins Subcloning of RB cDNA fragments encoding for the first and second in-frame AUG codon-Initiated RB proteins was accomplished by standard methods in the art. The methods for DNA manipulation were modified from Maniatis, T., Fritsch, E. F., and Sambrook, J. (1989): *Molecular Cloning (A Laboratory Manual)*, Cold Spring Harbor Laboratory, Cold Spring Harbor, N. Y.; and Ausubel, F. M., Brent, R., Kingston, R. E., Moore, D. D., Seidman, J. G., Smith, J. A., and Struhl, K. (1992): *Current Protocols in Molecular Biology*, John Wiley & Sons, New York.

4.3.2. Preparation of a DNA Molecule Encoding the Second

In-Frame AUG Codon-Initiated RB Protein.

A plasmid, p4.95BT (Friend et al., 1987, *Proc. Natl. Acad. Sci. USA*, 84:9059–9063) or F7 (Takahashi, R., Hashimoto, T., Xu, H.-J., et al., 1991, *Proc. Natl. Acad. Sci. USA*, 88:5257–5261) containing the full length retinoblastoma (RB) gene cDNA was digested with the restriction enzyme, Hind II, at nucleotide +7 and the restriction enzyme, ScaI, at nucleotide 3,230 (The A of the second in-frame AUG codon of the full length RB cDNA open reading frame was designated nucleotide +19). The resulted 3,230 bp RB cDNA fragment had two blunt ends. Conversion of the blunt ends to restriction enzyme BamHI sites was done by ligation of a synthetic BamHI oligonucleotide linker (GGGATCCC) to each blunt end of the fragment followed by digestion with the BamHI enzyme.

The desired RB cDNA fragment was inserted into the BamHI cloning site of a plasmid vector, pUC19, and propagated in the *Escherichia coli* strain, DH5 alpha bacterial cells. The recombinant plasmid was purified from a single DH5 alpha transformant and designated plasmid pUC-s-RB. This plasmid contains the desired RB cDNA fragment of 3,230 bp coding for the second in-frame AUG codon-initiated RB protein of 816 amino acids.

4.3.3. Preparation of A DNA Molecule Encoding the First In-Frame AUG Codon-Initiated RB Protein.

The full length RB cDNA plasmid was digested with the restriction enzyme, AcyI at nucleotide −322 and ScaI at nucleotide 3,230. The AcyI ends (overhang 5'-CG) were repaired by "filling in" the ends with the Klenow fragment of *E. coli* DNA polymerase I in the presence of all 4 dNTPs to generate blunt ends. Conversion of the blunt ends to restriction enzyme BamHI sites was done as described above. The resulted RB cDNA fragment of 3,552 bp was inserted into the plasmid pUC19 and propagated in the *Escherichia coli* strain DH5 alpha, which was subsequently purified from a single DH5 alpha transformant and designated plasmid pUC-f-RB. This plasmid contains the RB cDNA fragment of 3,552 bp coding for the first in-frame AUG codon-initiated RB protein of 928 amino acids.

4.3.4. Construction of $p94^{RB}$ Expression Plasmid Using A Human B-Actin Gene Promoter The RB cDNA fragment of 3,230 bp coding for the second in-frame AUG codon-initiated RB protein of 816 amino acids ($p94^{RB}$) was recovered from plasmid pUC-s-RB following the restriction enzyme, BamHI digestion, and re-inserted into the unique BamHI site of an expression plasmid, pHβAPr-1-neo (Gunning, P., et al., *Proc. Natl. Acad. Sci., USA*, 1987, 84:4831–4835) in a orientation that the $p94^{RB}$ coding sequence was under the direct control of the β-actin gene promoter. A plasmid vector with the correct insert orientation was selected by restriction endonuclease mapping after propagation in DH5 alpha *Escherichia coli* host cells, and was designated pβA-s-RB34 (FIG. 7B). The corresponding DH5 alpha strain that contains plasmids pβA-s-RB34 was thereafter designated DHB-s-RB34 (ATCC 69241, patent depository, American Type culture Collection).

The plasmid vector pβA-s-RB34 contains no additional AUG codon between the β-actin gene promoter and the second in-frame AUG codon of the RB coding sequence, and thus encodes a non-fusion $p94^{RB}$ protein. The plasmid vector pβA-s-RB34 also confers a dominant selectable marker (geneticin resistance) in eukaryotic cells through expression of the neomycin phosphotransferase (neo) under separate control of an SV40 early promoter (FIG. 7, sv-neo).

4.3.5. Construction of $p110^{RB}$ Expression Plasmid Using A Human B-Actin Gene Promoter The RB cDNA fragment of 3,552 bp coding for the first in-frame AUG codon-initiated RB protein of 928 amino acids ($p110^{RB}$) was recovered from plasmid pUC-f-RB and re-inserted into the expression plasmid pHβAPr-1-neo downstream from the β-actin gene promoter. The resulting plasmid vector was designated pβA-f-RB33 (FIG. 7A). The plasmid vector pβA-f-RB33 contains no additional AUG codon between the β-actin gene promoter and the first in-frame AUG codon of the RB coding sequence, and thus encodes a non-fusion $p110^{RB}$ protein.

4.3.6. Construction of $p94^{RBs}$ and $p110^{RB}$ Expression Plasmids Using A Cytomegalovirus Promoter (CMVp)

Alternatively, an expression plasmid, pCMV-Neo-Bam (Baker, S. J., et al., *Science*, 1990, 249:912–915) was used in place of plasmid pHβAPr-1-neo. The vector included cytomegalovirus (CMV) promoter/enhancer sequences, which could drive expression of the insert at the BamHI site, and splicing and polyadenylation sites derived from the rabbit β-globin gene, which ensured proper processing of the transcribed insert in the cells. A pBR322 origin of replication and β-lactamase gene facilitated propagation of the plasmid in *E. coli*. The plasmid conferred geneticin resistance (a selectable marker in eukaryotic cells) through expression of the neomycin phosphotransferase (neo) under the control of a herpes simplex virus (HSV) thymidine kinase promoter.

The same strategies as described supra in Sections 4.3.4 and 4.3.5 were employed to transfer the RB cDNA fragments of 3,230 bp and 3,552 bp from plasmids pUC-s-RB and pUC-f-RB, respectively, to the unique BamHI site in the expression vector, pCMV-Neo-Bam. The resulting plasmid vectors were designated by the names of pCMV-s-RB42, expressing the $p94^{RB}$ and pCMV-f-RB35, expressing the $p110^{RB}$ (FIG. 6). The corresponding *Escherichia coli* DH5 alpha strain which contains plasmids pCMV-s-RB42 was thereafter designated DHC-s-RB42 (ATCC 69240, patent depository, American Type Culture Collection).

4.3.7. Construction of $p94^{RB}$ Protein Expression Retrovirus Vectors

For this protocol, retroviral vector, pLLRNL (Miller, A. D., Law, M.-F., Verma, I. M., *Molec. Cell Biol.*, 1985, 5:431) and amphotropic retrovirus packaging cell line, PA317 (ATCC CRL9078) (Miller, A. D., and Buttimore, C., *Molec. Cell Biol.*, 1986, 6:2895–2902) are used.

A plasmid p4.95BT or F7 containing the full-length RB gene cDNA is digested with the restriction enzyme Hind II at nucleotide +7 (the A of the second in-frame AUG codon of the full-length RB cDNA open reading frame was designated nucleotide +19). Conversion of the Hind II site to restriction enzyme Hind III site is done by ligation of a synthetic Hind III oligonucleotide linker (CCAAGCTTGG) to the blunt ends of the linear plasmid DNA, followed by digestion with the Hind III enzyme. The linear plasmid DNA is further digested with restriction enzyme, ScaI, at nucleotide 3,230. The resulted RB cDNA fragment of 3,230 bp codes for the second in-frame AUG codon-initiated RB protein of 816 amino acids ($p94^{RB}$). This fragment has a 5'-Hind III site (cohesive end) and a 3'-ScaI site (blunt end), which facilitates its insertion into the retroviral vector, pLLRNL.

The vector pLLRNL is digested with two sets of restriction enzymes: Hind III/ClaI and SmaI/ClaI to delete the luciferase gene. Appropriate fragments are recovered from the agarose gel following electrophoresis, and ligated with the RB cDNA fragment of 3,230 bp to form a new vector, pLRB94RNL, in which the $p94^{RB}$ expression is under the control of the long terminal repeat sequences of Moloney murine leukemia virus (MuLV LTRs).

The basic protocol for construction of the retroviral vector, pLRB94RNL, is modified from Huang, H.-J. S., et al., 1988, *Science*, 242:1563–1566.

Alternatively, the vector pLLRNL is digested with a single restriction enzyme, Hind III, to delete the luciferase gene, as well as the Rous sarcoma virus promoter (RSV). An appropriate DNA fragment is recovered from the p94$^{RB}$ expression plasmid, pCMV-s-RB42 (or pβA-s-RB34). The recovered DNA fragment, which contains the 3,230 bp RB cDNA fragment and 5'-flanking CMV promoter (or β-actin promoter), is inserted into the ClaI restriction site of the retroviral vector. Conversion between the restriction enzyme sites is done by the methods as described supra in Section 4.3.7.

In the resulting p94$^{RB}$ expression retrovirus vector, the p94$^{RB}$ gene is under the control of an internal promoter (the CMV promoter or β-actin promoter), while the Tn5 neomycin-resistance gene (Neo) is under the control of the MuLV LTRs.

A safe and efficient amphotropic packaging cell line is necessary for transfer of retroviral vector genes into human cancer cells. The virus packaging methods are modified from the method of Miyanohara et al., *Proc. Natl. Acad. Sci., USA*, 1988, 85:6538–6542. For this protocol, the PA317 packaging cell line is used. This packaging cell line has received prior approval for use in human gene therapy clinical trials.

The retroviral vector (pLRB94RNL) DNA is transfected into PA317 packaging cells by LIPOFECTIN reagent (GIBCO BRL Life Technologies, Inc., Gaithersburg, Md.) or electroporation methods as described in Sections 4.4.1. infra. Single colonies are isolated by selection in G418-containing medium (400 µg/ml) and expanded into mass cultures. To titer the virus produced by selected PA317 clones, dilutions of cell-free culture medium from each PA317 clone are applied to 208F rat fibroblasts (indicator cells) in the presence of POLYBRENE (Sigma, 4 µg/ml) and G418 selection (400 µg/ml) is started 24 hours after infection.

After two weeks, G418-resistant colonies are visualized by Giemsa staining and viral titers are determined (colony-forming units per milliliter, cfu/ml). PA317 clones producing high virus titers are then assayed for human p94$^{RB}$ protein expression by Western immunoblotting as described previously (Xu, H.-J., et al., *Oncogene*, 1991, 6:1139–1146). Cell-free culture media from selected PA317 clones expressing high level of human p94$^{RB}$ protein are then applied to human cancer cells ex vivo or in vivo.

4.3.8. Construction of p94$^{RB}$ Protein Expression Adenovirus Vectors

The recombinant adenovirus Ad-RB94 is constructed from the adenovirus type 5 (Ad5) deletion mutant, Ad-dl324, and a plasmid, pTG5955, in which the human CFTR cDNA has been replaced by the human RB cDNA fragment of 3,230 bp coding for the p94$^{RB}$ protein. The plasmid pTG5955 containing the RB cDNA insert is linearized by restriction enzyme ClaI cleavage and co-transfected with the large fragment of ClaI-cut Ad-dl324 DNA into 293 (ATCC CRL1573) cells to allow homologous recombination to occur, followed by replication and encapsidation of recombinant adenoviral DNA into infectious virions and the formation of plaques. Individual plaques are isolated and amplified in 293 cells, viral DNA is isolated and recombinant adenovirus plaques containing the human RB cDNA (Ad-RB94) are identified by restriction cleavage and Southern analysis. Ad-RB94 viruses are propagated in 293 cells and recovered 36 hours after infection. The viral preparation is purified by CsCl density centrifugation, and stored in virus dialysis buffer (10 mM Tris-Hcl, pH7.4; 1 mM MgCl$_2$) at 4° C. for immediate use; or stored at −70° C. prior to use (with the addition of 10% glycerol). The basic protocol for construction of the recombinant adenovirus Ad-RB94 is modified from Rosenfeld, M. A., et al., *Cell.*, 1992, 68:143–155.

4.3.9. Physical DNA Transfer Method

An alternative gene transfer method that has been approved for use in humans by the Food and Drug Administration is the transfer of plasmid DNA in liposomes directly to tumor cells in situ (Nabel, E. G., et al., 1990, *Science*, 249:1285–1288). Plasmid DNA is easy to certify for use in humans because, unlike retroviral vector, it can be purified to homogeneity.

The p94$^{RB}$ expressing plasmid vectors pCMV-s-RB42 or pβA-s-RB34 are used to form complexes with liposomes, and directly treat tumor cells in vivo (or ex vivo). In this procedure, as described in Section 4.4.1 infra, stable integration of the DNA into transfected tumor cells is not required for gene therapy as transient expression may suffice.

4.4. Treatment of Human Tumor Cells In Vitro With p94$^{RB}$ Plasmid Vectors pβA-s-RB34 or pCMV-s-RB42.

4.4.1. Treatment of RB-Defective Human Tumor Cells In Vitro

Human tumor cells having known RB gene deficiencies were treated with the p94$^{RB}$ plasmid vector pβA-s-RB34 (or pCMV-s-RB42). These include: 1) human bladder carcinoma cell line, 5637, (ATCC HTB9); 2) human breast carcinoma cell line, MDA-MB-468 (ATCC HTB132); 3) human non-small cell lung carcinoma cell line, H2009 (Kratzke, R. A., et al., 1992, *The Journal of Biological Chemistry*, 267:25998–26003); 4) human prostate carcinoma cell line, DU145 (ATCC HTB81); 5) human osteosarcoma cell line, Saos2 (ATCC HTB85); and 6) human fibrosarcoma metastatic to lung cell line, Hs913T (ATCC HTB152).

For treatment, tumor cells were transiently transfected with the plasmid DNA pβA-s-RB34 (or pCMV-s-RB42) via LIPOFECTIN reagent (GIBCO BRL Life Technologies, Inc. Gaithersberg, Md.). Similar results have been obtained from transfection using calcium phosphate or electroporation methods.

The following procedures for transfection using LIPOFECTIN were modified from the manufacturer's specifications. Tumor cells were seeded in 100-mm dishes in appropriate growth medium supplemented with serum. The cells were incubated at 37° C. in a 5% CO$_2$ environment until the cells were 40–60% confluent. This usually took 18–24 hours, but the time varied among cell types. The following solution was prepared in 17×75 mm polystyrene tubes: Solution A—for each dish of cells to be transfected, 5–10 µg of plasmid DNA were diluted into a final volume of 100 µl with serum-free medium; Solution B—for each dish of cells to be transfected, 30–50 µl of LIPOFECTIN reagent was diluted into a final volume of 100 µl with serum-free medium. The two solutions were combined, mixed gently, and incubated at room temperature for 10–15 min. The LIPOFECTIN reagent interacted spontaneously with plasmid DNA to form a lipid-DNA complex. While the lipid-DNA complex was forming, the cells were washed twice with 6 ml of serum-free medium. For each transfection, 6 ml of serum-free medium were added to each polystyrene tube containing the lipid-DNA complex. The solution was mixed gently, and the medium-complex was overlayed onto the cells. The dishes were then swirled gently to ensure uniform distribution. The dishes were then incubated at 37° C. in a 5% $CO_2$ incubator. After 12 to 24 hours the medium-complex was replaced with appropriate growth medium containing 10% fetal calf serum.

In parallel studies, tumor cells were transfected with the plasmid DNA pβA-f-RB33 or pCMV-f-RB35 which expresses the p110$^{RB}$. The following assays were used to evaluate the growth inhibitory effects of introducing p94$^{RB}$ versus p110$^{RB}$ expression in RB defective tumor cells:

1) DNA synthesis in tumor cells treated with plasmid vectors.

After plasmid DNA treatment the tumor cells were labeled with [$^3$H]-thymidine for 2 hours, then transferred to polylysine-coated slides, fixed and immunocytochemically stained with a monoclonal anti-RB antibody, MAb-1 (Triton Biosciences, Inc. Alameda, Calif.). The RB-positive transfected cells were counted under the microscope. The slides were then coated with Kodak NTB2 autoradiographic emulsion and exposed for 7–10 days. The [$^3$H]-thymidine labeling and RB protein immunocytochemical staining were done according to the methods previously described (Xu et al., Oncogene, 1991, 6:1139–1146). About 400 to 1600 RB-positive and 600 RB-negative tumor cells were assessed for each determination of [$^3$H]-thymidine uptake. The study demonstrated that the RB-defective tumor cells expressing p94$^{RB}$ did not progress through the cell cycle, as evidenced by their failure to incorporate [$^3$H]-thymidine into DNA (Table 2). However, the percentage of cells undergoing DNA replication was only slightly lower in cells producing p110$^{RB}$ than in cells that were RB-negative (Table 2).

TABLE 2

Immunocytochemical Staining and [$^3$H] Thymidine Incorporation of RB-Defective Tumor Cells Following Transfection With p94$^{RB}$ or p110$^{RB}$ Expression Plasmids

| Recipient Cells | Promoter | Protein Expressed | Cells Incorporating [$^3$H] Thymidine RB+ | RB– |
|---|---|---|---|---|
| 5637 | β-actin gene promoter | p110$^{RB}$ | 34% | 45% |
|  |  | p94$^{RB}$ | 2.3% | 43% |
|  | Cytomegalovirus promoter/enhancer | p110$^{RB}$ | 21% | — |
|  |  | p94RB | 1.8% | — |
| MDA-MB-468 | Cytomegalovirus promoter/enhancer | p110$^{RB}$ | 14% | 40% |
|  |  | p94$^{RB}$ | 0.5% | 39% |
| H2009 | β-actin gene promoter | p110$^{RB}$ | 19% | 26% |
|  |  | p94$^{RB}$ | 0.1% | 27% |
| DU145 | Cytomegalovirus Promoter/enhancer | p110$^{RB}$ | 23% | 33% |
|  |  | p94$^{RB}$ | 1.0% | 33% |
| Hs913T | Cytomegalovirus promoter/enhancer | p110$^{RB}$ | 18% | 34% |
|  |  | p94$^{RB}$ | 0.9% | 36% |
| Saos2 | Cytomegalovirus promoter/enhancer | p110$^{RB}$ | 19% | 32% |
|  |  | p94$^{RB}$ | 0.9% | 35% |

2) Colony formation assay.

Approximately 48 hours after transfection the tumor cells were replated at a density of $10^5$ cells per 100 mm dish with selected medium containing G418 of 400–600 µg/ml. Cells were cultured for 2 to 3 weeks and colonies of >100 cells were scored. The data are illustrated in Table 3. Cells treated with plasmid vectors expressing p94$^{RB}$ formed approximately four-fold fewer colonies than those transfected with p110$^{RB}$ plasmid vectors. The difference was statistically significant (p <0.05 by t-test).

Furthermore, in those colonies that did form after p94$^{RB}$ plasmid DNA treatment, p94$^{RB}$ protein expression was no longer observed. Failure to isolate long-term cultures expressing the p94$^{RB}$ protein in treated tumor cells shows that p94$^{RB}$ did suppress tumor cell growth. In contrast, 7 of 48 cell lines (approximately 15%) derived from tumor cells after transfection with the p110$^{RB}$ plasmid DNA were found to express the p110$^{RB}$ protein. This percentage was consistent with results expected in human cells transfected with a vector containing two independent transcription units and therefore introduction of p110$^{RB}$ expression does not exert growth inhibitory effects on RB-defective tumor cells.

TABLE 3

Growth inhibitory effects of introducing p110$^{RB}$ and p94$^{RB}$ expression into RB-defective bladder carcinoma cell line, 5637 (HTB9). Each number represents 6 to 11 dishes.

|  | Number of G418-Resistant Colonies Formed | | |
|---|---|---|---|
| Vector Type | Vector | p110$^{RB}$ | p94$^{RB}$ |
| pCMV-Neo-Bam | 280 | 24 | 6 |
| pHβAPr-1-neo | — | 33 | 8 |

3) The Effect of p94$^{RB}$ Expression on Cellular Morphology

The HTB9 transfectants were also immunostained with MAb-1 anti-RB monoclonal antibody about 24 hours after transfection. The staining results are illustrated in FIG. 8.

As demonstrated in FIG. 8, the majority of RB-positive, p94$^{RB}$-expressing HTB9 cells become very large in size, with lower nucleocytoplasmic ratio, or higher incidence of being multinucleated cells (panel C), a morphological change frequently associated with cellular senescence. However, such a morphological change has not been seen in group A, mock-transfected HTB9 cells and group B, p110$^{RB}$ expressing RB-positive HTB9 cells (FIG. 8, panels A and B).

4.4.2. Treatment of Human Tumor Cells Having Normal (p110$^{RB}$) RB Expression (RB+)

Two RB+ human cell lines (i.e., having no RB gene defect), including a human fibrosarcoma cell line, HT1080 (ATCC CCL121), and human cervix carcinoma cell line, HeLa (ATCC CCL2) were treated with the p94$^{RB}$ protein expression plasmid, pCMV-s-RB42, using the LIPOFECTIN reagent as described supra. In parallel studies, these cell lines were also transfected with the p110$^{RB}$ protein expression plasmid, pCMV-f-RB35. The colony formation assay as described supra was used to evaluate the growth inhibitory effects of introducing exogenous p94$^{RB}$ versus p110$^{RB}$ expression in RB$^+$ tumor cells. As shown in Table 4, expression of the p94$^{RB}$ protein dramatically inhibited the cell growth of HT1080 and HeLa cells. There was a two- to nine-fold reduction in the number of G418-resistant colonies formed after treated with the plasmid victor pCMV-s-RB42 expressing p94$^{RB}$, while no such effect was observed by transfection with the pCMV-f-RB35 plasmid (expressing p110$^{RB}$ protein). The difference was statistically significant (the two-tailed P values were less than 0.03 as calculated by the paired t-test).

TABLE 4

Growdth inhibitory effects of introducing p110$^{RB}$ and p94$^{RB}$ expression into RB-positive human fibrosarcoma cell line, HT1080 and the RB positive human cervix carcinoma cell line, HeLa. The RB expression was under the control of cytomegalovirus (CMV) promoter. For each experiment, three 5-cm$^2$ dishes were transfected and the total colonies counted after ten days of selection in G418 (1 mg/ml).

| Recipient Cells | Experiment | No. of G418-Resistant Colonies Formed | | |
|---|---|---|---|---|
| | | Vector | p110$^{RB}$ | p94$^{RB}$ |
| HT1080 | 1 | 94 | 129 | 14 |
| | 2 | 88 | 122 | 16 |
| | 3 | 100 | 120 | 17 |
| | 4 | 99 | 110 | 15 |
| HeLa | 1 | 24 | 20 | 10 |
| | 2 | 25 | 24 | 9 |

4.5 Half-Life and Phosphorylation state of the p94$^{RB}$ Protein In Host Cells: The Distinct Properties of p94$^{RB}$ The half-life of transiently expressed p94$^{RB}$ and p110$^{RB}$ proteins in transfected bladder carcinoma cell line, 5637 (ATCC HTB9) was measured by pulse-labeling of transfected 5637 cells with [$^{35}$S]-methionine followed by a chase with excess unlabeled methionine (FIG. 9).

The bladder tumor cells were transfected in multiple dishes with either p110$^{RB}$ (FIG. 9, left) or p94$^{RB}$ (FIG. 9, right) expression plasmids. Twenty-four hours after transfection the cells were labeled with [$^{35}$S]-methionine and chased with excess unlabeled methionine for 0, 6, 12 and 24 hours, respectively. RB proteins were determined by immunoprecipitation.

The half-life of p94$^{RB}$ protein in the transfected 5637 cells was determined to be 12 hours. In contrast, the half-life of p110$^{RB}$ protein was 4–6 hours. Therefore, p94$^{RB}$ protein expressed in host tumor cells has a slower turnover, which is believed to contribute to its efficacy as a suppressor of both RB+ and RB− tumor cell replication.

The comparative phosphorylation states of p110$^{RB}$ and p94$^{RB}$ in transiently transfected 5637 cells were determined by Western blot analysis: cell-lysates were made from WI-38, parental 5637 and pβA-f-RB33 (expressing p110$^{RB}$, Section 4.3.5) or pβA-s-RB34 (expressing p94$^{RB}$ Section 4.3.4) plasmid transfected 5637 cells approximately 24 hours after transfection. The basic protocal for Western blot analysis was described in Xu, H-J., et al., 1989, Oncogene, 4:807– 812. Each lane was loaded with 40 μl of the lysate corresponding to 4×10$^5$ cultured cells. Proteins were separated by 8% SDS-PAGE and electroblotted to a PVDF membrane. After blocking with 3% non-fat milk in TBST (10 mM Tris-HCl, pH8.0, 150 mM NaCl, 0.05% Tween 20), the membrane was incubated with MAb-1 monoclonal anti-RB antibody at 0.1 μg/cm$^2$ overnight. The blot was then probed by the Enhanced Chemiluminescence (ECL) (Amersham Corporation, Arlington Heights, Ill.) immunodetection method. X-ray films were exposed for 2 seconds (FIG. 10, lane 1) or 30 seconds (FIG. 10, lanes 2–4).

Of particular interest was the fact that the RB-defective bladder carcinoma cell line, 5637, failed to phosphorylate the p94$^{RB}$ protein as shown by Western blot analysis (FIG. 10, lane 4), although the p110$^{RB}$ proteins expressed in transfected 5637 cells were fully phosphorylated (FIG. 10, lane 3). Therefore, the presence of only unphosphorylated p94$^{RB}$ proteins may also account for the failure of transfected 5637 tumor cells to enter S phase, and this in turn may cause cellular senescence and cell death.

4.6. Treatment of Human Bladder Cancers In Vivo.

The human bladder cancer represents an ideal model for practicing tumor suppressor gene therapy of solid tumors by infusing the p94$^{RB}$ protein expression retroviral vectors into the bladder. The original experimental model of human bladder cancer was established by Dr. Peter A. Jones and his colleagues (Ahlering, T. E., et al., Cancer Res., 1987, 47:6660–6665). It has been shown that human bladder tumor cells of RT4 cell line established from a superficial papillary tumor (which usually does not metastasize) produced tumors only locally when injected by a 22-gauge catheter into the bladder of female nude mice. In contrast, the EJ bladder carcinoma cells which were originally isolated from a more aggressive human bladder cancer produced invasive tumors in the nude mouse bladders which metastasized to the lung spontaneously (Ahlering, T. E., et al., Cancer Res., 1987, 47:6660–6665). Therefore, this model can be used for treatment of experimental bladder cancer by in vivo gene transfer with retroviral vectors.

Tumor cells from RB minus human bladder carcinoma cell line, 5637 (ATCC HTB9) and RB$^+$ human bladder carcinoma cell line, SCaBER (ATCC HTB3) are injected directly into the bladders of female athymic (nu/nu) nude mice (6 to 8 weeks of age) by a catheter as initially reported by Jones and his colleagues (Ahlering, T. E., et al., Cancer Res., 1987, 47:6660–6665).

Development and progression of the nude mouse bladder tumors are monitored using a fiber-optical system to which a TV monitor is attached. The experimental tumors are subsequently treated with retrovirus vectors expressing the p94$^{RB}$.

Supernatants with high virus titers are obtained from tissue culture media of selected PA317 clones expressing high level of human p94$^{RB}$ protein (Section 4.3.7) and confirmed as free of replication-competent virus prior to use. The retroviral vector suspension at high titers ranging from 4×10$^4$ to greater than 1×10$^7$ colony-forming unit (cfu)/ml, and more preferably at a titer greater than 1×10$^6$ cfu/ml is then infused directly into the mouse bladders via a catheter to treat the tumors. The skilled artisan will understand that such treatments can be repeated as many times as necessary via a catheter inserted into the bladder. The tumor regression following transferring the p94$^{RB}$ gene is monitored frequently via the fiber-optic system mentioned above.

The same procedure as described above is used for treating the human bladder cancer except that the retroviral vector suspension is infused into a human bladder bearing cancer.

4.7. In Vivo Studies Using an Orthotopic Lung Cancer Model

Human large cell lung carcinoma, NCI-H460 (ATCC HTB177) cells which have normal p110$^{RB}$ expression are injected into the right mainstream bronchus of athymic (nu/nu) nude mice (10$^5$ cells per mouse). Three days later the mice are inoculated endobronchically with supernatant from the p94$^{RB}$, or p110$^{RB}$ retrovirus producer cells daily for three consecutive days. Tumor formation is suppressed in the group of mice treated with the p94$^{RB}$ retrovirus supernatant. In contrast, in the other group, which is treated with p110$^{RB}$ retrovirus supernatant, the majority of mice develop endobronchial tumors. This indicates that the p94$^{RB}$-expressing retrovirus inhibits growth of RB+ non-small cell lung carcinoma (NSCLC) cells, whereas the p110$^{RB}$-expressing retrovirus does not.

4.8. Treatment of Human Non-Small Cell Lung Cancers In Vivo.

Non-small cell lung cancer patients having an endobronchial tumor accessible to a bronchoscope, and also having a bronchial obstruction, are initially selected for $p94^{RB}$ gene therapy. Treatment is administered by bronchoscopy under topical or general anesthesia. To begin the procedure, as much gross tumor as possible is resected endoscopically. A transbronchial aspiration needle (21G) is passed through the biopsy channel of the bronchoscope.

The residual tumor site is injected with the appropriate retroviral vector supernatant (Section 4.3.7), adenovirus Ad-RB94 suspension (Section 4.3.8) or $p94^{RB}$-expressing plasmid vector-liposome complexes (Section 4.3.4 and 4.3.6) at a volume of 5 ml to 10 ml. Protamine is added at a concentration of 5 µg/ml. The injections of therapeutic viral or plasmid supernatant comprising one or more of the vectors are administered around and within the tumor or tumors and into the submucosa adjacent to the tumor. The injections are repeated daily for five consecutive days and monthly therafter. The treatment may be continued as long as there is no tumor progression. After one year the patients are evaluated to determine whether it is appropriate to continue therapy.

In addition, as a precaution the patients wear a surgical mask for 24 hours following injection of the viral supernatant. All medical personnel wear masks routinely during bronchoscopy and injection of the viral supernatant. Antitussive is prescribed as necessary.

4.9 Treatment or Prevention of Human Lung Carcinomas With Liposome-Encapsulated Purified $p94^{RB}$ Protein In yet another alternative, target tumor or cancer cells are treated by introducing $p94^{RB}$ protein into cells in need of such treatment by any known method. For example, liposomes are artificial membrane vesicles that have been extensively studied for their usefulness as delivery vehicles of drugs, proteins and plasmid vectors both in vitro or in vivo (Mannino, R. J, et al., 1988, *Biotechniques*, 6:682– 690). Proteins such as erythrocyte anion transporter (Newton, A. C. and Huestis, W. H., *Biochemistry*, 1988, 27:4655–4659), superoxide dismutase and catalase (Tanswell, A. K. et al., 1990, *Biochmica et Biophysica Acta*, 1044:269–274), and UV-DNA repair enzyme (Ceccoll, J. et al. *Journal of Investigative Dermatology*, 1989, 93:190–194) have been encapsulated at high efficiency with liposome vesicles and delivered into mammalian cells in vitro or in vivo.

Further, small-particle aerosols provide a method for the delivery of drugs for treatment of respiratory diseases. For example, it has been reported that drugs can be administered in small-particle aerosols by using liposomes as a vehicle. Administered via aerosols, the drugs are deposited rather uniformly on the surface of the nasopharynx, the traceheobronchial tree and in the pulmonary area (Knight, V. and Gilbert, B., 1988, *European Journal of Clinical Microbiology and Infectious Diseases*, 7:721–731).

To treat or prevent lung cancers, the therapeutic $p94^{RB}$ protein is purified, for example, from recombinant baculovirus AcMNPV-RB94 infected insect cells by immunoaffinity chromatography (Sections 4.1 and 4.2) or any other convenient source. The $p94^{RB}$ protein is mixed with liposomes and incorporated into the liposome vesicles at high efficiency. The encapsulated $p94^{RB}$ is active. Since the aerosol delivery method is mild and well-tolerated by normal volunteers and patients, the $p94^{RB}$-containing liposomes can be administered to treat patients suffering from lung cancers of any stage and/or to prevent lung cancers in high-risk population. The $p94^{RB}$ protein-containing liposomes are administered by nasal inhalation or by a endotracheal tube via small-particle aerosols at a dose sufficient to suppress abnormal cell proliferation. Aerosolization treatments are administered to a patient for 30 minutes, three times daily for two weeks, with repetition as needed. The $p94^{RB}$ protein is thereby delivered throughout the respiratory tract and the pulmonary area. The treatment may be continued as long as necessary. After one year the patent's overall condition will be evaluated to determine if continued therapy is appropriate.

5. Deposit of Microorganisms

The following were deposited on Feb. 10, 1993 with the American Type Culture Collection, 12301 Parklawn Drive, Rockville, Md. 20852:

| *Escherichia coli* DH5α | ATCC Designation |
| --- | --- |
| DHC-S-RB42 | 69240 |
| DHB-S-RB34 | 69241 |

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the claims. Various publications are cited herein, the disclosures of which are incorporated by reference in their entireties.

We claim:

1. A DNA molecule encoding p94$^{RB}$ having an amino acid sequence according to SEQ ID NO:3, provided that said DNA molecule does not also code for p110$^{RB}$.

2. The DNA molecule according to claim 1, said DNA molecule having a DNA sequence according to SEQ ID NO:1.

3. An expression vector comprising said DNA molecule according to claim 1 which inserts said p94$^{RB}$ encoding DNA molecule into a mammalian host cell and expresses p94$^{RB}$ therein.

4. The expression vector according to claim 3, wherein said expression vector is selected from the group consisting of a plasmid and a viral vector.

5. The expression vector according to claim 3 wherein said viral vector is selected from a group consisting of a retroviral vector, an adenoviral vector, and a herpesviral vector.

6. The expression vector according to claim 3 wherein said expression vector is plasmid pCMV-s-RB42.

7. The expression vector according to claim 3 wherein said expression vector is plasmid pβA-s-RB34.

8. The expression vector according to claim 3 wherein said expression vector is a retrovirus and said p94$^{RB}$ encoding gene is under the control of a promoter selected from the group consisting of a retroviral promoter, a CMV promoter and a β-actin promoter.

9. The expression vector according to claim 3 wherein said expression vector is an adenovirus and said p94$^{RB}$ encoding gene is under the control of a promoter selected from the group consisting of an adenoviral promoter, a CMV promoter and a β-actin promoter.

10. An expression vector comprising said DNA molecule according to claim 2, which inserts said p94$^{RB}$ encoding DNA molecule into a mammalian host cell and expresses p94$^{RB}$ therein.

11. The DNA according to claim 1 which is substantially isolated and purified.

12. The DNA according to claim 2 which is substantially isolated and purified.

* * * * *